US011118965B2

(12) United States Patent
Rogers et al.

(10) Patent No.: US 11,118,965 B2
(45) Date of Patent: Sep. 14, 2021

(54) MINIATURIZED ELECTRONIC SYSTEMS WITH WIRELESS POWER AND NEAR-FIELD COMMUNICATION CAPABILITIES

(71) Applicant: The Board of Trustees of the University of Illinois, Urbana, IL (US)

(72) Inventors: John A. Rogers, Wilmette, IL (US); Anthony R. Banks, Savoy, IL (US); Jeonghyun Kim, Urbana, IL (US); Gregory Brown, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 16/861,608

(22) Filed: Apr. 29, 2020

(65) Prior Publication Data
US 2020/0326231 A1 Oct. 15, 2020

Related U.S. Application Data

(63) Continuation of application No. 15/578,602, filed as application No. PCT/US2016/035336 on Jun. 1, 2016, now Pat. No. 10,677,647.

(Continued)

(51) Int. Cl.
*G06K 19/00* (2006.01)
*G01J 1/42* (2006.01)
(Continued)

(52) U.S. Cl.
CPC .............. *G01J 1/42* (2013.01); *A61B 5/6826* (2013.01); *A61B 6/00* (2013.01); *G01J 1/429* (2013.01);
(Continued)

(58) Field of Classification Search
CPC .. G06K 19/00; G06K 19/04; G06K 19/06046; G06K 19/07
(Continued)

(56) References Cited

U.S. PATENT DOCUMENTS

| 3,949,410 A | 4/1976 | Bassous |
| 4,058,418 A | 11/1977 | Lindmayer |

(Continued)

FOREIGN PATENT DOCUMENTS

| DE | 202004015373 | 2/2005 |
| WO | WO 98/049936 | 11/1998 |

(Continued)

OTHER PUBLICATIONS

Ahn et al. "Stretchable electronics: materials, architectures and integrations," J Phys. D: Appl. Phys., 2012, 45:103001 (14 pp.).

(Continued)

*Primary Examiner* — Daniel St Cyr
(74) *Attorney, Agent, or Firm* — Leydig, Voit & Mayer, Ltd.

(57) ABSTRACT

The invention provides systems and methods for tissue-mounted electronics and photonics. Devices of some embodiments of the invention implement high performance, and optionally flexible, device components having miniaturized formats in device architectures that minimize adverse physical effects to tissue and/or reduce interfacial stresses when mounted on tissue surfaces. In some embodiments, the invention provides complementary tissue mounting strategies providing for mechanically robust and/or long term integration of the present devices, for example, via mounting on tissue surfaces that are not subject to rapid growth or exfoliation processes such as the fingernail, toenail, tooth or earlobe. Devices of the invention are versatile and support a broad range of applications for sensing, (Continued)

actuating and communication including applications for near field communication, for example, for password authentication, electronic transactions and biometric sensing.

19 Claims, 34 Drawing Sheets

Related U.S. Application Data

(60) Provisional application No. 62/169,308, filed on Jun. 1, 2015, provisional application No. 62/169,983, filed on Jun. 2, 2015, provisional application No. 62/218,345, filed on Sep. 14, 2015, provisional application No. 62/218,321, filed on Sep. 14, 2015.

(51) Int. Cl.
| | | |
|---|---|---|
| *A61B 5/00* | (2006.01) | |
| *G06K 19/07* | (2006.01) | |
| *G01T 1/00* | (2006.01) | |
| *A61B 6/00* | (2006.01) | |
| *H02J 50/30* | (2016.01) | |
| *G01J 5/10* | (2006.01) | |
| *G06K 19/077* | (2006.01) | |
| *A61B 5/1455* | (2006.01) | |

(52) U.S. Cl.
CPC .................. *G01J 5/10* (2013.01); *G01T 1/00* (2013.01); *G06K 19/0716* (2013.01); *G06K 19/0723* (2013.01); *G06K 19/07722* (2013.01); *H02J 50/30* (2016.02); *A61B 5/14552* (2013.01); *A61B 2560/0214* (2013.01); *A61B 2560/0242* (2013.01); *A61B 2562/028* (2013.01); *A61B 2562/0271* (2013.01)

(58) Field of Classification Search
USPC ........... 235/487, 492, 462.46, 472.02
See application file for complete search history.

(56) References Cited

U.S. PATENT DOCUMENTS

| | | |
|---|---|---|
| 4,392,451 A | 7/1983 | Mickelsen et al. |
| 4,471,003 A | 9/1984 | Cann |
| 4,487,162 A | 12/1984 | Cann |
| 4,663,828 A | 5/1987 | Hanak |
| 4,715,235 A | 12/1987 | Fukui et al. |
| 4,761,335 A | 8/1988 | Aurichio et al. |
| 4,766,670 A | 8/1988 | Gazdik et al. |
| 4,784,720 A | 11/1988 | Douglas |
| 4,855,017 A | 8/1989 | Douglas |
| 5,041,973 A | 8/1991 | Lebron et al. |
| 5,086,785 A | 2/1992 | Gentile et al. |
| 5,118,400 A | 6/1992 | Wollam |
| 5,178,957 A | 1/1993 | Kolpe et al. |
| 5,204,144 A | 4/1993 | Cann et al. |
| 5,313,094 A | 5/1994 | Beyer et al. |
| 5,316,017 A | 5/1994 | Edwards et al. |
| 5,320,967 A | 6/1994 | Avallone et al. |
| 5,339,180 A | 8/1994 | Katoh |
| 5,403,700 A | 4/1995 | Heller et al. |
| 5,427,096 A | 6/1995 | Bogusiewicz et al. |
| 5,434,751 A | 7/1995 | Cole, Jr. et al. |
| 5,455,178 A | 10/1995 | Fattinger |
| 5,469,845 A | 11/1995 | Delonzor et al. |
| 5,501,893 A | 3/1996 | Laermer et al. |
| 5,525,815 A | 6/1996 | Einset |
| 5,545,291 A | 8/1996 | Smith et al. |
| 5,625,471 A | 4/1997 | Smith |
| 5,648,148 A | 7/1997 | Simpson |
| 5,678,737 A | 10/1997 | White |
| 5,687,737 A | 11/1997 | Branham et al. |
| 5,691,245 A | 11/1997 | Bakhit |
| 5,753,529 A | 5/1998 | Chang et al. |
| 5,757,081 A | 5/1998 | Chang et al. |
| 5,767,578 A | 6/1998 | Chang et al. |
| 5,772,905 A | 6/1998 | Chou |
| 5,783,856 A | 7/1998 | Smith et al. |
| 5,790,151 A | 8/1998 | Mills |
| 5,817,242 A | 10/1998 | Biebuyck et al. |
| 5,824,186 A | 10/1998 | Smith et al. |
| 5,904,545 A | 5/1999 | Smith et al. |
| 5,907,189 A | 5/1999 | Mertol |
| 5,915,180 A | 6/1999 | Hara et al. |
| 5,917,534 A | 6/1999 | Rajeswaran |
| 5,928,001 A | 7/1999 | Gillette et al. |
| 5,955,781 A | 9/1999 | Joshi et al. |
| 5,976,683 A | 11/1999 | Liehrr et al. |
| 5,998,291 A | 12/1999 | Bakhit et al. |
| 6,024,702 A | 2/2000 | Iversen |
| 6,057,212 A | 5/2000 | Chan et al. |
| 6,080,608 A | 6/2000 | Nowak |
| 6,097,984 A | 8/2000 | Douglas |
| 6,165,391 A | 12/2000 | Vedamuttu |
| 6,171,730 B1 | 1/2001 | Kuroda et al. |
| 6,225,149 B1 | 5/2001 | Gan et al. |
| 6,236,883 B1 | 5/2001 | Ciaccio et al. |
| 6,265,326 B1 | 7/2001 | Ueno |
| 6,267,775 B1 | 8/2001 | Schulte |
| 6,274,508 B1 | 8/2001 | Jacobsen et al. |
| 6,276,775 B1 | 8/2001 | Schulte |
| 6,277,712 B1 | 8/2001 | Kang et al. |
| 6,281,038 B1 | 8/2001 | Jacobsen et al. |
| 6,284,418 B1 | 9/2001 | Trantolo |
| 6,291,896 B1 | 9/2001 | Smith |
| 6,316,278 B1 | 11/2001 | Jacobsen et al. |
| 6,316,283 B1 | 11/2001 | Saurer |
| 6,317,175 B1 | 11/2001 | Salerno et al. |
| 6,322,895 B1 | 11/2001 | Canham |
| 6,334,960 B1 | 1/2002 | Wilson et al. |
| 6,380,729 B1 | 4/2002 | Smith |
| 6,403,397 B1 | 6/2002 | Katz |
| 6,413,790 B1 | 6/2002 | Duthaler et al. |
| 6,417,025 B1 | 7/2002 | Gengel |
| 6,420,266 B1 | 7/2002 | Smith et al. |
| 6,433,401 B1 | 8/2002 | Clark et al. |
| 6,451,191 B1 | 9/2002 | Bentsen et al. |
| 6,459,418 B1 | 10/2002 | Comiskey et al. |
| 6,468,638 B2 | 10/2002 | Jacobsen et al. |
| 6,479,395 B1 | 11/2002 | Smith et al. |
| 6,487,906 B1 | 12/2002 | Hock |
| 6,517,995 B1 | 2/2003 | Jacobson et al. |
| 6,555,408 B1 | 4/2003 | Jacobsen et al. |
| 6,527,964 B1 | 5/2003 | Smith et al. |
| 6,559,905 B1 | 5/2003 | Akiyama |
| 6,566,744 B2 | 5/2003 | Gengel |
| 6,580,151 B2 | 6/2003 | Vandeputte et al. |
| 6,586,338 B2 | 7/2003 | Smith et al. |
| 6,590,346 B1 | 7/2003 | Hadley et al. |
| 6,606,079 B1 | 8/2003 | Smith |
| 6,606,247 B2 | 8/2003 | Credelle et al. |
| 6,608,370 B1 | 8/2003 | Chen et al. |
| 6,615,074 B2 | 9/2003 | Mickle et al. |
| 6,623,579 B1 | 9/2003 | Smith et al. |
| 6,639,578 B1 | 10/2003 | Comiskey et al. |
| 6,655,286 B2 | 12/2003 | Rogers |
| 6,657,289 B1 | 12/2003 | Craig et al. |
| 6,661,037 B2 | 12/2003 | Pan et al. |
| 6,665,044 B1 | 12/2003 | Jacobsen et al. |
| 6,666,821 B2 | 12/2003 | Keimel |
| 6,676,600 B1 | 1/2004 | Conero et al. |
| 6,683,663 B1 | 1/2004 | Hadley et al. |
| 6,693,384 B1 | 2/2004 | Vicentini et al. |
| 6,706,402 B2 | 3/2004 | Rueckes et al. |
| 6,720,469 B1 | 4/2004 | Curtis et al. |
| 6,723,576 B2 | 4/2004 | Nozawa et al. |
| 6,730,990 B2 | 5/2004 | Kondo et al. |
| 6,731,353 B1 | 5/2004 | Credelle et al. |
| 6,743,982 B2 | 6/2004 | Biegelsen et al. |

(56) References Cited

U.S. PATENT DOCUMENTS

| | | |
|---|---|---|
| 6,780,696 B1 | 8/2004 | Schatz |
| 6,784,450 B2 | 8/2004 | Pan et al. |
| 6,814,898 B1 | 11/2004 | Deeman et al. |
| 6,816,380 B2 | 11/2004 | Credelle et al. |
| 6,844,673 B1 | 1/2005 | Bernkopf |
| 6,848,162 B2 | 2/2005 | Arneson et al. |
| 6,850,312 B2 | 2/2005 | Jacobsen et al. |
| 6,856,830 B2 | 2/2005 | He |
| 6,863,219 B1 | 3/2005 | Jacobsen et al. |
| 6,864,435 B2 | 3/2005 | Hermanns et al. |
| 6,864,570 B2 | 3/2005 | Smith |
| 6,872,645 B2 | 3/2005 | Duan et al. |
| 6,878,871 B2 | 4/2005 | Scher et al. |
| 6,881,979 B2 | 4/2005 | Starikov et al. |
| 6,887,450 B2 | 5/2005 | Chen et al. |
| 6,900,094 B2 | 5/2005 | Hammond et al. |
| 6,917,061 B2 | 7/2005 | Pan et al. |
| 6,936,181 B2 | 8/2005 | Bulthaup et al. |
| 6,949,199 B1 | 9/2005 | Gauzner et al. |
| 6,949,206 B2 | 9/2005 | Whiteford |
| 6,950,220 B2 | 9/2005 | Abramson et al. |
| 6,984,934 B2 | 1/2006 | Moller et al. |
| 6,989,285 B2 | 1/2006 | Ball |
| 7,029,951 B2 | 4/2006 | Chen et al. |
| 7,033,961 B1 | 4/2006 | Smart et al. |
| 7,067,903 B2 | 6/2006 | Tachibana et al. |
| 7,116,318 B2 | 10/2006 | Amundson et al. |
| 7,132,313 B2 | 11/2006 | O'Connor et al. |
| 7,148,512 B2 | 12/2006 | Leu et al. |
| 7,158,277 B2 | 1/2007 | Berggren et al. |
| 7,169,546 B2 | 1/2007 | Suzuki et al. |
| 7,169,669 B2 | 1/2007 | Blakers et al. |
| 7,170,164 B2 | 1/2007 | Chen et al. |
| 7,186,624 B2 | 3/2007 | Welser et al. |
| 7,190,051 B2 | 3/2007 | Mech et al. |
| 7,195,733 B2 | 3/2007 | Rogers et al. |
| 7,198,190 B2 * | 4/2007 | Juhan .................. E05B 73/0017 235/380 |
| 7,223,609 B2 | 5/2007 | Anvar et al. |
| 7,253,442 B2 | 8/2007 | Huang et al. |
| 7,255,919 B2 | 8/2007 | Sakata et al. |
| 7,291,540 B2 | 11/2007 | Mech et al. |
| 7,374,968 B2 | 5/2008 | Kornlivich et al. |
| 7,425,523 B2 | 9/2008 | Ikemizu et al. |
| 7,521,292 B2 | 4/2009 | Rogers et al. |
| 7,557,367 B2 | 7/2009 | Rogers et al. |
| 7,622,367 B1 | 11/2009 | Nuzzo et al. |
| 7,629,691 B2 | 12/2009 | Roush et al. |
| 7,635,755 B2 | 12/2009 | Kaplan et al. |
| 7,674,882 B2 | 3/2010 | Kaplan et al. |
| 7,700,402 B2 | 4/2010 | Wild et al. |
| 7,704,684 B2 | 4/2010 | Rogers et al. |
| 7,705,280 B2 | 4/2010 | Nuzzo et al. |
| 7,709,961 B2 | 5/2010 | Greenberg et al. |
| 7,727,575 B2 | 6/2010 | Kaplan et al. |
| 7,799,699 B2 | 9/2010 | Nuzzo et al. |
| 7,842,780 B2 | 11/2010 | Kaplan et al. |
| 7,896,807 B2 | 3/2011 | Clancy et al. |
| 7,932,123 B2 | 4/2011 | Rogers et al. |
| 7,943,491 B2 | 5/2011 | Nuzzo et al. |
| 7,972,875 B2 | 7/2011 | Rogers et al. |
| 7,982,296 B2 | 7/2011 | Nuzzo et al. |
| 8,039,847 B2 | 10/2011 | Nuzzo et al. |
| 8,074,890 B2 * | 12/2011 | Duggan ........... G06K 19/07749 235/492 |
| 8,198,621 B2 | 6/2012 | Rogers et al. |
| 8,212,218 B2 | 7/2012 | Cabral, Jr. et al. |
| 8,217,381 B2 | 7/2012 | Rogers et al. |
| 8,367,035 B2 | 2/2013 | Rogers et al. |
| 8,394,706 B2 | 3/2013 | Nuzzo et al. |
| 8,440,546 B2 | 5/2013 | Rogers et al. |
| 8,470,701 B2 | 6/2013 | Rogers et al. |
| 8,519,345 B2 | 8/2013 | Arsalan et al. |
| 8,552,299 B2 | 10/2013 | Rogers et al. |
| 8,562,095 B2 | 10/2013 | Alleyne et al. |
| 8,664,699 B2 | 3/2014 | Nuzzo et al. |
| 8,905,772 B2 | 12/2014 | Rogers et al. |
| 8,934,965 B2 | 1/2015 | Rogers et al. |
| 8,946,683 B2 | 2/2015 | Rogers et al. |
| 9,105,555 B2 | 8/2015 | Rogers et al. |
| 9,117,940 B2 | 8/2015 | Rogers et al. |
| 9,262,759 B2 | 2/2016 | Hanson et al. |
| 9,324,733 B2 | 4/2016 | Rogers et al. |
| 9,450,043 B2 | 9/2016 | Nuzzo et al. |
| 9,496,229 B2 | 11/2016 | Rogers et al. |
| 9,515,025 B2 | 12/2016 | Rogers et al. |
| 9,554,484 B2 | 1/2017 | Rogers et al. |
| 9,601,671 B2 | 3/2017 | Rogers et al. |
| 9,613,911 B2 | 4/2017 | Rogers et al. |
| 9,647,171 B2 | 5/2017 | Rogers et al. |
| 9,761,444 B2 | 9/2017 | Nuzzo et al. |
| 9,768,086 B2 | 9/2017 | Nuzzo et al. |
| 9,825,229 B2 | 11/2017 | Rogers et al. |
| 9,875,974 B2 | 1/2018 | Rogers et al. |
| 9,986,924 B2 | 6/2018 | Rogers et al. |
| 10,029,451 B2 | 7/2018 | Rogers et al. |
| 10,052,066 B2 | 8/2018 | Rogers et al. |
| 10,064,269 B2 | 8/2018 | Rogers et al. |
| 10,143,086 B2 | 11/2018 | Rogers et al. |
| 10,154,592 B2 | 12/2018 | Rogers et al. |
| 10,192,830 B2 | 1/2019 | Rogers et al. |
| 10,204,864 B2 | 2/2019 | Rogers et al. |
| 10,333,069 B2 | 6/2019 | Rogers et al. |
| 10,355,113 B2 | 7/2019 | Rogers et al. |
| 10,374,072 B2 | 8/2019 | Nuzzo et al. |
| 10,497,633 B2 | 12/2019 | Rogers et al. |
| 10,617,300 B2 | 4/2020 | Rogers et al. |
| 10,667,647 B2 * | 6/2020 | Budd ................... A47J 37/046 |
| 2001/0003043 A1 | 6/2001 | Metspalu et al. |
| 2001/0025917 A1 | 10/2001 | Asada et al. |
| 2002/0004251 A1 | 1/2002 | Roberts et al. |
| 2002/0021445 A1 | 2/2002 | Boxhevolnyi et al. |
| 2002/0087436 A1 * | 7/2002 | Guthrie ................ G01D 4/004 705/28 |
| 2002/0110766 A1 | 8/2002 | Tsai et al. |
| 2003/0006527 A1 | 1/2003 | Rabolt et al. |
| 2003/0032892 A1 | 2/2003 | Erlach et al. |
| 2003/0082889 A1 | 5/2003 | Maruyama et al. |
| 2003/0087476 A1 | 5/2003 | Oohata et al. |
| 2003/0138704 A1 | 7/2003 | Mei et al. |
| 2003/0149456 A1 | 8/2003 | Rottenberg et al. |
| 2003/0178316 A1 | 9/2003 | Jacobs et al. |
| 2003/0222282 A1 | 12/2003 | Fjelstad et al. |
| 2003/0227116 A1 | 12/2003 | Halik et al. |
| 2004/0005723 A1 | 1/2004 | Empedocles et al. |
| 2004/0026684 A1 | 2/2004 | Empedocles et al. |
| 2004/0079464 A1 | 4/2004 | Kumakura |
| 2004/0081384 A1 | 4/2004 | Datesman et al. |
| 2004/0095658 A1 | 5/2004 | Buretea et al. |
| 2004/0112964 A1 | 6/2004 | Empedocles et al. |
| 2004/0136866 A1 | 7/2004 | Pontis et al. |
| 2004/0146560 A1 | 7/2004 | Whiteford et al. |
| 2004/0155290 A1 | 8/2004 | Mech et al. |
| 2004/0178390 A1 | 9/2004 | Whiteford |
| 2004/0178913 A1 | 9/2004 | Penuela et al. |
| 2004/0192082 A1 | 9/2004 | Wagner et al. |
| 2004/0114459 A1 | 10/2004 | Suenaga et al. |
| 2004/0200734 A1 | 10/2004 | Co et al. |
| 2004/0206448 A1 | 10/2004 | Dubrow |
| 2004/0211458 A1 | 10/2004 | Gui et al. |
| 2004/0242976 A1 | 12/2004 | Abreu |
| 2004/0250950 A1 | 12/2004 | Dubrow |
| 2004/0252559 A1 | 12/2004 | Gupta |
| 2005/0020094 A1 | 1/2005 | Forbes et al. |
| 2005/0233546 A1 | 1/2005 | Oohata et al. |
| 2005/0038498 A1 | 2/2005 | Dubrow et al. |
| 2005/0082526 A1 | 4/2005 | Bedell et al. |
| 2005/0096513 A1 * | 5/2005 | Ozguz .................. H01L 21/6836 600/301 |
| 2005/0124712 A1 | 6/2005 | Anderson et al. |
| 2005/0133954 A1 | 6/2005 | Homola |
| 2005/0212007 A1 | 9/2005 | Daniels et al. |
| 2005/0214962 A1 | 9/2005 | Daniels et al. |
| 2005/0227389 A1 | 10/2005 | Bhattacharya et al. |

(56) References Cited

U.S. PATENT DOCUMENTS

| | | |
|---|---|---|
| 2005/0238967 A1 | 10/2005 | Rogers et al. |
| 2005/0255686 A1 | 11/2005 | Yamano et al. |
| 2005/0260706 A1 | 11/2005 | Kaplan et al. |
| 2005/0261561 A1 | 11/2005 | Jones et al. |
| 2006/0038182 A1 | 2/2006 | Rogers et al. |
| 2006/0049485 A1 | 3/2006 | Pan et al. |
| 2006/0084012 A1 | 4/2006 | Nuzzo et al. |
| 2006/0085976 A1 | 4/2006 | Eldridge et al. |
| 2006/0102525 A1 | 5/2006 | Volkel et al. |
| 2006/0119853 A1 | 6/2006 | Baumberg et al. |
| 2006/0127817 A1 | 6/2006 | Ramanujan et al. |
| 2006/0129056 A1 | 6/2006 | Leuthardt et al. |
| 2006/0132025 A1 | 6/2006 | Gao et al. |
| 2006/0134893 A1 | 6/2006 | Savage et al. |
| 2006/0159837 A1 | 7/2006 | Kaplan et al. |
| 2006/0164252 A1 | 7/2006 | Richmond |
| 2006/0169989 A1 | 8/2006 | Bhatacharya |
| 2006/0173364 A1 | 8/2006 | Clancy et al. |
| 2006/0177479 A1 | 8/2006 | Giachelli et al. |
| 2006/0178655 A1 | 8/2006 | Santini et al. |
| 2006/0244105 A1 | 11/2006 | Forbes et al. |
| 2006/0248478 A1 | 11/2006 | Liau |
| 2006/0255341 A1 | 11/2006 | Pinnington et al. |
| 2006/0273279 A1 | 12/2006 | Kaplan et al. |
| 2006/0279191 A1 | 12/2006 | Gehegan et al. |
| 2006/0286488 A1 | 12/2006 | Rogers et al. |
| 2006/0286785 A1 | 12/2006 | Rogers et al. |
| 2007/0009968 A1 | 1/2007 | Cunningham et al. |
| 2007/0031607 A1 | 2/2007 | Dubson et al. |
| 2007/0032089 A1 | 2/2007 | Nuzzo et al. |
| 2007/0043416 A1 | 2/2007 | Callas et al. |
| 2007/0058254 A1 | 3/2007 | Kim |
| 2007/0073130 A1 | 3/2007 | Finch et al. |
| 2007/0123963 A1 | 5/2007 | Krulevitch |
| 2007/0187862 A1 | 8/2007 | Kaplan et al. |
| 2007/0212730 A1 | 9/2007 | Vepari et al. |
| 2007/0227586 A1 | 10/2007 | Zapalac |
| 2007/0233208 A1 | 10/2007 | Kurtz et al. |
| 2007/0257821 A1 | 11/2007 | Son et al. |
| 2008/0038236 A1 | 2/2008 | Gimble et al. |
| 2008/0055581 A1 | 3/2008 | Rogers et al. |
| 2008/0085272 A1 | 4/2008 | Kaplan et al. |
| 2008/0090322 A1 | 4/2008 | Mech et al. |
| 2008/0102096 A1 | 5/2008 | Molin et al. |
| 2008/0108171 A1 | 5/2008 | Rogers et al. |
| 2008/0152281 A1 | 6/2008 | Lundquist et al. |
| 2008/0000871 A1 | 7/2008 | Suh et al. |
| 2008/0157235 A1 | 7/2008 | Rogers et al. |
| 2008/0183076 A1 | 7/2008 | Witte et al. |
| 2008/0203431 A1 | 8/2008 | Garcia et al. |
| 2008/0212102 A1 | 9/2008 | Nuzzo et al. |
| 2008/0239755 A1 | 10/2008 | Parker et al. |
| 2008/0280360 A1 | 11/2008 | Kaplan et al. |
| 2008/0288037 A1 | 11/2008 | Neysmith et al. |
| 2008/0293919 A1 | 11/2008 | Kaplan et al. |
| 2009/0004737 A1 | 1/2009 | Borenstein et al. |
| 2009/0012533 A1 | 1/2009 | Barbagli et al. |
| 2009/0028910 A1 | 1/2009 | Desimone et al. |
| 2009/0040037 A1 | 2/2009 | Schraga |
| 2009/0078990 A1 | 3/2009 | Yasuda |
| 2009/0085214 A1 | 4/2009 | Wada et al. |
| 2009/0114832 A1 | 5/2009 | Lynn et al. |
| 2009/0149930 A1 | 6/2009 | Schecnk |
| 2009/0198293 A1 | 8/2009 | Cauller et al. |
| 2009/0199960 A1 | 8/2009 | Nuzzo et al. |
| 2009/0202614 A1 | 8/2009 | Kaplan et al. |
| 2009/0208555 A1 | 8/2009 | Kuttler et al. |
| 2009/0221896 A1 | 9/2009 | Rickert et al. |
| 2009/0232963 A1 | 9/2009 | Kaplan et al. |
| 2009/0234026 A1 | 9/2009 | Kaplan et al. |
| 2009/0289246 A1 | 11/2009 | Schneider et al. |
| 2009/0293664 A1 | 12/2009 | Aabloo et al. |
| 2009/0294803 A1 | 12/2009 | Nuzzo et al. |
| 2010/0002402 A1 | 1/2010 | Rogers et al. |
| 2010/0028451 A1 | 2/2010 | Kaplan et al. |
| 2010/0046902 A1 | 2/2010 | Kaplan et al. |
| 2010/0052112 A1 | 3/2010 | Rogers et al. |
| 2010/0055438 A1 | 3/2010 | Kaplan et al. |
| 2010/0059863 A1 | 3/2010 | Rogers et al. |
| 2010/0063404 A1 | 3/2010 | Kaplan et al. |
| 2010/0065784 A1 | 3/2010 | Kaplan et al. |
| 2010/0068740 A1 | 3/2010 | Kaplan et al. |
| 2010/0070068 A1 | 3/2010 | Kaplan et al. |
| 2010/0072577 A1 | 3/2010 | Nuzzo et al. |
| 2010/0096763 A1 | 4/2010 | Kaplan et al. |
| 2010/0120116 A1 | 5/2010 | Kaplan et al. |
| 2010/0121420 A1 | 5/2010 | Fiset et al. |
| 2010/0141407 A1 | 6/2010 | Heubel et al. |
| 2010/0178304 A1 | 7/2010 | Wang et al. |
| 2010/0191328 A1 | 7/2010 | Kaplan et al. |
| 2010/0196447 A1 | 8/2010 | Kaplan et al. |
| 2010/0200752 A1 | 8/2010 | Lee et al. |
| 2010/0203226 A1 | 8/2010 | Kaplan et al. |
| 2010/0238636 A1 | 9/2010 | Mascaro et al. |
| 2010/0279112 A1 | 11/2010 | Kaplan et al. |
| 2010/0283069 A1 | 11/2010 | Rogers et al. |
| 2010/0289124 A1 | 11/2010 | Nuzzo et al. |
| 2010/0317132 A1 | 12/2010 | Rogers et al. |
| 2011/0071439 A1 | 3/2011 | Bach-y-Rita et al. |
| 2011/0129158 A1 | 6/2011 | Sato |
| 2011/0147715 A1 | 6/2011 | Rogers et al. |
| 2011/0168403 A1 | 7/2011 | Patel |
| 2011/0170225 A1 | 7/2011 | Rogers et al. |
| 2011/0171813 A1 | 7/2011 | Rogers et al. |
| 2011/0187798 A1 | 8/2011 | Rogers et al. |
| 2011/0220890 A1 | 9/2011 | Nuzzo et al. |
| 2011/0230747 A1 | 9/2011 | Rogers et al. |
| 2011/0254665 A1 | 10/2011 | Lindsay et al. |
| 2011/0266561 A1 | 11/2011 | Rogers et al. |
| 2011/0276112 A1 | 11/2011 | Simon et al. |
| 2011/0277813 A1 | 11/2011 | Rogers et al. |
| 2011/0316120 A1 | 12/2011 | Rogers et al. |
| 2012/0157804 A1 | 6/2012 | Rogers et al. |
| 2012/0165759 A1 | 6/2012 | Rogers et al. |
| 2012/0261551 A1 | 10/2012 | Rogers et al. |
| 2012/0320581 A1 | 12/2012 | Rogers et al. |
| 2012/0327608 A1 | 12/2012 | Rogers et al. |
| 2013/0018742 A1 | 1/2013 | Fisher |
| 2013/0036928 A1 | 2/2013 | Rogers et al. |
| 2013/0041235 A1 | 2/2013 | Rogers et al. |
| 2013/0070805 A1 | 3/2013 | Coln et al. |
| 2013/0072775 A1 | 3/2013 | Rogers et al. |
| 2013/0100618 A1 | 4/2013 | Rogers et al. |
| 2013/0140649 A1 | 6/2013 | Rogers et al. |
| 2013/0200268 A1 | 8/2013 | Rafferty et al. |
| 2014/0034815 A1 | 2/2014 | Lai et al. |
| 2014/0263989 A1 | 9/2014 | Valentino et al. |
| 2014/0264047 A1 | 9/2014 | Valentino et al. |
| 2014/0268601 A1 | 9/2014 | Valentino et al. |
| 2014/0326791 A1 | 11/2014 | Ishida et al. |
| 2015/0022814 A1 | 1/2015 | Kousalik et al. |
| 2015/0080695 A1 | 3/2015 | Rogers et al. |
| 2015/0085893 A1 | 3/2015 | Zhang et al. |
| 2015/0094914 A1 | 4/2015 | Abreu |
| 2015/0102208 A1 | 4/2015 | Appelboom et al. |
| 2015/0112169 A1 | 4/2015 | Lamego et al. |
| 2015/0141767 A1 | 5/2015 | Rogers et al. |
| 2015/0237711 A1 | 8/2015 | Rogers et al. |
| 2015/0335254 A1 | 11/2015 | Fastert et al. |
| 2015/0373831 A1 | 12/2015 | Rogers et al. |
| 2016/0050750 A1 | 2/2016 | Rogers et al. |
| 2016/0064814 A1 | 3/2016 | Jang et al. |
| 2016/0136877 A1 | 5/2016 | Rogers et al. |
| 2017/0020402 A1 | 1/2017 | Rogers et al. |
| 2017/0128015 A1 | 5/2017 | Rogers et al. |
| 2017/0133751 A1 | 5/2017 | Noh et al. |
| 2017/0179085 A1 | 6/2017 | Rogers et al. |
| 2017/0179100 A1 | 6/2017 | Rogers et al. |
| 2017/0179356 A1 | 6/2017 | Rogers et al. |
| 2017/0200707 A1 | 7/2017 | Rogers et al. |
| 2017/0224257 A1 | 8/2017 | Rogers |
| 2017/0231571 A1 | 8/2017 | Rogers et al. |
| 2017/0347891 A1 | 12/2017 | Rogers et al. |
| 2018/0014734 A1 | 1/2018 | Rogers et al. |

(56) References Cited

U.S. PATENT DOCUMENTS

| | | |
|---|---|---|
| 2018/0064377 A1 | 3/2018 | Rogers et al. |
| 2018/0165566 A1 | 6/2018 | Rogers et al. |
| 2018/0175158 A1 | 6/2018 | Rogers et al. |
| 2018/0192952 A1 | 7/2018 | Rogers et al. |
| 2018/0274973 A1 | 9/2018 | Rogers et al. |
| 2018/0286820 A1 | 10/2018 | Rogers et al. |
| 2018/0303418 A1 | 10/2018 | Rogers et al. |
| 2018/0359850 A1 | 12/2018 | Rogers et al. |
| 2019/0053712 A1 | 2/2019 | Rogers et al. |
| 2019/0090801 A1 | 3/2019 | Rogers et al. |
| 2019/0369728 A1 | 12/2019 | Rogers et al. |
| 2020/0006540 A1 | 1/2020 | Nuzzo et al. |
| 2020/0013720 A1 | 1/2020 | Rogers et al. |
| 2020/0022601 A1 | 1/2020 | Rogers et al. |
| 2020/0088739 A1 | 3/2020 | Rogers et al. |
| 2020/0093416 A1 | 3/2020 | Rogers et al. |
| 2020/0129077 A1 | 4/2020 | Rogers et al. |
| 2020/0155047 A1 | 5/2020 | Rogers et al. |
| 2020/0161291 A1 | 5/2020 | Rogers et al. |
| 2020/0315488 A1 | 10/2020 | Rogers et al. |
| 2020/0345279 A1 | 11/2020 | Rogers et al. |

FOREIGN PATENT DOCUMENTS

| | | |
|---|---|---|
| WO | WO 99/045860 | 9/1999 |
| WO | WO 00/046854 | 8/2000 |
| WO | WO 00/049421 | 8/2000 |
| WO | WO 00/049658 | 8/2000 |
| WO | WO 00/055915 | 9/2000 |
| WO | WO 00/055916 | 9/2000 |
| WO | WO 01/031082 | 5/2001 |
| WO | WO 01/033621 | 5/2001 |
| WO | WO 01/066833 | 9/2001 |
| WO | WO 01/098838 | 12/2001 |
| WO | WO 02/027701 | 4/2002 |
| WO | WO 02/043032 | 5/2002 |
| WO | WO 02/073699 | 9/2002 |
| WO | WO 02/092778 | 11/2002 |
| WO | WO 02/097724 | 12/2002 |
| WO | WO 2004/099068 | 12/2002 |
| WO | WO 03/030194 | 4/2003 |
| WO | WO 03/032240 | 4/2003 |
| WO | WO 03/049201 | 6/2003 |
| WO | WO 03/063211 | 7/2003 |
| WO | WO 03/085700 | 10/2003 |
| WO | WO 03/085701 | 10/2003 |
| WO | WO 03/092073 | 11/2003 |
| WO | WO 04/000915 | 12/2003 |
| WO | WO 04/001103 | 12/2003 |
| WO | WO 04/003535 | 1/2004 |
| WO | WO 04/022637 | 3/2004 |
| WO | WO 04/022714 | 3/2004 |
| WO | WO 04/023527 | 3/2004 |
| WO | WO 04/024407 | 3/2004 |
| WO | WO 04/027822 | 4/2004 |
| WO | WO 2004/032190 | 4/2004 |
| WO | WO 2004/032191 | 4/2004 |
| WO | WO 2004/032193 | 4/2004 |
| WO | WO 2004/034025 | 4/2004 |
| WO | WO 2004/062697 | 7/2004 |
| WO | WO 2004/086289 | 10/2004 |
| WO | WO 2004/094303 | 11/2004 |
| WO | WO 2004/100252 | 11/2004 |
| WO | WO 2004/105456 | 12/2004 |
| WO | WO 2005/000483 | 1/2005 |
| WO | WO 2005/005679 | 1/2005 |
| WO | WO 2005/012606 | 2/2005 |
| WO | WO 2005/015480 | 2/2005 |
| WO | WO 2005/017962 | 2/2005 |
| WO | WO 2005/022120 | 3/2005 |
| WO | WO 2005/029578 | 3/2005 |
| WO | WO 2005/054119 | 6/2005 |
| WO | WO 2005/104756 | 11/2005 |
| WO | WO 02/097708 | 12/2005 |
| WO | WO 2005/122285 | 12/2005 |
| WO | WO 2005/123114 | 12/2005 |
| WO | WO 2006/028996 | 3/2006 |
| WO | WO 2006/042287 | 4/2006 |
| WO | WO 2006/076711 | 7/2006 |
| WO | WO 2006/104069 | 10/2006 |
| WO | WO 2006/130721 | 12/2006 |
| WO | WO 2007/000037 | 1/2007 |
| WO | WO 2007/016524 | 2/2007 |
| WO | WO 2007/028003 | 3/2007 |
| WO | WO 2007/056183 | 5/2007 |
| WO | WO 2007/126412 | 11/2007 |
| WO | WO 2008/030666 | 3/2008 |
| WO | WO 2008/030960 | 3/2008 |
| WO | WO 2008/036837 | 3/2008 |
| WO | WO 2008/055054 | 5/2008 |
| WO | WO 2008/085904 | 7/2008 |
| WO | WO 2008/103464 | 8/2008 |
| WO | WO 2008/106485 | 9/2008 |
| WO | WO 2008/108838 | 9/2008 |
| WO | WO 2008/118133 | 10/2008 |
| WO | WO 2008/118211 | 10/2008 |
| WO | WO 2008/127401 | 10/2008 |
| WO | WO 2008/127402 | 10/2008 |
| WO | WO 2008/127403 | 10/2008 |
| WO | WO 2008/127404 | 10/2008 |
| WO | WO 2008/127405 | 10/2008 |
| WO | WO 2008/140562 | 11/2008 |
| WO | WO 2008/143635 | 11/2008 |
| WO | WO 2008/150861 | 12/2008 |
| WO | WO 2009/011709 | 1/2009 |
| WO | WO 2009/023615 | 2/2009 |
| WO | WO 2009/061823 | 5/2009 |
| WO | WO 2009/075625 | 6/2009 |
| WO | WO 2009/076088 | 6/2009 |
| WO | WO 2009/090398 | 7/2009 |
| WO | WO 2009/100280 | 8/2009 |
| WO | WO 2009/111641 | 9/2009 |
| WO | WO 2009/114115 | 9/2009 |
| WO | WO 2009/114689 | 9/2009 |
| WO | WO 2009/118678 | 10/2009 |
| WO | WO 2009/126689 | 10/2009 |
| WO | WO 2009/140588 | 11/2009 |
| WO | WO 2009/155397 | 12/2009 |
| WO | WO 2010/005707 | 1/2010 |
| WO | WO 2010/036807 | 4/2010 |
| WO | WO 2010/036992 | 4/2010 |
| WO | WO 2010/040528 | 4/2010 |
| WO | WO 2010/042798 | 4/2010 |
| WO | WO 2010/049881 | 5/2010 |
| WO | WO 2010/057142 | 5/2010 |
| WO | WO 2010/065957 | 6/2010 |
| WO | WO 2010/081989 | 7/2010 |
| WO | WO 2010/126640 | 11/2010 |
| WO | WO 2010/132552 | 11/2010 |
| WO | WO 2010/141133 | 12/2010 |
| WO | WO 2011/005381 | 1/2011 |
| WO | WO 2011/006133 | 1/2011 |
| WO | WO 2011/008842 | 1/2011 |
| WO | WO 2011/011347 | 1/2011 |
| WO | WO 2011/026101 | 3/2011 |
| WO | WO 2011/038401 | 3/2011 |
| WO | WO 2011/041395 | 4/2011 |
| WO | WO 2011/046652 | 4/2011 |
| WO | WO 2011/084450 | 7/2011 |
| WO | WO 2011/112931 | 9/2011 |
| WO | WO 2011/115643 | 9/2011 |
| WO | WO 2012/167096 | 12/2012 |
| WO | WO 2013/010113 | 1/2013 |
| WO | WO 2013/089867 | 6/2013 |
| WO | WO 2013/149181 | 10/2013 |
| WO | WO 2014/032193 | 3/2014 |
| WO | WO 2014/169170 | 10/2014 |
| WO | WO 2014/169218 | 10/2014 |
| WO | WO 2015/051085 | 4/2015 |
| WO | WO 2017/173339 | 10/2017 |
| WO | WO 2017/218878 | 12/2017 |
| WO | WO 2018/140693 | 8/2018 |
| WO | WO 2018/140743 | 8/2018 |
| WO | WO 2018/209100 | 11/2018 |

(56) References Cited

FOREIGN PATENT DOCUMENTS

| WO | WO 2018/223033 | 12/2018 |
|----|----------------|---------|
| WO | WO 2018/223044 | 12/2018 |
| WO | WO 2018/223058 | 12/2018 |
| WO | WO 2018/223090 | 12/2018 |
| WO | WO 2019/161277 | 8/2019 |
| WO | WO 2019/165219 | 8/2019 |
| WO | WO 2019/191693 | 10/2019 |
| WO | WO 2019/191703 | 10/2019 |
| WO | WO 2019/222605 | 11/2019 |
| WO | WO 2020/092747 | 5/2020 |
| WO | WO 2020/092764 | 5/2020 |
| WO | WO 2020/092786 | 5/2020 |

OTHER PUBLICATIONS

Australian Exam Report, dated Sep. 4, 2020, corresponding to Australian Patent Application No. 2016270805, 4 pp.
Australian Exam Report, dated Sep. 21, 2020, corresponding to Australian Patent Application No. 2016270807, 3 pp.
AZoSensors (2013) "LED Light Sensors," AZoNetwork; Available online at https://www.azosensors.com/article.aspx?ArticleID=329, Accessed Apr. 10, 2020: 3 pp.
Bean "Nail Growth: Thirty-five Years of Observation," Arch Intern Med, 1980, 140(1):73-76.
Brazilian Office Action, dated May 20, 2020, corresponding to Brazilian Patent Application No. 112017025616-9, 5 pp.
Chinese First Office Action with English translation, dated Jul. 3, 2019, in Chinese Patent Application No. 201680045183.6, 19 pp.
Chinese Second Office Action with English translation, dated Apr. 22, 2020, in Chinese Patent Application No. 201680045183.6, 19 pp.
Dangerous Things (2014) "The xNT implantable NFC chip," Retrieved Mar. 15, 2014, from http: //www.indiegogo.com/projects/the-xnt-implantable-nfc-chip.
European Supplemental Search Report, dated Jan. 31, 2019, corresponding to European Application No. 16804361.0, a related application, 8 pp.
European Examination Report, dated Aug. 6, 2019, in European Patent Application No. 16804359.4, 5 pp.
European Supplemental Search Report, dated Oct. 31, 2018, corresponding to European Application No. 16804359.4, a related application, 9 pp.
European Office Action, dated Apr. 24, 2020, corresponding to European Patent Application No. 16804361.0, 5 pp.
European Office Action, dated May 14, 2020, corresponding to European Patent Application No. 16804359.4, 5 pp.
Fitzpatrick "The Validity and Practicality of Sun-Reactive Skin Types I Through VI," Arch. Dermatol., 1988 124(6):869-871.
Freudenthal et al. "Suitability of NFC for Medical Device Communication and Power Delivery," IEEE Dallas Engineering in Medicine and Biology Workshop, 2007:51-54.
Gao et al. "Epidermal photonic devices for quantitative imaging of temperature and thermal transport characteristics of the skin," Nature Communications, Sep. 2014, 5:4938. (10 pp.).
Harpster et al. "A passive wireless integrated humidity sensor," Sensor Actuat a-Phys, 2002, 95: 100-107.
Huang et al. "Materials and Designs for Wireless Epidermal Sensors of Hydration and Strain," Adv Funct Mater, Mar. 2014, 24: 3846-3854.
Huang et al. "Stretchable, Wireless Sensors and Functional Substrates for Epidermal Characterization of Sweat," Small, Apr. 2014, 10(15):3083-3090.
Jang et al. "Soft network composite materials with deterministic and bio-inspired designs," Nature Commun, Mar. 2015, 6:6566. (11 pp.).
Jeong et al. "Materials and Optimized Designs for Human-Machine Interfaces Via Epidermal Electronics," Adv Mater, 2013, 25(47):6839. (21 pp.).

Kim et al. "Epidermal Electronics," Science, 2011, 333:838-843. (Additional supporting material 39 pp.).
Kim et al. "Flexible and Stretchable Electronics for Biointegrated Devices," Annu. Rev. Biomed. Eng., 2012, 14:113-128.
Kim et al. "Epidermal Electronics with Advanced Capabilities in Near-Field Communication," Small, Feb. 2015, 11(8):906-912.
"LED Circuit," last edited Jan. 2020, Wikipedia, available online at https://en.wikipedia.org/wiki/LED_circuit#LED_as_light_sensor, 6 pp.
Lu et al. "Delamination of stiff islands patterned on stretchable substrates," Int J Mater Res, 2007, 98(8):717-722.
Marian (2012) "LED as Light Detector," Electro Schematics; Available online at https://www.electroschematics.com/led-as-light-detector/, Accessed Apr. 10, 2020: 7 pp.
Mims (2013) "How to Use LEDs to Detect Light," makezine.com, retrieved from the Internet Archive Wayback Machine, 4 pp.
Murdan "Transverse fingernail curvature in adults: a quantitative evaluation and the influence of gender, age, and hand size and dominance," Int J Cosmetic Sci, 2011, 33:509-513. (17 pp.).
Raupp "(Invited) Flexible Thin Film Transistor Arrays as an Enabling Platform Technology: Opportunities and Challenges," Ecs Transactions 2011, 37(1):229-240.
Rose et al. "Adhesive RFID Sensor Patch for Monitoring of Sweat Electrolytes," IEEE Transactions on Biomedical Engineering, Jun. 2015, 62(6): 1457-1465.
Saeed et al. "Off-line NFC Tag Authentication," The 7th International Conference for Internet Technology and Secured Transactions, 2012, 730-735.
Search Report and Written Opinion, dated Oct. 24, 2016, corresponding to International Application No. PCT/US2016/035331 (filed Jun. 1, 2016), 13 pp.
Search Report and Written Opinion, dated Oct. 11, 2016, corresponding to International Application No. PCT/US2016/035336 (filed Jun. 1, 2016), 12 pp.
Sidén et al. "Home care with NFC sensors and a smart phone", Proceedings of the 4th International Symposium on Applied Sciences in Biomedical and Communication Technologies, 2011, 5 pages.
USPTO "Non-Final Office Action," dated Oct. 12, 2018, in U.S. Appl. No. 15/578,602, 8 pp.
USPTO Office Action, dated Apr. 25, 2019, in U.S. Appl. No. 15/578,617, 7 pp.
USPTO "Final Office Action," dated Jun. 6, 2019, in U.S. Appl. No. 15/578,602, 8 pp.
USPTO "Non-Final Office Action," dated Sep. 17, 2019, in U.S. Appl. No. 15/578,602, 7 pp.
USPTO "Non-Final Office Action," dated Sep. 19, 2019, in U.S. Appl. No. 15/578,617, 27 pp.
USPTO "Notice of Allowance," dated Jan. 29, 2020, in U.S. Appl. No. 15/578,602, 8 pp.
USPTO "Final Office Action," dated Mar. 18, 2020, in U.S. Appl. No. 15/578,617, 24 pp.
USPTO "Non-Final Office Action," dated Aug. 4, 2020, in U.S. Appl. No. 15/578,617, 27 pp.
Wang et al. "Mechanics of Epidermal Electronics," J Appl Mech-T Asme, 2012, 79: 031022-1-031022-6.
Windmiller et al. "Electrochemical Sensing Based on Printable Temporary Transfer Tattoos," Chem Commun, 2012, 48(54):6794-6796.
Windmiller et al. "Wearable Electrochemical Sensors and Biosensors: A Review," Electroanalysis, 2013, 25(1): 29-46.
Xu et al. "Soft Microfluidic Assemblies of Sensors, Circuits, and Radios for the Skin," Science, Apr. 2014, 344(6179):70-74.
Zeng et al. "Fiber-Based Wearable Electronics: A Review of Materials, Fabrication, Devices, and Applications," Adv. Mater., Jun. 2014, 26:5310-5336.
Žnidaršič et al. "Adoption of RFID microchip for eHealth according to eActivities of potential users," BLED 2014 Proceedings, Jun. 2014, 16:1-14.

\* cited by examiner

Size : < 8 mm diameter (down to ~5 mm)
Thickness : ~50 μm (coils), ~100 μm (chips)

Fingernail Authentication Device Designs
Ultra Small Authentication Device
With Energy Harvesting LED indicator
~6.4 mm
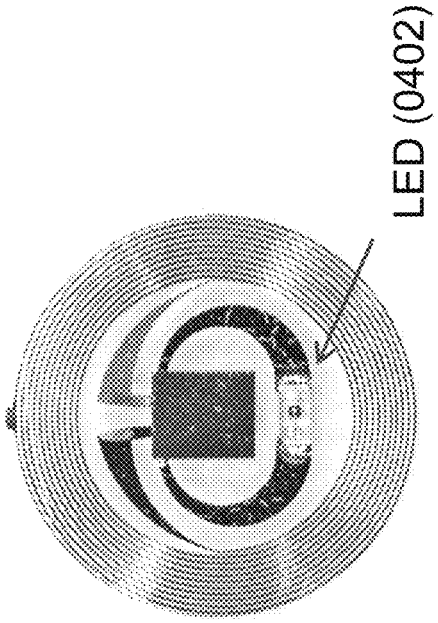
LED (0402)
ST-M24LR04E (27 pF internal cap.)
1.7 mm x 1.5 mm (energy harvesting)
Ultra Small Authentication Device
~5 mm
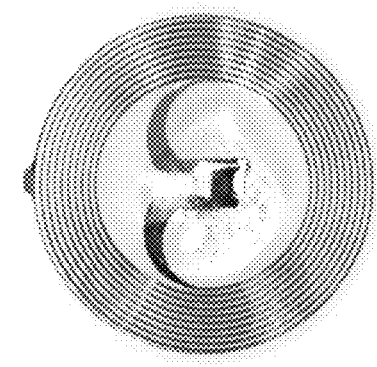
NXP216 (50 pF internal cap.)
0.7 mm x 0.5 mm
FIG. 11

Fingernail mounted NFC tag

Demo with special mouse

Photo

Movie (click)

In addition to your cell phone a computer mouse equipped with an NFC reader can be used with the fingernail NFC device to Authentic your desktop PC

P ASSWORD
A UTHENTICATION
C ONFIRMATION
I LLUMINATION

Hospital/Clinic

Ultraminiaturized, Washable RFID tags

These ultraminiaturized devices can be used for many applications including logging time and intervals of handwashing prior and post-surgical procedures. Convenient and secure critical access control/authentication (rooms, cabinets, equipment). The devices remain sanitary by being washed with the hands while maintaining secure attachment. The device can be read conveniently without removing PPE such as surgical gloves. A key advantage over bracelets or other RFID tags is that these devices are ~100x smaller, and can be washed to avoid contaminating the sterile field.

Skin or Nail Mounted Sensors of Exposure in UV Phototherapy

Skin or nail plate mounted, thin, miniature UV radiation sensors continuously monitor exposure to UV and/or low range visible radiation. Applications include total dose under bilirubin lights, patients receiving various other light therapy in treatment of skin disorders as with psoriasis, vitiligo, scleroderma, morphea and cutaneous graft-versus-host disease (GVHD).

Epidermal Electronic Monitors for NICU Isolettes

These ultrathin, skin-like wireless reading units gently laminate onto the skin of the patient, where they record and transmit vital information (core body temperature, ECG, heart rate, blood ox) continuously, and other information (patient's time spent in/out of the isolette). The primary advantage is in elimination of wired connections and in elimination of skin irritation.

Fig. 21

Ultraminiaturized, UV Sensors

Skin or Nail Mounted Sensors of Exposure in UV Phototherapy
Monitor optical dose UV-B therapy, used to treat psoriasis, atopic dermatitis (eczema), vitiligo (loss of skin color) and some other skin diseases.

UV-A treatment for skin problems such as psoriasis, eczema, vitiligo UV-A light is applied most commonly to persistent problems with hands and feet.

Phototherapy in the NICU

Under the protective layer for monitoring

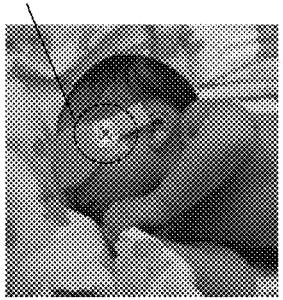
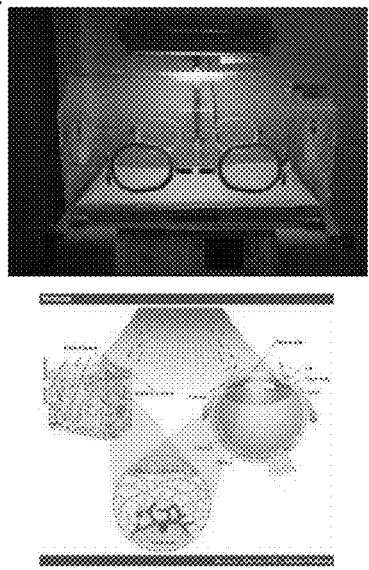
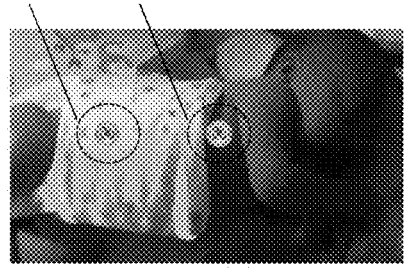

Monitor optical dose

Blue-light exposure of cutaneous and uveal melanocytes during phototherapy. Ocular melanocytes consist of two different cell types: conjunctival and uveal melanocytes. Uveal melanocytes reside in the middle layer of the eyeball: in the iris, the ciliary body and the choroid. Conjunctival melanocytes are located in the conjunctiva (thin layers of epithelium and underlying connective tissue covering the anterior surface of the sclera and the posterior surface of the eyelids).

Fig. 24

Infectious Disease Compliance

Infectious Disease Compliance

- The Association for Professionals in Infection Control and Epidemiology, Inc.
- The Centers for Disease Control and Prevention
- The Institute for Healthcare Improvement
- The National Foundation for Infectious Diseases
- The Society for Healthcare Epidemiology of America
- The World Health Organization World Alliance for Patient Safety

Measuring Product Use

Measuring the amount of liquid soap, alcohol-based hand rub, and paper towels that health care workers use—and measuring the frequency with which they use these products—is an indirect way of estimating staff adherence to hand hygiene guidelines. Measuring product use is less

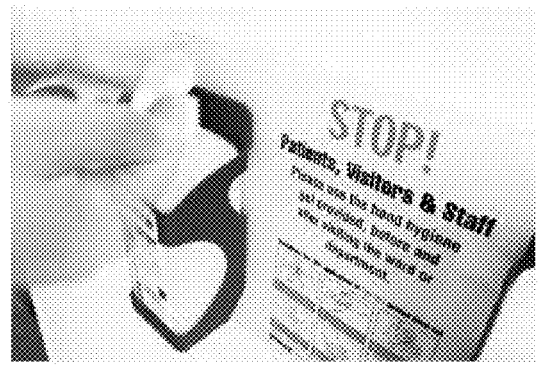

On the other hand, measuring product use does not reveal whether health care workers are performing hand hygiene when it is indicated or whether they are performing it correctly. Measuring product use does not yield any con-

Fig. 26

Monitoring solution

Pulse oximetry and Colorimeter

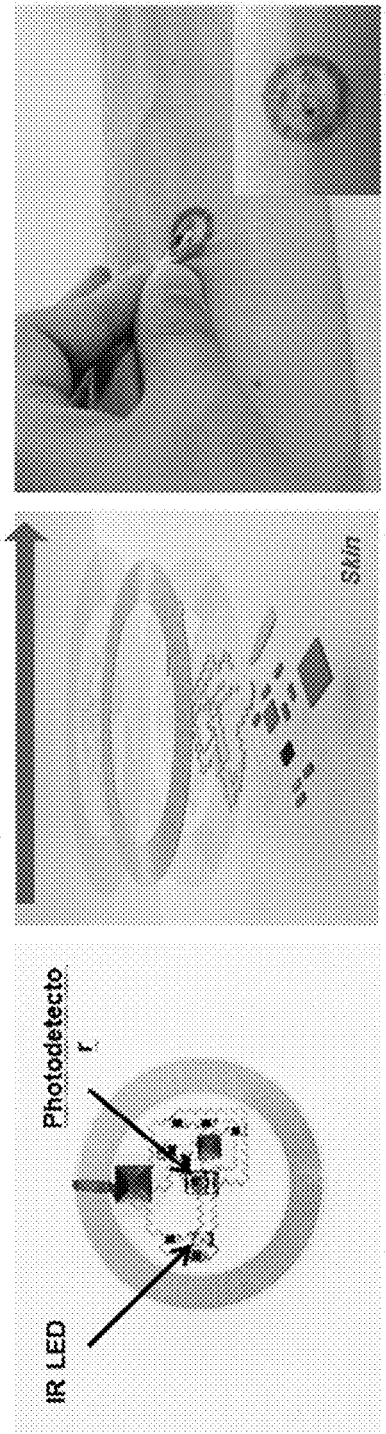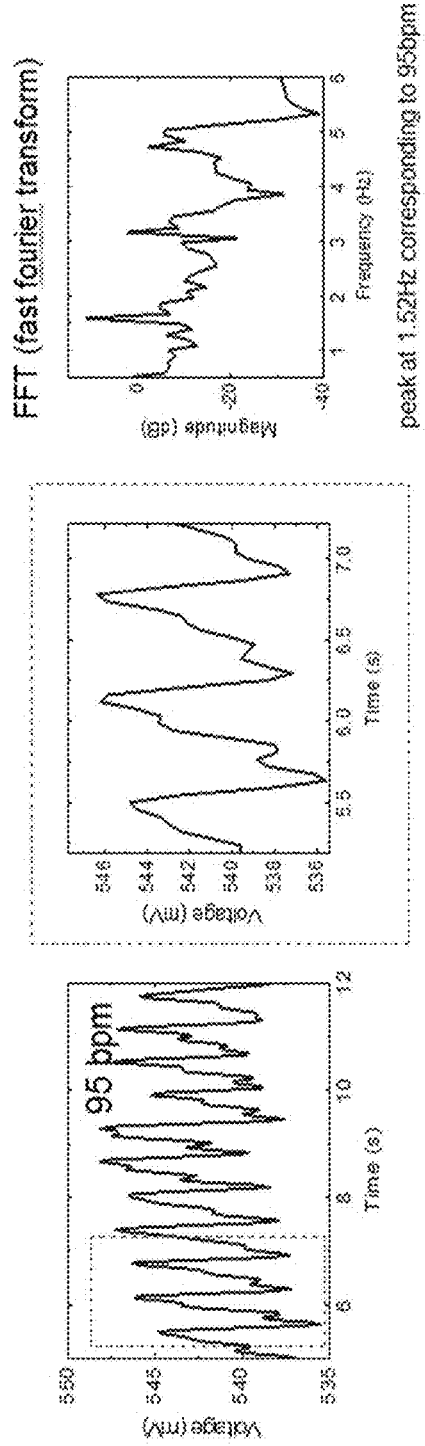
Fig. 29

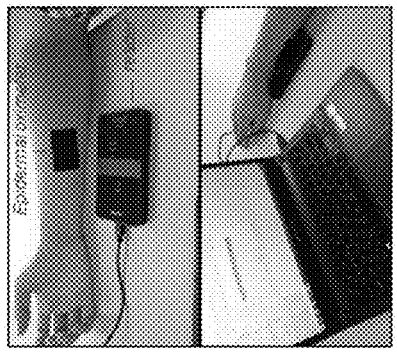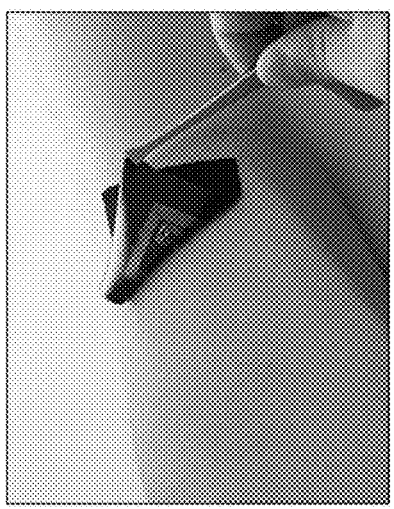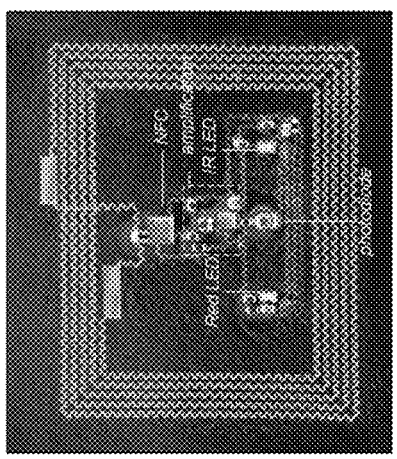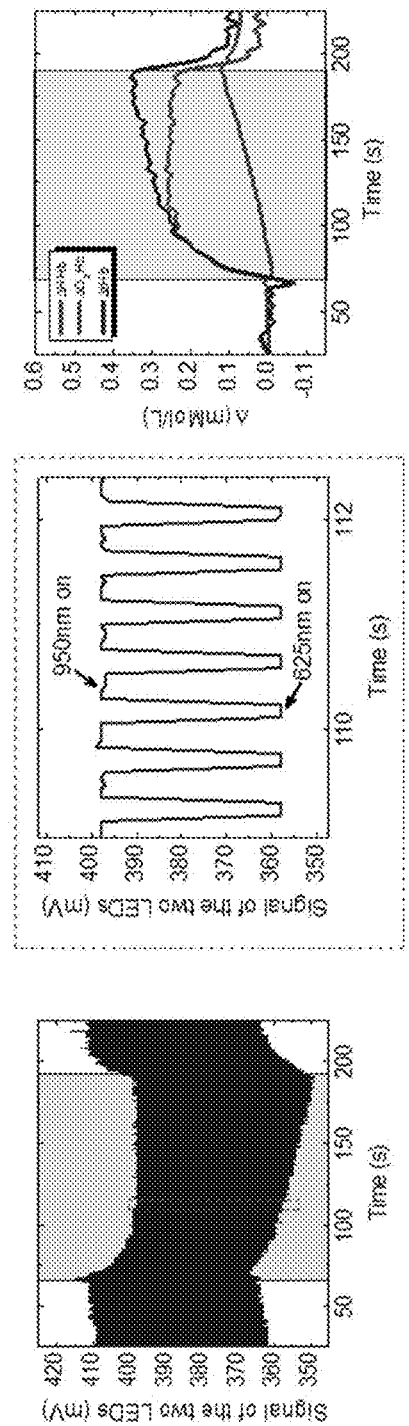
Fig. 30

Devices with Peel tabs for ease of application

Tabs are easily removed and discarded after application

Device stays mounted
Peel tab discarded after placement

Hotel Room Door     Fig. 33     Hotel outside and elevator Door

MINIATURIZED ELECTRONIC SYSTEMS WITH WIRELESS POWER AND NEAR-FIELD COMMUNICATION CAPABILITIES

CROSS-REFERENCE TO RELATED APPLICATIONS

This application is a continuation of U.S. patent application Ser. No. 15/578,602 filed Nov. 30, 2017, which is a National Stage 371 application of PCT/US16/35336 filed Jun. 1, 2016, which claims the benefit of priority from U.S. Provisional Patent Application No. 62/169,308 filed Jun. 1, 2015, U.S. Provisional Patent Application No. 62/169,983 filed Jun. 2, 2015, U.S. Provisional Application No. 62/218,345 filed Sep. 14, 2015, and U.S. Provisional Application No. 62/218,321 filed Sep. 14, 2015, each of which is hereby incorporated by reference in its entirety to the extent not inconsistent herewith.

STATEMENT REGARDING FEDERALLY SPONSORED RESEARCH OR DEVELOPMENT

Not applicable.

BACKGROUND OF INVENTION

Wearable electronics and photonics are a class of systems with potential to broadly impact a range of technologies, industries and consumer products. Advances in wearable systems are driven, in part, by development of new materials and device architectures providing for new functionalities implemented using device form factors compatible with the body. Wearable consumer products are available, for example, that exploit small and portable electronic and/or photonic systems provided in body mounted form factors, such as systems building off of conventional body worn devices such as eye glasses, wrist bands, foot ware, etc. New device platforms are also under development to extend the range of wearable technology applications including smart textiles and stretchable/flexible electronic systems incorporating advanced electronic and photonic functionality in spatially complaint form factors compatible with low power operation, wireless communication and novel integration schemes for interfacing with the body. [See, e.g., Kim et al., Annu. Rev. Biomed. Eng. 2012.14; 113-128; Windmiller, et al., Electroanalysis; 2013, 25, 1, 29-46; Zeng et al., Adv. Mater., 2014, 26, 5310-5336; Ahn et al., J Phys. D: Appl. Phys., 2012, 45, 103001.]

Tissue mounted systems represent one class of wearable systems supporting diverse applications in healthcare, sensing, motion recognition and communication. Recent advances in epidermal electronics, for example, provide a class of skin-mounted electronic and/or optoelectronic systems provided in physical formats enabling intimate contact with the skin. [See, e.g., US Publication No. 2013/0041235.] Epidermal electronic systems combine high performance stretchable and/or ultrathin functional materials with soft elastic substrates implemented in device geometries useful for establishing and maintaining conformal contact with the soft, curvilinear and time varying surface of the skin. A number of sensing modalities have been demonstrated using this platform including physiological monitoring (e.g., temperature, thermal transport, hydration state, etc.) and transduction of chemical information, for example, in connection with the characterization of bodily fluids (e.g., pH, salt composition, etc.). [See, e.g., Huang et al., Small, 2014, 10 (15) 3083-3090; Gao, et al., Nature Communications, 2014, 5, 4938.]

Despite considerable advances in tissue mounted systems a number of challenges remain in the development of certain applications for this technology. First, conformal integration of these systems on some classes of tissue, such as the epidermis, can adversely impact the physiological state and/or chemical condition of the tissue, for example resulting in unwanted irritation and/or immune response. Tissue mounted systems can also influence the exchange of heat, fluid and/or gas at the mounting site, thereby having the potential to interfere with physiological and chemical characterization of tissue. Further, long term, reliable integration remains a challenge for some tissue types such as tissues characterized by rapid rates of growth, fluid exchange and/or exfoliation.

It will be appreciated from the foregoing that tissue mounted electronic and photonic systems are needed to support the emerging applications in wearable electronics. Tissue mounted systems and methods are needed that are capable of robust and intimate integration without substantial delamination. Tissue mounted systems and methods are needed that are capable of providing good electronic and photonic performance in a manner not adversely impacting the tissue at the mounting site. In addition, tissue mounted systems are needed that are compatible with efficient manufacturing to enable cost effective implementation for a range of applications.

SUMMARY OF THE INVENTION

The invention provides systems and methods for tissue-mounted electronics and photonics. Devices of some embodiments of the invention implement high performance, and optionally flexible, device components having miniaturized formats in device architectures that minimize adverse physical effects to tissue and/or reduce interfacial stresses when mounted on tissue surfaces. In some embodiments, the invention provides complementary tissue mounting strategies providing for mechanically robust and/or long term integration of the present devices, for example, via mounting on tissue surfaces that are not subject to rapid growth or exfoliation processes such as the fingernail, toenail, tooth or earlobe. Devices of the invention are versatile and support a broad range of applications for sensing, actuating and communication including applications for near field communication, for example, for password authentication, electronic transactions and biometric sensing.

In one aspect, the invention provides a tissue mounted electronic system, the system comprising: (i) a substrate having an inner surface and an outer surface; and (ii) an electronic device comprising one or more inorganic and/or organic components supported by the outer surface of the substrate; wherein the electronic device has a thickness less than or equal to 5 millimeters, optionally less than 1 millimeter, and has lateral dimensions small enough to provide long-term conformal integration via direct or indirect contact with the tissue without substantial delamination. As used herein, the expression "long-term conformal integration" refers to the capability of the present systems to establish and maintain conformal contact with a tissue surface for at least 3 hours, optionally at least 1 day or at least 1 month, without undergoing delamination or other degradation sufficient to impair electronic or photonic performance. Miniaturized thickness and lateral dimensions are significant in some embodiments for enabling long term conformal integration, for example, wherein the electronic device is characterized by a maximum thickness less than 2 mm, optionally less than 125 micron, less than 0.1 micron or less than 0.05 micron, and/or wherein the electronic device is characterized by an area of less than 2 cm$^2$, optionally less than 0.5 cm$^2$ or less than 0.1 cm$^2$. In an embodiment of this aspect, the electronic system is directly supported by and in physical contact with the tissue or indirectly supported by the tissue, for example, via one or more intermediate components provided in between the system and the tissue.

In another aspect, the invention provides a tissue mounted electronic system, the system comprising: (i) a substrate having an inner surface and an outer surface; and (ii) an electronic device comprising one or more inorganic components, organic components or a combination of inorganic and organic components supported by the outer surface of the substrate; wherein the electronic device has a thickness less than or equal to 10 millimeters, optionally less than 5 millimeters or 1 millimeter, and has lateral dimensions small enough to provide conformal integration with the tissue without inflammation or immune response of the tissue. As used herein, the expression "conformal integration with the tissue without inflammation or immune response" refers to the capability of the present systems to establish conformal contact with a tissue surface without causing an observable inflammation or immune response from the tissue at the mounting site. Miniaturized thickness and lateral dimensions are significant in some embodiments for enabling conformal integration with the tissue without inflammation or immune response, for example, wherein the electronic device is characterized by a maximum thickness less than 2 mm, optionally less than 125 microns, less than 0.1 micron or less than 0.05 micron, and/or wherein the electronic device is characterized by an area of less than 2 cm$^2$, optionally less than 0.5 cm$^2$ or less than 0.1 cm$^2$. In an embodiment of this aspect, the electronic system is directly supported by and in physical contact with the tissue or indirectly supported by the tissue, for example, via one or more intermediate components provided in between the system and the tissue.

In another aspect, the invention provides a tissue mounted electronic system, the system comprising: (i) a substrate having an inner surface and an outer surface; and (ii) an electronic device comprising one or more inorganic components, organic components or combination of inorganic and organic components supported by the outer surface of the substrate; wherein the electronic device has a thickness less than or equal to 10 millimeters, optionally less than 5 millimeters or 1 millimeter, and has lateral dimensions small enough to provide conformal integration with the tissue without substantially changing the exchange of heat and fluids from the tissue surface upon which the system is mounted. As used herein, the expression "conformal integration with the tissue without substantially changing the exchange of heat and fluids" refers to the capability of the present systems to establish conformal contact with a tissue surface without changing the amount of heat and fluids absorbed or released from the tissue surface at the mounting site by a factor greater than 75%, optionally greater than 25%, relative to the tissue surface without the mounted device. Miniaturized thickness and lateral dimensions are significant in some embodiments for enabling conformal integration with the tissue without substantially changing the exchange of heat and fluids, for example, wherein the electronic device is characterized by a maximum thickness less than 2 mm, optionally less than 125 microns, less than 0.1 micron or less than 0.05 micron, and/or wherein the electronic device is characterized by an area of less than 2 cm$^2$, optionally less than 0.5 cm$^2$ or less than 0.1 cm$^2$. In an embodiment of this aspect, the electronic system is directly supported by and in physical contact with the tissue or indirectly supported by the tissue, for example, via one or more intermediate components provided in between the system and the tissue.

In another aspect, the invention provides a tissue mounted electronic system, the system comprising: (i) a substrate having an inner surface and an outer surface; and (ii) an electronic device comprising one or more inorganic components, organic components or combination of inorganic and organic components supported by the outer surface of the substrate; wherein the electronic device is capable of establishing conformal integration with the tissue, and wherein the electronic device undergoes a transformation upon an external stimulus or an internal stimulus; wherein the transformation provides a change in function of the system from a first condition to a second condition. Systems of this aspect may be compatible with a range of external and/or internal stimuli, including movement of the system, tempering with the system, a physical, chemical or electromagnetic change of the system, change in a measured signal or property, change in an ambient parameter and combinations of these. In an embodiment, the transformation provides the change in function of the device from a first condition of operability to a second condition of inoperability. In an embodiment, the transformation is induced upon removal or attempted removal of the system from a mounting position on the tissue. In an embodiment, the transformation is induced by a physical change, a chemical change, a thermal change or electromagnetic change of the system or a component thereof. In an embodiment, the transformation is induced by physical breakage of a component of the system (e.g., breakage of an active component, breakage of an electronic interconnect, breakage of the substrate, breakage of a barrier layer or encapsulating layer, etc.), a physical deformation of a component of the system (e.g. deformation of an active component, deformation of an electronic interconnect, deformation of the substrate, etc.), a change in physical conformation of the system (e.g., change in contour, a change in curvature, etc.), or removal of a barrier or encapsulation layer of the system, for example, such that resulting exposure to the environment induces a change. In an embodiment, the transformation is induced a change in a value of a measured device property (e.g., state of strain, antenna property), a measured physiological property of the tissue or subject (e.g., temperature, pH level, glucose, pulse oximetry, heart rate, respiratory rate, blood pressure, peripheral capillary oxygen saturation (SpO2)) or measured ambient property (e.g., temperature, electromagnetic radiation, etc.). In an embodiment, the transformation is induced by a positional change (e.g., movement of the system) or a temporal change (e.g., upon elapse of a preselected period of time). Miniaturized thickness and lateral dimensions are significant in some embodiments for enabling a capability of undergoing a transformation upon removal from a mounting location, for example, wherein the electronic device is characterized by a maximum thickness less than 2 mm, optionally less than 125 microns, less than 0.1 micron or less than 0.05 micron, and/or wherein the electronic device is characterized by an area of less than 2 cm$^2$, optionally less than 0.5 cm$^2$ or less than 0.1 cm$^2$. In an embodiment of this aspect, the electronic system is directly supported by and in physical contact with the tissue or indirectly supported by the tissue, for example, via one or more intermediate components provided in between the system and the tissue.

In another aspect, the invention provides a tissue mounted electronic system, the system comprising: (i) a substrate having an inner surface and an outer surface; wherein the inner surface of the substrate is for establishing contact with a tissue surface; and (ii) an electronic device comprising one or more inorganic components, organic components or a combination of inorganic and organic components; wherein each of the inorganic components is supported by the outer surface and independently positioned within 20 millimeters, optionally 16 millimeters, or 10 millimeters, or 1 millimeter, of an edge of the substrate (e.g., perimeter edge or edge of a cut-out region positioned away from the perimeter); wherein the tissue mounted electronic device has lateral dimensions less than or equal to 20 millimeters, optionally for some applications less than or equal to 16 millimeters, and a thickness less than or equal to 5 millimeters, optionally for some applications less than or equal to 10 millimeters. In an embodiment of this aspect, the electronic system is directly supported by and in physical contact with the tissue or indirectly supported by the tissue, for example, via one or more intermediate components provided in between the system and the tissue.

As used herein, the term "tissue-mounted" is intended to broadly include a class of systems that upon implementation are supported by one or more tissue surfaces. In some embodiments, upon implementation, tissue-mounted systems of the invention are supported directly by a tissue surface, for example, wherein a surface of the system, such as a substrate surface, is in physical contact with the tissue surface, such as in conformal contact. In some embodiments, upon implementation, tissue-mounted systems of the invention are supported indirectly by a tissue surface, for example, wherein a surface of the system, such as a substrate surface, is in physical contact with an intermediate structure, such as an integration platform, provided between the tissue surface and the tissue-mounted system. A tissue mounted system may be coupled to the body by a wide variety of intermediate structures supported by the body including manufactured materials and non-natural materials. In some embodiments, for example, a tissue mounted system may be directly or indirectly coupled to the body by faux nails (i.e., false finger nails), teeth, clothing (buttons, tags, woven material, etc), jewelry (e.g., rings, bracelets, necklaces, wrist watches, piercings, etc.), body-enhancements, glasses, gloves, nail polish and the like.

Conformal integration refers to the ability of the present systems to be provided to a tissue in a manner that the device spatially conforms at an interface between the system and the tissue or at the interface with an intermediate structure provided between the system and tissue surface. Conformal integration may be via direct or indirect contact with a tissue surface. Tissue mounted systems of the invention may be provided in direct conformal integration, wherein the system itself establishes conformal contact with the tissue surface. Tissue mounted systems of the invention may be provided in indirect conformal integration, wherein the system is provided on an intermediate structure provided in conformal contact with the tissue surface, such as a prosthetic, adhesive tape, faux nails (i.e., false finger nails), clothing (buttons, tags, woven material, etc), jewelry (e.g., rings, bracelets, necklaces, wrist watches, piercings, etc.), body-enhancements, glasses, gloves, nail polish and the like.

In some embodiments, for example, the system has lateral dimensions selected from the range of 5 mm to 20 mm. In some embodiments, for example, the system has thickness dimensions selected from the range of 0.125 mm to 5 mm, or 0.005 mm to 5 mm. In some embodiments, for example, the system is characterized by a footprint/contact area of 10 $mm^2$ to 500 $mm^2$, or 20 $mm^2$ to 350 $mm^2$, or 30 $mm^2$ to 150 $mm^2$, in some embodiments the system is characterized by a footprint/contact area greater than 25 $mm^2$ or greater than 20 $mm^2$. In some embodiments, for example, the system is characterized by an areal mass density of 0.1 mg $cm^{-2}$ to 100 mg $cm^{-2}$. In some embodiments, for example, the system has a tapered thickness from the center to outer edge. In some embodiments, a taper of not less than 5 degrees, or not less than 10 degrees, from the center of the system to the outer edge reduces or prevents delamination. In some embodiments, the system is symmetrically or asymmetrically tapered from the center to the outer edges. In some embodiments, for example, the system has a shape selected from the group consisting of elliptical, rectangular, circular, serpentine and irregular shapes. In some embodiments, for example, the system is characterized by component lateral dimensions selected from 4 mm to 16 mm. In some embodiments, for example, the system comprises Sheldahl Novaclad® adhesiveless laminate made with 18 μm copper×12 μm polyimide film×18 μm copper.

In some embodiments, the overall system geometry is designed to reduce or prevent delamination, for example, via having a tapered geometry. In an embodiment, for example, a portion of, or all, intersecting outer surfaces are joined radially at an angle to reduced or prevent delamination. In an embodiment, for example, the system is characterized by a gradual reduction of thickness in a range equal to or less than the center of the device to outer surface to reduce or prevent delamination. In an embodiment, for example, a thickness at an edge, such as an outer edge of the system or an edge of an aperture of the system, is at least 2 times, or at least 5 times, or at least 10 times, less than a thickness at a center (or mid-point between edges) of a system. In an embodiment, a thickness of the overall system decreases substantially asymptotically from a mid-point of the system to an edge, such as an outer edge of the system or an edge of an aperture of the system.

In some embodiments, the present systems are waterproof, for example, by encapsulation or packaging, with a biopolymer, a thermoset polymer, a rubber, an adhesive tape, plastic or any combination of these. For example, in embodiments, the system comprises an encapsulation layer or other waterproofing structure comprising polyimide, conformal Q, vinyl, acrylic, polydimethylsiloxane (PDMS), polyurethane, vinyl, polystyrene, polymethyl methacrylate (PMMA) or polycarbonate.

In some embodiments, the present systems incorporate an easy peel tab to facilitate deployment onto a tissue surface, for example, that can easily be discarded after mounting.

In an embodiment, the inner surface of the substrate conforms to the curvature of a tissue surface. In embodiments, the inorganic and/or organic components are selected from inorganic and/or organic semiconductor components, metallic conductor components and combinations of inorganic semiconductor components and metallic conductor components. In an embodiment, for example, each of the inorganic components is independently positioned within 10 millimeters, optionally within 1 millimeter, of an edge of the perimeter of the substrate. In an embodiment, each of the inorganic components is independently positioned within 10 millimeters, and in some embodiments less; e.g. optionally within 1 millimeter, of an edge of an aperture in the substrate. In an embodiment, each of the inorganic components is independently characterized by a shortest distance to an edge of the substrate, wherein an average of the shortest distances for the inorganic components is equal to or less than 10 millimeters, optionally equal to or less than 1 millimeter.

Systems and methods of some aspects of the invention exploit overall size miniaturization to achieve a mechanically robust interface with a tissue surface without generating stresses or strains adversely impacting performance and/or to minimize adverse physical effects to tissue. In embodiments, for example, the tissue mounted electronic system has a lateral area footprint less than or equal to 500 $mm^2$, optionally less than or equal to 315 $mm^2$, or selected from the range of 1 $mm^2$ to 500 $mm^2$ and optionally selected from the range of 1 $mm^2$ to 315 $mm^2$. In an embodiment, the ratio of a lateral area foot print of the tissue mounted electronic system to the area of the tissue is greater than or equal to 0.1. In an embodiment, the tissue mounted electronic system has an areal mass density selected from the range of 1 mg $cm^{-2}$ to 100 mg $cm^{-2}$. In embodiments, the tissue mounted electronic system has an average thickness selected from the range of 5 microns to 5 millimeters, optionally 12 microns to 1 millimeter, optionally 50 microns to 90 microns, or, for example, greater than 50 microns. In an embodiment, the tissue mounted electronic system has an overall maximum thickness less than 0.1 mm and at least one region having a thickness selected from the range of 0.05 mm to 0.09 mm. For example, a region of the tissue mounted electronic system comprising a relatively thick component, such as an NFC chip or an LED, may provide a thickness less than 0.1 mm and a region of the tissue mounted electronic system comprising a relatively thin component, such as only substrate, may provide a thickness selected from the range of 0.05 mm to 0.09 mm, or a thickness of less than 0.09 mm, or less than 0.07 mm.

Systems and methods of some aspects of the invention integrate thin, flexible functional components and substrates to provide sufficient mechanical compliance to achieve a conformal interface at the mounting site for a tissue surface. Advantages of mechanically flexible systems of the invention include the ability to conform to complex contoured tissue surfaces and/or tissue surfaces that are dynamic with respect to time. Alternatively, the invention also includes rigid systems integrating rigid functional components and/or substrates, for example, for integration with tissue types having compatible physical properties, such as the fingernail, tooth or toenail. Advantages of mechanically rigid systems of the invention include providing high functionality systems, where thin, mechanically flexible construction might represent a disadvantage, in terms of potential damage during manipulation.

In embodiments, the tissue mounted electronic system has an average modulus selected from the range of 10 kPa to 100 GPa, or greater than 10 kPa, optionally greater than 100 MPa. In embodiments, the tissue mounted electronic system has a flexural rigidity selected from the range of 0.1 nN m to 1 N m. In an embodiment, the tissue mounted electronic system has a net bending stiffness of greater than 0.1 nN m, optionally for some applications greater than 10 nN m, and optionally for some applications greater than 1000 nN m. In some embodiments, for example, one or more mechanical properties of the device, such as average modulus, flexural rigidity or bending stiffness, are matched to properties of the tissue at the mounting site; e.g., within a factor of 5. In embodiments, for example, the system is rigid and in a fixed shape to conform to a tissue surface, such as a curved or contoured shape that matches the tissue surface, e.g., matches the curvature of the fingernail. In embodiments, the tissue mounted electronic system has an adhesion strength selected from the range of 1 N/25 mm to 50 N/25 mm, or the tissue mounted electronic system has an adhesion strength greater than 50 N/25 mm, or greater than 60 N/25 mm. In some embodiments, peel adhesion can be tuned for specific applications after 20 minutes at room temperature.

Systems of the invention include multilayer devices, for example, wherein functional layers having electronically and/or optoelectronically functional device components are separated from each other by structural layers, such as electrically insulating or supporting layers or coatings. In embodiments, the tissue mounted electronic system has a multilayer geometry comprising a plurality of functional layers, supporting layers, encapsulating layers, planarizing layers or any combination of these. In embodiments, the tissue mounted electronic system has a shape selected from the group consisting of elliptical, rectangular, circular, serpentine and/or irregular. In an embodiment, the shape is characterized by an aspect ratio of a lateral dimension to thickness less than 10,000 or optionally for some embodiments selected from the range of 5000 to 3.

Substrates having a range of physical and chemical properties are useful in the systems and methods of the present invention. The invention includes substrates having functionality as an electrical insulator, an optically transparent layer, an optical filter and/or a mechanically supporting layer. In embodiments, the inner surface of the substrate has an area for establishing the conformal contact with the tissue surface less than or equal to 315 $mm^2$, or selected from the range of 19 $mm^2$ to 315 $mm^2$. In an embodiment, the substrate has a perforated geometry including a plurality of apertures extending through the substrate. In an embodiment, the substrate is discontinuous. In an embodiment, the apertures allow passage of gas and fluid from the tissue through the device, in some embodiments, the apertures allow transport of fluid away from the tissue surface. In an embodiment, each of the apertures is independently characterized by lateral dimensions selected from the range of 12 microns to 5 millimeters, or 25 microns to 1 millimeter, or 50 microns to 500 microns. In an embodiment, perforations are distributed in the substrate with a pitch selected from the range of 4 mm to 0.2 mm, or 2 mm to 0.5 mm. In an embodiment, the perforations are openings, such as circular openings, having average diameters greater than 0.1 mm and less than 2 mm, or greater than 0.2 mm and less than 1 mm. In an embodiment, the substrate has an areal density of the apertures selected from the range of one per $cm^2$ to one hundred per $cm^2$. In an embodiment, the apertures are provided in a substantially spatially uniform distribution across the substrate. In an embodiment, the apertures provide an overall mesh geometry of the substrate. In an embodiment, the apertures provide a porosity of the substrate equal to or greater than 0.01%, optionally for some embodiments equal to or greater than 0.1%, or equal to or greater than 1%, or equal to or greater than 10%. In an embodiment, a perforated or discontinuous substrate comprises at least 0.01% open area, or at least 0.1% open area, or at least 0.5% open area, or at least 1% open area, or at least 5% open area, or at least 10% open area. In an embodiment, each of the apertures is independently characterized by a cross sectional area selected from the range of 100 $\mu m^2$ to 1 $cm^2$, or 200 $\mu m^2$ to 1 $mm^2$, or 500 $\mu m^2$ to 0.5 $mm^2$.

In embodiments, the substrate is a flexible substrate or a stretchable substrate. In an embodiment, the substrate is characterized by an average modulus selected from the range of 10 kPa to 100 GPa, or greater than 10 kPa, optionally for some applications greater than 10 kP. In an embodiment, the substrate is characterized by an average thickness selected from the range of 12 microns to 5 millimeters, 25 microns to 1 millimeter, or 50 microns to 90 microns, and in some embodiments, greater than 500 microns, optionally for some embodiments, greater than 1000 microns.

In an embodiment, the substrate comprises one or more thin films, coatings or both. For example, in some embodiments, a coating or thin film is provided directly on the electronic device or component thereof, and in some embodiments, in direct physical contact. In some embodiments, however, the coating or thin film is provided on an intermediate structure positioned between the electronic device and the coating or film. In embodiments, the substrate comprises an inorganic polymer, an organic polymer, a plastic, an elastomer, a biopolymer, a thermoset polymer, a rubber, an adhesive tape or any combination of these. For example, in embodiments, the substrate comprises polyimide polydimethylsiloxane (PDMS), polyurethane, cellulose paper, cellulose sponge, polyurethane sponge, polyvinyl alcohol sponge, silicone sponge, polystyrene, polymethyl methacrylate (PMMA) or polycarbonate.

A range of functional electronic device components and device integration strategies are compatible with the present methods and systems, thereby supporting expansive applications in wearable electronics. In an embodiment, for example, the system further comprises one or more encapsulating layers or coatings for encapsulating the electronic device. In embodiments, the electronic device is a rigid device, a semi-rigid device, a flexible electronic device or a stretchable electronic device. In embodiments, for example, each of the one or more inorganic or organic components independently comprises one or more thin films, nanoribbons, microribbons, nanomembranes or micromembranes. In an embodiment, the one or more inorganic or organic components independently comprise a single crystalline inorganic semiconductor material.

In an embodiment, for example, the one or more inorganic or organic components independently have a thickness selected from the range of 5 microns to 5000 microns, optionally for some applications 50 microns to 100000 microns, optionally for some applications the range of 50 microns to 2000 microns. In an embodiment, for example, the one or more inorganic or organic components independently have a thickness greater than 5 microns and optionally for some embodiments a thickness greater than 50 microns. In an embodiment, the one or more inorganic or organic components are independently characterized by a curved geometry, for example, a bent, coiled, interleaved or serpentine geometry. In an embodiment, the one or more inorganic or organic components are characterized by one or more island and bridge structures.

In embodiments, the electronic device has a multilayer geometry comprising a plurality of functional layers, barrier layers, supporting layers and encapsulating layers. In an embodiment, the electronic device is provided proximate to a neutral mechanical surface of the system. In an embodiment, for example, the electronic device comprises one or more sensors or a component thereof, for example, sensors selected from the group consisting of an optical sensor, an electrochemical sensor, a chemical sensor, a mechanical sensor, a pressure sensor, an electrical sensor, a magnetic sensor, a strain sensor, a temperature sensor, a heat sensor, a humidity sensor, a motion sensor (e.g., accelerometer, gyroscope), a color sensor (colorimeter, spectrometer), an acoustic sensor, a capacitive sensor, an impedance sensor, a biological sensor, an electrocardiography sensor, an electromyography sensor, an electroencephalography sensor, an electrophysiological sensor, a photodetector, a particle sensor, a gas sensor, an air pollution sensor, a radiation sensor, an environmental sensor and an imaging device.

In an embodiment, the electronic device comprises one or more actuators or a component thereof, for example, actuators or a component thereof generating electromagnetic radiation, optical radiation, acoustic energy, an electric field, a magnetic field, heat, a RF signal, a voltage, a chemical change or a biological change. In embodiments, the one or more actuators or a component thereof are selected from the group consisting of a heater, an optical source, an electrode, an acoustic actuator, a mechanical actuator, a microfluidic system, a MEMS system, a NEMS system, a piezoelectric actuator, an inductive coil, a reservoir containing a chemical agent capable of causing a chemical change or a biological change, a laser, and a light emitting diode.

In embodiments, the electronic device comprises one or more energy storage systems or a component thereof, for example, energy storage systems or components thereof selected from the group consisting of an electrochemical cell, a fuel cell, a photovoltaic cell, a wireless power coil, a thermoelectric energy harvester, a capacitor, a super capacitor, a primary battery, a secondary battery and a piezoelectric energy harvester.

In embodiments, the electronic device comprises one or more communication systems or a component thereof, for example, communication systems or components thereof selected from the group consisting of a transmitter, a receiver, a transceiver, an antenna, and a near field communication device.

In embodiments, the electronic device comprises one or more coils, for example, inductive coils or near-field communication coils. In an embodiment, each of the near-field communication coils independently has a diameter selected from the range of 50 microns to 20 millimeters. In an embodiment, for example, each of the near-field communication coils independently has an average thickness selected from the range of 1 micron to 5 millimeters, 1 micron to 500 microns, 1 micron to 100 microns, 5 microns to 90 microns, or 50 microns to 90 microns. In an embodiment, for example, each of the near-field communication coils changes by less than 50%, and optionally changes by less than 20%, upon changing from a planar configuration to a bent configuration characterized by a radius of curvature selected from the range of 1 mm to 20 mm. In an embodiment, each of the near-field communication coils is characterized by a Q factor greater than or equal to 3. In an embodiment, the one or more coils are at least partially encapsulated by the substrate or one or more encapsulation layers. In embodiments, for example, the one or more coils have a geometry selected from the group consisting of an annulus or an elliptical annulus. In an embodiment, the tissue mounted system of the invention comprises at least two layered coils, wherein the coils are separated by a dielectric layer.

In some embodiments, the transfer of information to and/or from the system is done wirelessly, for example, through ISO standards such as ISO14443 for proximity contanctless cards, ISO15693 for vicinity contactless cards, ISO18000 set of standards for RFIDs and EPC global Class 1 Gen 2 (=18000-6C).

In an aspect, the tissue mounted system of the invention further comprises a mounting platform to provide effective integration with one or more tissue surfaces. In some embodiments, for example, the mounting platform has an external surface for establishing contact with a surface of said tissue and an internal surface for supporting said electronic device and substrate. In an embodiment, the mounting platform is the substrate component of the system itself. In an embodiment, said mounting platform is for establishing conformal contact with said tissue surface, such as establishing conformal contact with a surface of a fingernail. The invention includes mounting platform components that are rigid or flexible. In an embodiment, the mounting platform is a prosthetic. In an embodiment, the mounting platform is an adhesive tape. In an embodiment, the mounting platform is a false fingernail.

In some embodiments, the system further comprises one or more LED components, for example, to provide an indication of device functionality or for aesthetics. In an embodiment, for example, the system includes one or more LED components designed to remain on after being removed from a reader. In an embodiment, for example, the system is incorporated in or encapsulated by a faux nail or nail covering, such as nail polish. In an embodiment, for example, the system includes cover layers or packaging to be made to match tissue in shape and color, for example, for a camouflage function.

In some embodiments, for privacy, the invention has a devoted chip that stores an encrypted identification number that is unique to each individual device. In addition, the chip has action-specific security codes that change constantly. The encrypted device number helps keep patient health-care information private. Clinicians, hospital management, and insurance providers are the only users with access to the information. In case of emergency, hospital personnel can quickly locate missing patients and or observe patient vital signs.

The systems and methods disclosed herein are versatile and perform a wide array of biological functions for a diverse range of tissue types. In addition, the present invention may be used to communicate to a variety of external electronic devices. In an embodiment, for example, the inner surface of the substrate is capable of establishing conformal contact with the tissue surface comprising an external tissue. In embodiments, the external tissue is skin, a fingernail, a toenail, a tooth, hair or an ear lobe. In an embodiment, hair includes but is not limited to hair on a wearer's head, eyebrows or body hair. In embodiments, for example, the inner surface of the substrate is bonded to the tissue surface via an adhesive, such as an acrylic, silicone, ACP, Conformal Q, lead free solder or any combination of these. In an embodiment, the system further comprises a near field communication device, for example, a near field communication device for password authentication, electronic transactions or biosensing. In an embodiment, the near field communication device is for communicating with a computer or mobile electronic device.

In an aspect, the present invention is a method of sensing, actuating or communicating; the method comprising: (i) providing a tissue mounted electronic system on a tissue surface; wherein the tissue mounted electronic system comprises: (a) a substrate having an inner surface and an outer surface; and (b) an electronic device comprising one or more inorganic components, organic components or combination of inorganic and organic components supported by the outer surface of the substrate; wherein the electronic device has a thickness less than or equal to 5 millimeters, optionally less than 10 millimeters, and has lateral dimensions small enough to provide long-term conformal integration with the tissue without substantial delamination; and (ii) sensing, actuating or communicating using the tissue mounted electronic system.

In an aspect, the present invention is a method of sensing, actuating or communicating; the method comprising: (i) providing a tissue mounted electronic system on a tissue surface; wherein the tissue mounted electronic system comprises: (a) a substrate having an inner surface and an outer surface; and (b) an electronic device comprising one or more inorganic components, organic components or combination of inorganic and organic components supported by the outer surface of the substrate; wherein the electronic device has a thickness less than or equal to 5 millimeters, optionally less than 10 millimeters, and has lateral dimensions small enough to provide conformal integration with the tissue without substantial inflammation or immune response; and (ii) sensing, actuating or communicating using the tissue mounted electronic system.

In an aspect, the present invention is a method of sensing, actuating or communicating; the method comprising: (i) providing a tissue mounted electronic system on a tissue surface; wherein the tissue mounted electronic system comprises: (a) a substrate having an inner surface and an outer surface; and (b) an electronic device comprising one or more inorganic components, organic components or combination of inorganic and organic components supported by the outer surface of the substrate; wherein the electronic device has a thickness less than or equal to 5 millimeters, optionally less than 1 millimeter, and has lateral dimensions small enough to provide conformal integration with the tissue without substantially changing the exchange of heat and fluids from the tissue surface upon which the system is mounted; and (ii) sensing, actuating or communicating using the tissue mounted electronic system.

In an aspect, the present invention is a method of sensing, actuating or communicating; the method comprising: (i) providing a tissue mounted electronic system on a tissue surface; wherein the tissue mounted electronic system comprises: (a) a substrate having an inner surface and an outer surface; and (b) an electronic device comprising one or more inorganic components, organic components or combination of inorganic and organic components supported by the outer surface of the substrate; wherein the electronic device has a thickness less than or equal to 5 millimeters, optionally less than 10 millimeters, and has lateral dimensions small enough to provide conformal integration with the tissue in a manner such that it is rendered functionally inoperable upon removal from the tissue; and (ii) sensing, actuating or communicating using the tissue mounted electronic system.

In an aspect, the present invention is a method of sensing, actuating or communicating; the method comprising: (i) providing a tissue mounted electronic system on a tissue surface; wherein the tissue mounted electronic system comprises: (a) a substrate having an inner surface and an outer surface; wherein the inner surface of the substrate is for establishing contact with a tissue surface; (b) an electronic device comprising one or more inorganic components, organic components or combination of inorganic and organic components supported by the outer surface and independently positioned within 10 millimeters, optionally 1 millimeter, of an edge of the substrate (e.g., perimeter edge or edge of a cut-out region positioned away from the perimeter); wherein the tissue mounted electronic device has lateral dimensions less than or equal to 20 millimeters and a thickness less than or equal to 5 millimeters, optionally for some applications less than or equal to 10 millimeters; and (ii) sensing, actuating or communicating using the tissue mounted electronic system.

The invention includes mounting strategies supportive of a range of applications for wearable electronics. In an embodiment, for example, the tissue surface comprises an external tissue of a subject, such as a human or nonhuman subject. In an embodiment, for example, the external tissue is characterized by a growth rate less than or equal to 6 mm per month or for some embodiments less than or equal to 0.1 mm per day. In an embodiment, for example, the external tissue is characterized by a rate of exfoliation less than or equal to once per day or for some embodiments less than or equal to 0.1 mm per day. In an embodiment, for example, the external tissue is characterized by a modulus greater than or equal to 10 kPa, optionally for some embodiments greater than or equal to 10 MPa. In an embodiment, for example, the external tissue is characterized by a bending stiffness greater than or equal to 0.1 nN m, optionally for some embodiments greater than or equal to 100 nN m or greater than or equal to 1000 nN m. In an embodiment, for example, the tissue surface is characterized by a radius of curvature selected from the range of 1 mm to 25 mm.

In an embodiment, for example, the tissue is human tissue. In an embodiment, for example, the tissue is skin, fingernail, a tooth, hair or an ear lobe of a human subject. In an embodiment, for example, the tissue is not epidermal tissue. In an embodiment, for example, the tissue is not internal tissue. In an embodiment, for example, the tissue is non-human tissue, such as tissue of a non-human animal, for example for livestock or veterinary applications. In an embodiment, for example, the tissue is non-human tissue, such as tissue of a plant (e.g. leaves and/or roots), for example for agricultural applications.

In an embodiment, the sensing, actuating or communicating comprises generating or receiving a near field communication signal, for example, wherein the near field communication signal is received or generated by a computer or portable electronic device. In an embodiment, for example, the near field communication signal is for password authentication, electronic transactions or biosensing.

In an embodiment, for example, the sensing, actuating or communicating comprises sensing one or more tissue properties, such as physiological, electrophysiological, chemical, thermal or optical properties of the tissue. In an embodiment, for example, the sensing, actuating or communicating comprises sensing one or more physical or chemical properties of a biological fluid from the tissue.

In an embodiment, for example, the sensing, actuating or communicating comprises actuating the tissue. In an embodiment, for example, the actuating comprises electrostatically, thermally, optically, acoustically, magnetically or chemically actuating the tissue.

In an embodiment, for example, a step of sensing one or more properties comprises sensing a discrete, substantially instantaneous signal or sensing a cumulative signal acquired over a period of time.

In an embodiment, multiple tissue mounted systems, spatially distributed from one another, may provide data indicative of a spatially or spatiotemporally varying property.

In an aspect, the present invention is a method of authenticating a user to an external device; the method comprising: providing a tissue mounted electronic system on a tissue surface; wherein the tissue mounted electronic system comprises: a substrate having an inner surface and an outer surface; and an electronic device comprising one or more inorganic components, organic components or a combination of inorganic and organic components supported by the outer surface of the substrate (e.g., perimeter edge or edge of a cut-out region positioned away from the perimeter); and communicating using the tissue mounted electronic system to provide an authentication signal to an external device. In an embodiment, upon receiving the authentication signal the external device grants the user access to operate the external device. For example, the external device may be a computer, a phone, a gun, a pill bottle, a door, a vehicle, a safe, a lockbox, a turnstile, a gate, an elevator or a lock.

In an aspect, the present invention is a method of making an electronic payment; the method comprising: providing a tissue mounted electronic system on a tissue surface; wherein the tissue mounted electronic system comprises: a substrate having an inner surface and an outer surface; and an electronic device comprising one or more inorganic components, organic components or a combination of inorganic and organic components supported by the outer surface of the substrate (e.g., perimeter edge or edge of a cut-out region positioned away from the perimeter); and communicating using the tissue mounted electronic system to provide payment information to an external device.

In an aspect, the present invention is a method of ensuring user compliance; the method comprising: providing a tissue mounted electronic system on a tissue surface; wherein the tissue mounted electronic system comprises: a substrate having an inner surface and an outer surface; and an electronic device comprising one or more inorganic components, organic components or a combination of inorganic and organic components supported by the outer surface of the substrate (e.g., perimeter edge or edge of a cut-out region positioned away from the perimeter); and communicating a signal indicative of a location and identification of the tissue mounted electronic system to an external device.

In an aspect, the present invention is a method of transferring digital content; the method comprising: providing a tissue mounted electronic system on a tissue surface; wherein the tissue mounted electronic system comprises: a substrate having an inner surface and an outer surface; and an electronic device comprising one or more inorganic components, organic components or a combination of inorganic and organic components supported by the outer surface of the substrate (e.g., perimeter edge or edge of a cut-out region positioned away from the perimeter); and communicating a signal indicative of the digital content from the tissue mounted electronic system to an external device.

In an embodiment, the electronic device is rendered functionally inoperable upon removal from a tissue. For example, in an embodiment, the electronic device is rendered functionally inoperable by physical breakage or deformation of at least a portion of a device component. In another embodiment, the electronic device is rendered functionally inoperable by removal of a barrier or encapsulation layer to expose at least a portion of a device component to an external environment. According to this embodiment, exposed device components may be physically or chemically removed by elements in the external environment. Exemplary device components that may be broken, deformed or exposed include, but are not limited to, interconnects, coils, substrates or a combination thereof. In an embodiment, the deformation comprises a change in curvature of the system toward the inner surface of the substrate greater than or equal to a 4 mm radius of curvature. In an embodiment, the deformation comprises a change in curvature of the system away from the inner surface of the substrate.

In an embodiment, the electronic device is rendered functionally inoperable when a value of a measured physiological property is outside of a threshold window. In an embodiment, the physiological property may be selected from the group consisting of temperature, pH level, glucose, pulse oximetry, heart rate, respiratory rate, blood pressure, peripheral capillary oxygen saturation (SpO2) and combinations thereof. For example, a temperature below the typical basal body temperature of a wearer of a device may indicate that the device has been removed from tissue, or a pulse or heart rate of zero may indicate that a wearer is deceased, and the device should be rendered inoperable. Inoperability may be achieved, for example, by a microprocessor of the device initiating instructions that prevent transmission (e.g., of secure information, such as personal identifying information or payment information) from the electronic device to an external device or by a microprocessor of the electronic device initiating instructions to provide excess power to a component of the device to electrically destroy the component, thereby achieving functional inoperability.

In an embodiment, the electronic device is rendered functionally inoperable after a predetermined amount of time, after being used a set number of times, or upon failure to properly authenticate after a set number of tries. For example, the electronic device may self-destruct or become unusable after a set period of time after being used a set number of times, or upon failure to properly authenticate after a set number of tries. In an embodiment, the predetermined amount of time or allowable usages or authentication attempts is programmed into a microcontroller of the electronic device and inoperability may be achieved, for example, by a microprocessor of the device initiating instructions that prevent transmission from the electronic device to an external device or by a microprocessor of the electronic device initiating instructions to provide excess power to a component of the device to electrically destroy the component, thereby achieving functional inoperability.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 4. Experimental and simulation results for the electromagnetic properties of mm-NFC devices with elliptical shapes. (a) Pictures of elliptical mm-NFC devices with different eccentricities (i.e. ratios of major to minor axes, b/a). (b) Measured phase responses of the coils as a function of eccentricity and (c) corresponding simulation results. (d) Measured and simulated changes in resonant frequency with b/a. (e) Measured and simulated changes in Q factor with b/a.

FIG. 11 provides images of fingernail authentication device designs. The panel to the left shows a fingernail mounted system comprising NFC coils and NFC chip components provided in a miniaturized format. The panel to the right shows a fingernail mounted system further comprising an energy harvesting LED indicator also provided in a miniaturized format.

FIG. 21 provides a description of example applications of the present devices in hospital and clinical settings.

FIG. 24 provides a schematic illustration of example applications of devices of the invention for phototherapy in the NICU.

FIG. 26 provides a schematic illustration of example applications of devices of the invention for infectious disease compliance.

FIG. 29 provides a schematic illustration of example applications of devices of the invention for pulse rate monitoring.

FIG. 30 provides a schematic illustration of example applications of devices of the invention for oximetry.

DETAILED DESCRIPTION OF THE INVENTION

Figures 1A, 1B:
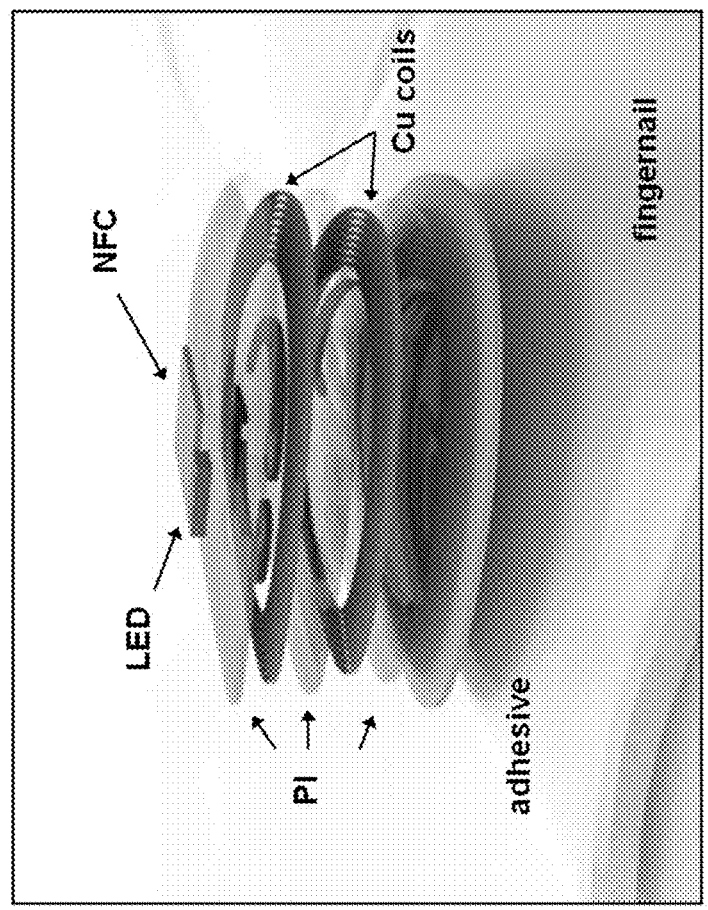
FIG. 1A. Schematic illustration of a top plan view of a tissue mounted system comprising a fingernail mounted NFC device.
FIG. 1B. Schematic illustration of a side exploded view of a tissue mounted system comprising a fingernail mounted NFC device.

In general, the terms and phrases used herein have their art-recognized meaning, which can be found by reference to standard texts, journal references and contexts known to those skilled in the art. The following definitions are provided to clarify their specific use in the context of the invention.

The terms "flexible" and "bendable" are used synonymously in the present description and refer to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. A used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 100 microns, optionally less than 10 microns and optionally less than 1 micron) and device geometries such as thin film and mesh geometries.

The term "tissue" is used broadly to describe any types of material of which animals or plants are made, for example, consisting of specialized cells and their products. A used herein tissue may refer to cells corresponding to one or more organs, such as cells that substantially carry out the same or complementary functions. Tissue as referred to herein may correspond to animals, including human and non-human animals (e.g., livestock, veterinary animals, etc.), and plants. Tissue as referred to herein may correspond to living cells or dead cells which may include, but are not limited to, the corpus *unguis*, (e.g., fingernail, toenail, claw hoof, horn, etc.). Examples of tissues include skin, a fingernail, a toenail, a tooth, a bone, hair or an ear lobe.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. As used herein, many stretchable structures are also flexible. Some stretchable structures (e.g., device components) are engineered to be able to undergo compression, elongation and/or twisting so as to be able to deform without fracturing. Stretchable structures include thin film structures comprising stretchable materials, such as elastomers; bent structures capable of elongation, compression and/or twisting motion; and structures having an island-bridge geometry. Stretchable device components include structures having stretchable interconnects, such as stretchable electrical interconnects.

"Functional layer" refers to a device-containing layer that imparts some functionality to the device. For example, the functional layer may be a thin film such as a semiconductor layer. Alternatively, the functional layer may comprise multiple layers, such as multiple semiconductor layers separated by support layers. The functional layer may comprise a plurality of patterned elements, such as interconnects running between device-receiving pads or islands. The functional layer may be heterogeneous or may have one or more properties that are inhomogeneous. "Inhomogeneous property" refers to a physical parameter that can spatially vary, thereby effecting the position of the neutral mechanical surface (NMS) within the multilayer device.

"Semiconductor" refers to any material that is an insulator at a low temperature, but which has an appreciable electrical conductivity at temperatures of approximately 300 Kelvin. In the present description, use of the term semiconductor is intended to be consistent with use of this term in the art of microelectronics and electronic devices. Useful semiconductors include those comprising element semiconductors, such as silicon, germanium and diamond, and compound semiconductors, such as group IV compound semiconductors such as SiC and SiGe, group III-V semiconductors such as AlSb, AlAs, Aln, AlP, BN, GaSb, GaAs, GaN, GaP, InSb, InAs, InN, and InP, group III-V ternary semiconductors alloys, such as $Al_xGa_{1-x}As$, group II-VI semiconductors, such as CsSe, CdS, CdTe, ZnO, ZnSe, ZnS, and ZnTe, group I-VII semiconductors, such as CuCl, group IV-VI semiconductors, such as PbS, PbTe and SnS, layer semiconductors, such as $PbI_2$, $MoS_2$ and GaSe, and oxide semiconductors, such as CuO and $Cu_2O$. The term semiconductor includes intrinsic semiconductors and extrinsic semiconductors that are doped with one or more selected materials, including semiconductors having p-type doping materials and n-type doping materials, to provide beneficial electronic properties useful for a given application or device. The term semiconductor includes composite materials comprising a mixture of semiconductors and/or dopants. Specific semiconductor materials useful for some embodiments include, but are not limited to, Si, Ge, SiC, AlP, AlAs, AlSb, GaN, GaP, GaAs, GaSb, InP, InAs, GaSb, InP, InAs, InSb, ZnO, ZnSe, ZnTe, CdS, CdSe, ZnSe, ZnTe, CdS, CdSe, CdTe, HgS, PbS, PbSe, PbTe, AlGaAs, AlInAs, AlInP, GaAsP, GaInAs, GaInP, AlGaAsSb, AlGaInP, and GaInAsP. Porous silicon semiconductor materials are useful for applications of aspects described herein in the field of sensors and light emitting materials, such as light emitting diodes (LEDs) and solid state lasers. Impurities of semiconductor materials are atoms, elements, ions and/or molecules other than the semiconductor material(s) themselves or any dopants provided to the semiconductor material. Impurities are undesirable materials present in semiconductor materials, which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

"Coincident" refers to the relative position of two or more objects, planes or surfaces, for example a surface such as a neutral mechanical surface (NMS) or neutral mechanical plane (NMP) that is positioned within or is adjacent to a layer, such as a functional layer, substrate layer, or other layer. In an embodiment, a NMS or NMP is positioned to correspond to the most strain-sensitive layer or material within the layer. "Proximate" refers to the relative position of two or more objects, planes or surfaces, for example a NMS or NMP that closely follows the position of a layer, such as a functional layer, substrate layer, or other layer while still providing desired flexibility or stretchability without an adverse impact on the strain-sensitive material physical properties. In general, a layer having a high strain sensitivity, and consequently being prone to being the first layer to fracture, is located in the functional layer, such as a functional layer containing a relatively brittle semiconductor or other strain-sensitive device element. A NMS or NMP that is proximate to a layer need not be constrained within that layer, but may be positioned proximate or sufficiently near to provide a functional benefit of reducing the strain on the strain-sensitive device element when the device is folded.

In this aspect, "strain-sensitive" refers to a material that fractures or is otherwise impaired in response to a relatively low level of strain. In an aspect, the NMS is coincident or proximate to a functional layer. In an aspect the NMS is coincident to a functional layer, referring to at least a portion of the NMS located within the functional layer that contains a strain-sensitive material for all lateral locations along the NMS. In an aspect, the NMS is proximate to a functional layer, wherein although the NMS may not be coincident with the functional layer, the position of the NMS provides a mechanical benefit to the functional layer, such as substantially lowering the strain that would otherwise be exerted on the functional layer but for the position of the NMS. For example, the position of a proximate NMS is optionally defined as the distance from the strain-sensitive material that provides an at least 10%, 20%, 50% or 75% reduction in strain in the strain-sensitive material for a given folded configuration, such as a device being folded so that the radius of curvature is on the order of the millimeter or centimeter scale. In another aspect, the position of a proximate NMS can be defined in absolute terms such as a distance from the strain-sensitive material, such as less than several mm, less than 2 mm, less than 10 µm, less than 1 µm, or less than 100 nm. In another aspect, the position of a proximate layer is defined relative to the layer that is adjacent to the strain-sensitive material, such as within 50%, 25% or 10% of the layer closest to the strain-sensitive-containing layer. In an aspect, the proximate NMS is contained within a layer that is adjacent to the functional layer.

A "component" is used broadly to refer to an individual part of a device.

"Sensing" refers to detecting the presence, absence, amount, magnitude or intensity of a physical and/or chemical property. Useful device components for sensing include, but are not limited to electrode elements, chemical or biological sensor elements, pH sensors, temperature sensors, strain sensors, mechanical sensors, position sensors, optical sensors and capacitive sensors.

"Actuating" refers to stimulating, controlling, or otherwise affecting a structure, material or device component. Useful device components for actuating include, but are not limited to, electrode elements, electromagnetic radiation emitting elements, light emitting diodes, lasers, magnetic elements, acoustic elements, piezoelectric elements, chemical elements, biological elements, and heating elements.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component).

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90% of the external surface of the structure is surrounded by one or more structures. "Completely encapsulated" refers to the orientation of one structure such that it is completely surrounded by one or more other structures.

"Dielectric" refers to a non-conducting or insulating material.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyimide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to silicon containing polymers such as polysiloxanes including poly(dimethyl siloxane) (i.e. PDMS and h-PDMS), poly(methyl siloxane), partially alkylated poly (methyl siloxane), poly(alkyl methyl siloxane) and poly (phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt a contour profile desired for a specific application, for example a contour profile allowing for conformal contact with a surface having a non-planar geometry such as a surface with relief features or a dynamic surface (e.g. changes with respect to time). In certain embodiments, a desired contour profile is that of a finger nail, skin, tooth, toe nail or ear lobe.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface.

"Young's modulus" or "modulus" are used interchangeably and refer to a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where E is Young's modulus, $L_0$ is the equilibrium length, $\Delta L$ is the length change under the applied stress, F is the force applied, and A is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components having a low Young's modulus. In an embodiment, a device of the invention has an overall low Young's modulus.

"Low modulus" refers to materials having a Young's modulus less than or equal to 10 MPa, less than or equal to 20 MPa or less than or equal to 1 MPa.

"Bending stiffness" is a mechanical property of a material, device or layer describing the resistance of the material, device or layer to an applied bending movement. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

"Lateral dimensions" refer to physical dimensions of a structure such as a tissue mounted electronic system or component thereof. For example, lateral dimensions may refer to one or more physical dimensions oriented orthogonal to axes extending along the thickness of a structure, such as the length, the width, the radius or the diameter of the structure. Lateral dimensions are useful for characterizing the area of an electronic system or component thereof, such as characterizing the lateral area footprint of a system corresponding to a two dimensional area in a plane or a surface positioned orthogonal to axes extending along the thickness of the structure.

FIG. 1A provides a top plan view and FIG. 1B provides a side exploded view of a tissue mounted system comprising a fingernail mounted NFC device. The device of this embodiment supports wearable electronic applications compatible with communication with cellular phones, and other NFC enabled communication platforms. A broad range of near field communication applications is supported by the present systems including password authentication, electronic transactions, biosensing, and motion recognition.

As shown in FIGS. 1A and 1B, the fingernail mounted NFC device comprises a multilayer structure including electronically and/or optically functional layers and structural and/or electrically insulated layers. The device of this embodiment has miniaturized overall dimensions on the millimeter scale. As shown in FIG. 1B the functional layers comprise a pair of copper NFC indication coils and LED and NFC chip components. The coils are a characterized by radii greater than approximately 5 mm and thicknesses of approximately 20 microns. The LED and NFC chip components are characterized by thicknesses of approximately 100 microns. As shown in FIG. 1, the NFC chip component electrically connects to the coils via contacts located near center regions of the coils.

As shown in FIG. 1B, the NFC device further includes structural and/or electrically insulated layers comprising polyimide coatings that are positioned to physically encapsulate the copper coils and an adhesive, such as a low modulus acrylic, serving as the substrate. In some embodiments, for example, a thin silicone elastomer (e.g., less than 100 microns) is provided to encapsulate the system. In some embodiments, structural and/or electrically insulated layers (e.g. polyimide coatings, adhesive, etc.) have thicknesses and positions placing functional device elements, e.g., the coils or chips, coincident with or proximate to the neutral mechanical surface of the device.

In the example shown in FIGS. 1A and 1B, mounting on the external surface of fingernail is provided. In these embodiments, the system may have overall physical properties providing overall flexibility sufficient to achieve mechanically robust and conformal contact with the curvilinear surface of the fingernail. Systems of the invention are also compatible with mounting on a variety of tissue surfaces including external tissues such as the tooth, toenail, ear lobe, hair and skin. Mounting on the fingernail, however, provides certain benefits useful for some applications including very stable and mechanically robust mounting for time periods greater than 6 months with a low risk for discomfort or delamination. The example systems shown in FIGS. 1A and 1B also provide a platform compatible with multifunctional implementation wherein additional electronic and/or photonic systems are integrated into the system. The example systems shown in FIGS. 1A and 1B are also compatible with overall device designs for preventing removal and/or re-use, for example, by providing for loss of functionality and/or destruction upon attempted removal.

Example 1

Abstract

This Example introduces a class of thin, lightweight, flexible near field communication (NFC) devices with ultraminiaturized format, and presents systematic investigations of the mechanics, radio frequency characteristics and materials aspects associated with their optimized construction. These systems allow advantages in mechanical strength, placement versatility, and minimized interfacial stresses compared to other NFC technologies and wearable electronics. Detailed experimental studies and theoretical modeling of the mechanical and electromagnetic properties of these systems establish understanding of the key design considerations. These concepts can apply to many other types of wireless communication systems including bio-sensors and electronic implants.

Introduction

Wearable electronic technologies form the foundation for a rapidly growing consumer device segment. Projections suggest that over $100 billion will be spent in materials alone over the coming decade in the pursuit of new wearable devices[1]. Advances in materials and device architectures for these systems will create opportunities for increasing the range of capabilities, expanding the modes of use, improving the robustness/reliability, reducing the size/weight and lowering the cost. The cellular phone platform will likely remain a key element in the broader technology landscape, as in currently available wrist band and watch style devices that measure body processes and communicate data to the phone[2,3]. Recent research demonstrates much different types of integration strategies compared to those of these existing systems, in which the wearable devices take the form of temporary transfer tattoos. The result is greatly improved contact with the body and corresponding increases in the diversity and accuracy of information that can be collected from integrated sensors[2,4,5]. Here, an overarching goal is to engineer the physical properties, and in particular the elastic modulus and elastic stretchability, to match those of the epidermis, as a way to reduce irritation and discomfort at the skin interface and to improve the robustness of the bonding[2,4,6]. In this Example, we present a complementary strategy, in which overall size miniaturization serves as an additional, and sometimes primary, means for minimizing physical effects on the skin. This scheme also expands the options in mounting locations, to include areas such as the fingernails and the teeth, where mechanical compliance is not always required and where mounting times can extend to several months, or more. In particular, we introduce thin, lightweight, flexible near field communication (NFC) devices in ultraminiaturized formats, along with systematic studies of the mechanics and materials aspects associated with their optimized construction. The potential applications include password authentication[7], electronic transactions[8] and biometric sensing[9], each performed via wireless power and communication to cellular phones or other NFC enabled platforms. Such devices consume nearly one hundred times less area than conventional wrist-worn NFC devices and they are ~100 and ~10,000 times thinner and lighter in weight, respectively. The areas are also nearly ten times smaller than those of recently reported NFC devices with epidermal construction[2] and are, to our knowledge, the smallest to be explored for integration on the surface of the human body. Rigid, capsule-shaped NFC devices with volumes ~10 times larger than those of the devices reported here are available for implantation into the human body[10]. Open architecture designs provide a high tolerance to deformation and physical stresses when mounted on soft surfaces such as the epidermis. Experimental measurements of the mechanical and electromagnetic properties compare favorably to theoretical modeling results. Device operation using standard NFC enabled consumer electronics demonstrate the capabilities in evaluations that are supportive of a range of applications.

Results and Discussion

Figure 2:
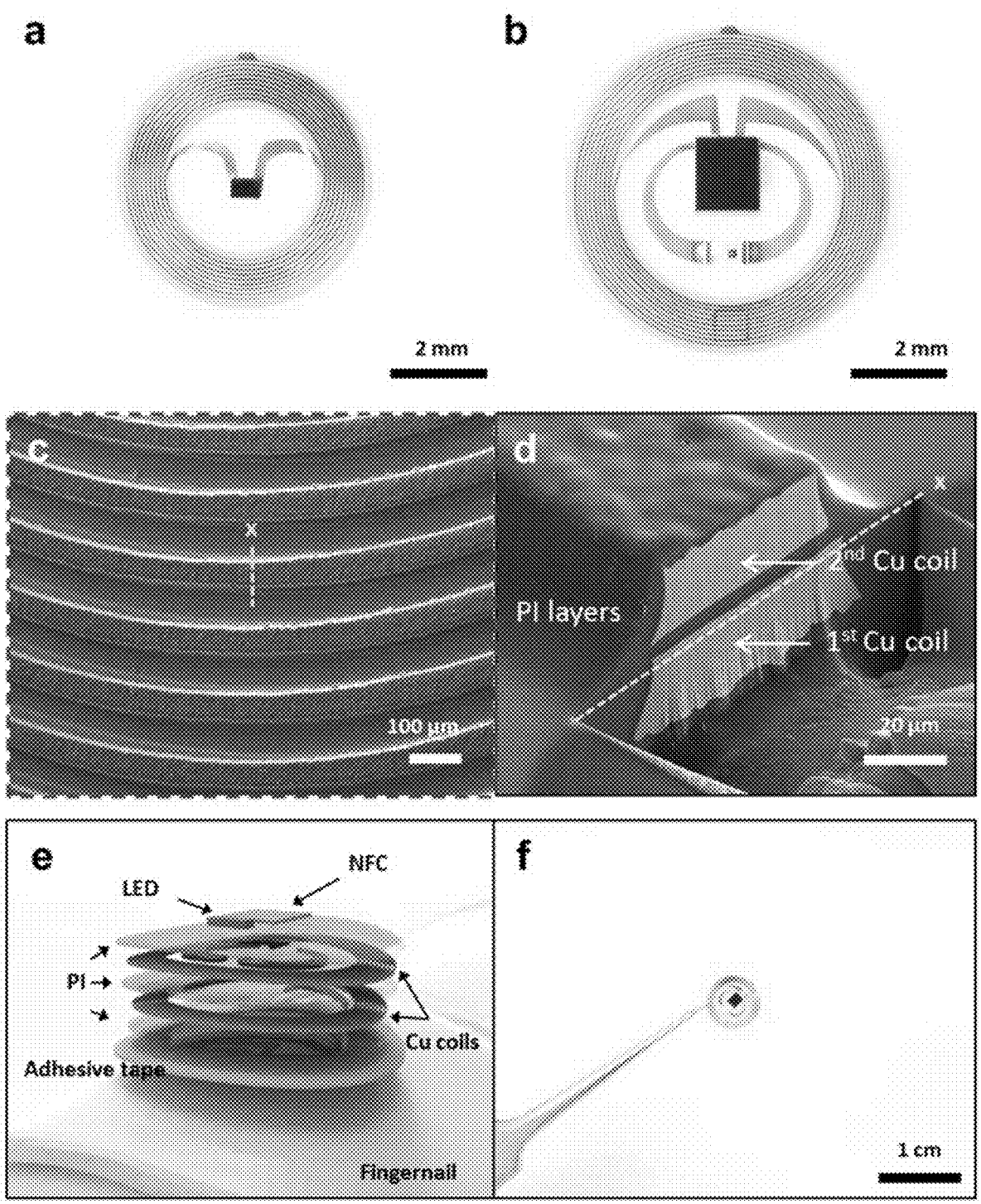
FIG. 2. Schematic illustration and images of flexible mm-NFC devices with and without LEDs. (a, b) Pictures of the devices and (c) scanning electron microscope image of the region of (b) indicated by the red dashed box. (d) Cross-sectional SEM image of one part of the coils. (e) Exploded-view schematic illustration of each layer of a device mounted on a fingernail. (f) Picture of a free-standing device held at one edge by tweezers.

FIG. 2 summarizes the layered, open architecture designs of these ultraminiaturized, or millimeter-scale, NFC (mm-NFC) devices. FIG. 2a, b shows optical microscope images of mm-NFC devices with diameters of 5.8 mm and 7.04 mm. For both cases, each of the coils in the dual-coil layout consist of copper traces with 9 turns (18 µm thick), to enable high Q factors and resonance frequencies near 14 MHz. These platforms exploit thinned NFC die selected from a range of commercially available components. The experiments reported here use NTAG216 (NXP semiconductor) and M24LR04E (ST Microelectronics) chips with the 5.8 mm and 7.04 mm diameter coils, respectively. The devices incorporate polyimide coatings above and below each layer to physically encapsulate the copper traces and place them near the neutral mechanical plane to minimize bending induced strains (FIG. 2d, e). The NFC dies connect via a modified flip-chip technique to contacts located near the center regions of the coils. Certain device variants also include small-scale light emitting diodes (LEDs, 0402 size: 1 mm×0.5 mm). Here, energy harvested and rectified during communication within NFC ISO protocols enables operation of the LEDs and the NFC chips simultaneously. In all cases, a thin silicone elastomer (~25 µm) encapsulates the system, and a low modulus acrylic adhesive (~25 µm) serves as the substrate. The ultraminiaturized, thin, lightweight construction provides wide ranging options for mounting on the human body, including locations where long-term integration is possible and where interfaces to both the body and an external device are easily established.

Figure 3:
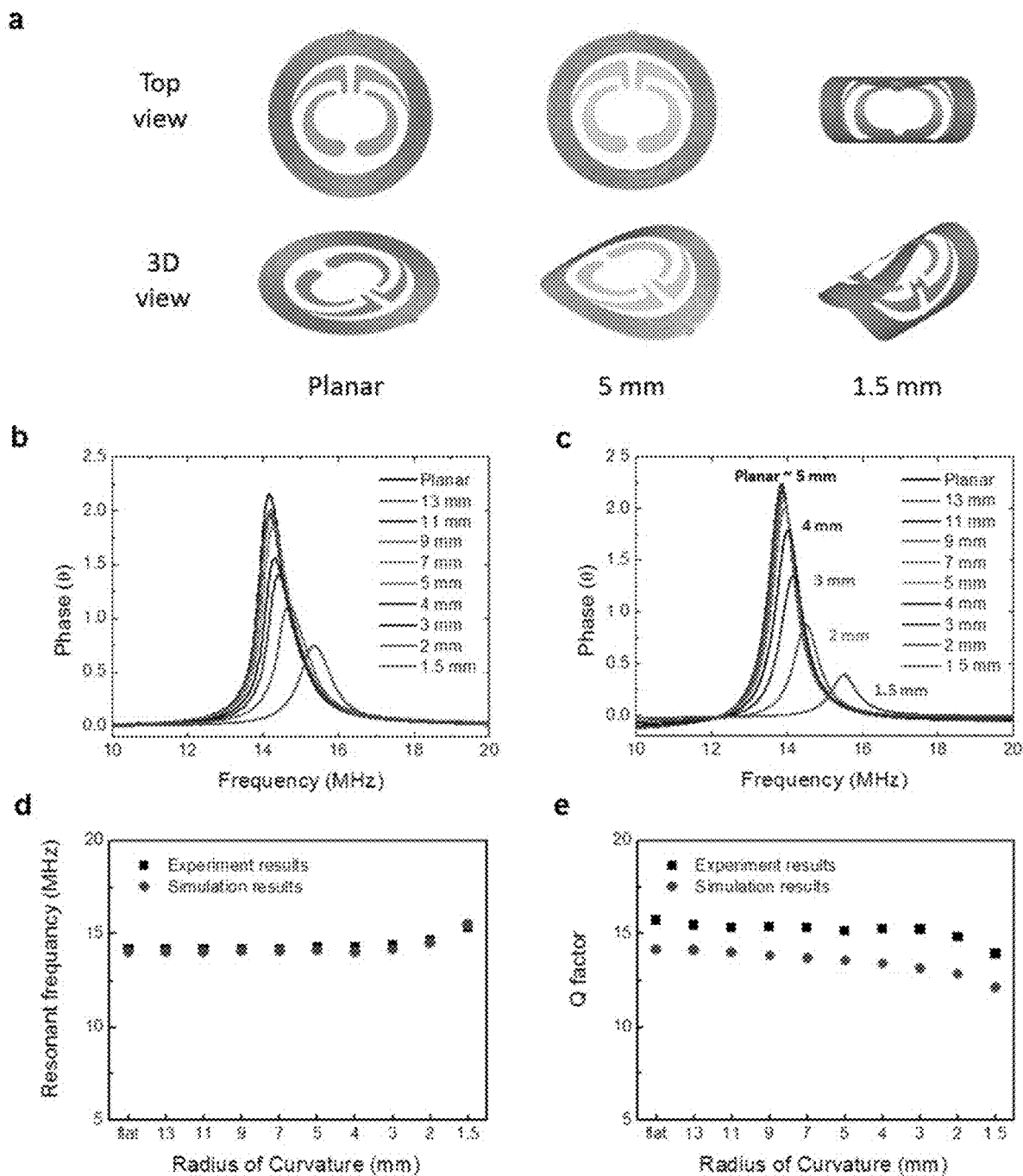
FIG. 3. Experimental and simulation results for the electromagnetic properties of flexible mm-NFC devices bent to different radii of curvature. (a) Top view and 3D illustrations of devices at different curvatures. (b) Measured phase responses of the coils as a function of radius of curvature and (c) corresponding simulation results. (d) Measured and simulated changes in resonant frequency with radius of curvature. (e) Measured and simulated changes in Q factor with radius of curvature.
Figure 7:
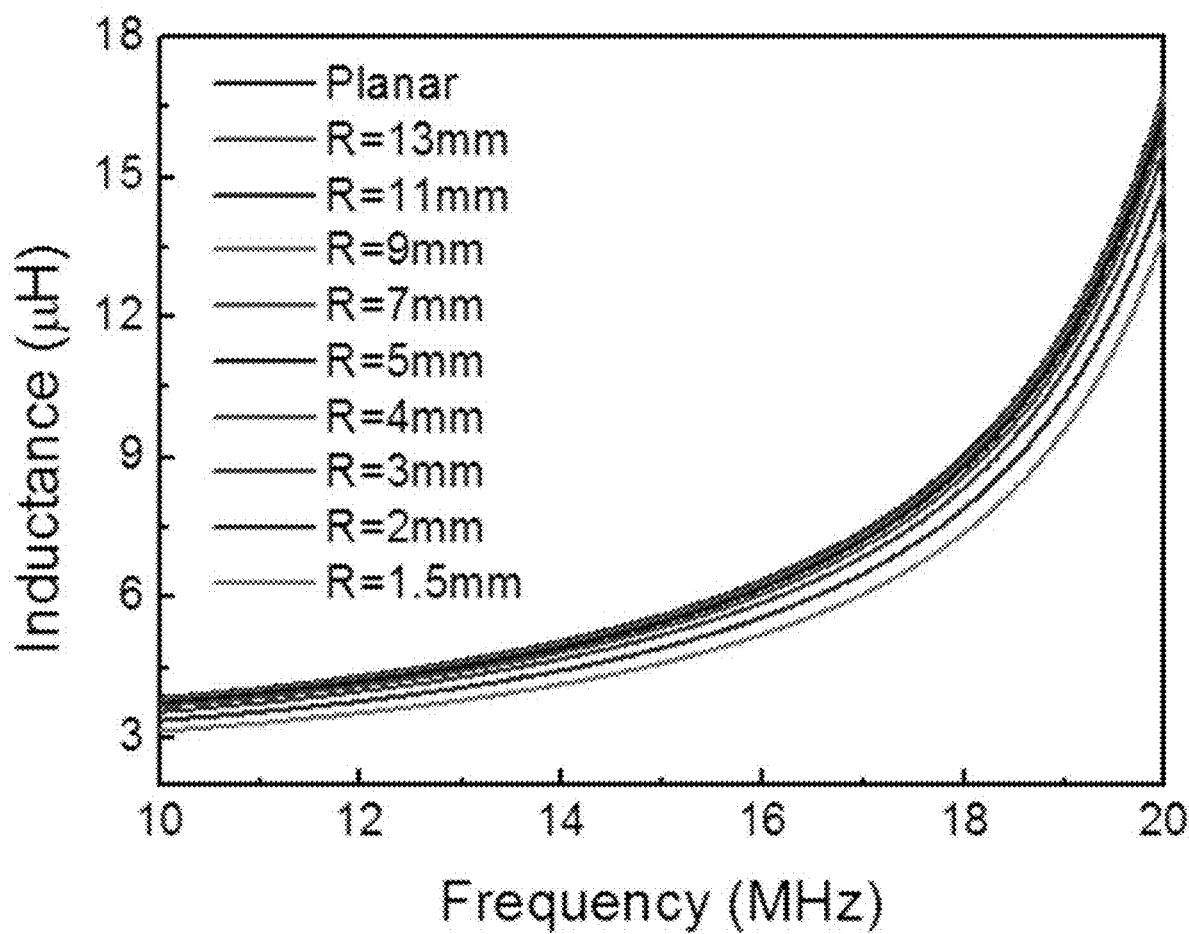
FIG. 7. The effective inductance of the coil of mm-NFC devices with different bending radii of curvature to determine the shift of resonance frequency.

The fingernails and toenails provide examples. By comparison to the skin, the nails are hard, physically static and they lack sensory capacity, thereby providing a minimally invasive interface for robust, long-term integration. The growth cycle from the quick to the end of the nail can exceed 6 months, thereby allowing integration for several months[11]. Such timeframes greatly exceed those associated with mounting on the skin, where the cycle for skin cell differentiation and exfoliation occurs on the timescale of a few weeks. The fingernails of adults have radii of curvature that range from ~13 mm to ~5 mm, depending on age, sex, overall body size, and finger[12]. Properly designed devices can accommodate bending associated with mounting on such surfaces, without significant change in operating characteristics. FIG. 3 shows the electromagnetic properties of mm-NFC devices at bending curvatures relevant to the fingernail. These evaluations use the largest device (7.04 mm coil diameter) because this format involves the most significant change at any given curvature. In all cases, resonance frequencies measured by the Min-phase method[13] match those determined by electromagnetic simulations (Ansys HFSS 13 User's guide, Ansys Inc. 2011). Typically, the frequencies increase with bending radii due to decreases in the projected areas and the associated inductances. The magnetic flux through the coil of the mm-NFC device is $\Phi=\iint_S B \cdot dS$, where B is magnetic field produced by the primary coil and S is the corresponding in-plane area enclosed by the coil of the mm-NFC device. For a large commercial primary coil (Samsung Galaxy Note II), the magnetic field B remains essentially the same when the small mm-NFC devices are bent, such that the magnetic flux $\Phi$ depends only on the effective area S of the coil of the mm-NFC device. The change of effective area S is $(d/R)^2/32$, where d is the inner diameter of the mm-NFC device and R is the radius of curvature. For the mm-NFC device with 7.04 mm outer diameter d=~5 mm as in experiments and R>5 mm for the adult human fingernails, the effective area S only decreases by ~3.1% for R=5 mm. The magnetic flux therefore also remains unchanged when the mm-NFC devices are mounted onto the fingernails, as confirmed by FIG. 3a. The resonance frequency can be obtained from $f_{resonant}=1/(2\pi\sqrt{L(f_{resonant},R)C})$, where C is the capacitance of the NFC die, and the effective inductance L of the coil of the mm-NFC device depends on the frequency f and radius of curvature R as shown in FIG. 7. The maximum difference between the effective inductance for a planar coil and one with a radius of curvature of 5 mm is only ~3% as shown in FIG. 7. By consequence, the resonance frequencies and the Q factors remain ~14 MHz and ~15, respectively, for a bending radius R>~5 mm. Changes can be observed when R becomes significantly smaller than 5 mm, as shown in FIG. 3d, e.

Figure 8:
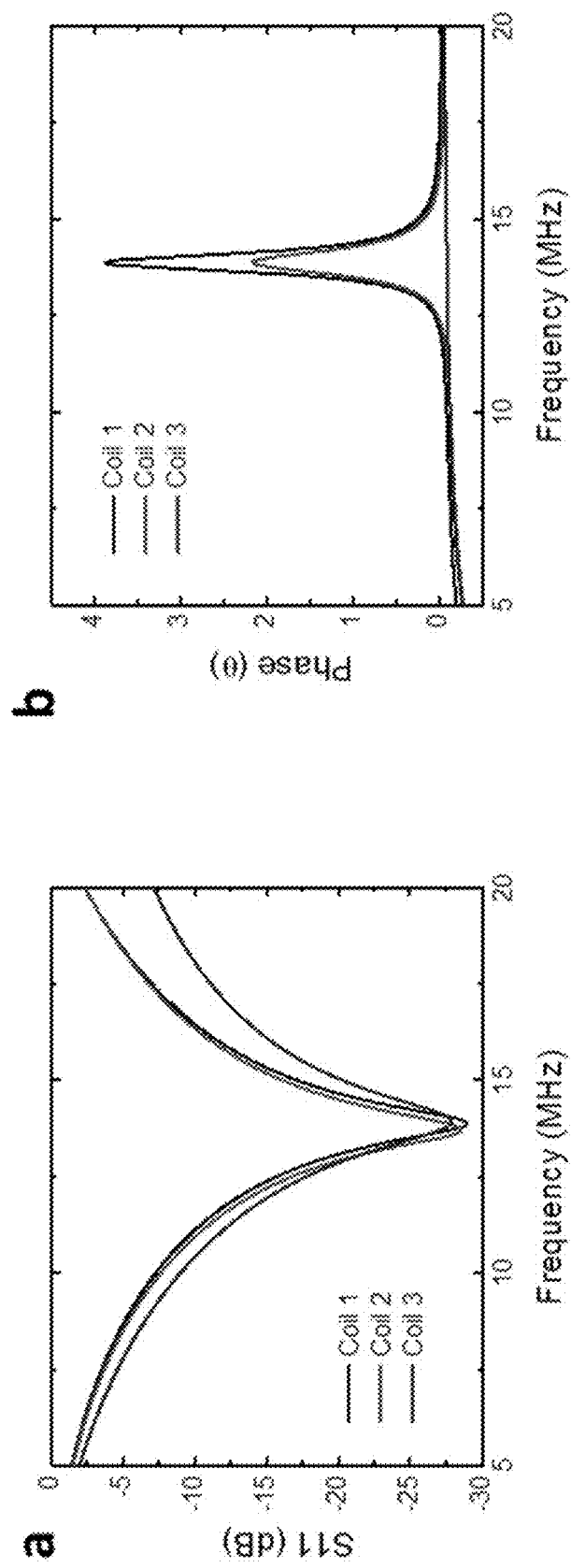
FIG. 8. (a) The return loss spectra for three mm-NFC devices. (b) The change of the phases of primary coil to analyze the size effect of the mm-NFC device on the communication between the primary coil and mm-NFC device.

The electromagnetic coupling between a primary coil and an mm-NFC device depends strongly on size, as expected from the expression for magnetic flux. Three mm-NFC devices with different radii given in Table 1 are studied, where the number of turns and layers are adjusted to offer the same inductances, i.e., these mm-NFC devices have the same resonant frequency and Q factor as shown in Table 1 and return loss spectra as shown in FIG. 8a. As the size of mm-NFC device decreases, the amplitude of phase decreases rapidly as shown in FIG. 8b, which suggests that the communication between the primary coil and mm-NFC device weakens significantly as the coil size of an mm-NFC device decreases.

TABLE 1

Three mm-NFC devices with different radii

| | Diameter (mm) | Layers | Turns/ layer | Resonant frequency $f_0$ | Inductance at $f_0$ (µH) | Q factor at $f_0$ |
|---|---|---|---|---|---|---|
| Coil 1 | 7.76 | 2 | 8 | 13.88 MHz | 4.76 | 13.9 |
| Coil 2 | 7.04 | 2 | 9 | 13.72 MHz | 4.87 | 13.4 |
| Coil 3 | 4 | 4 | 8 | 13.93 MHz | 4.73 | 12.3 |

Figure 4:
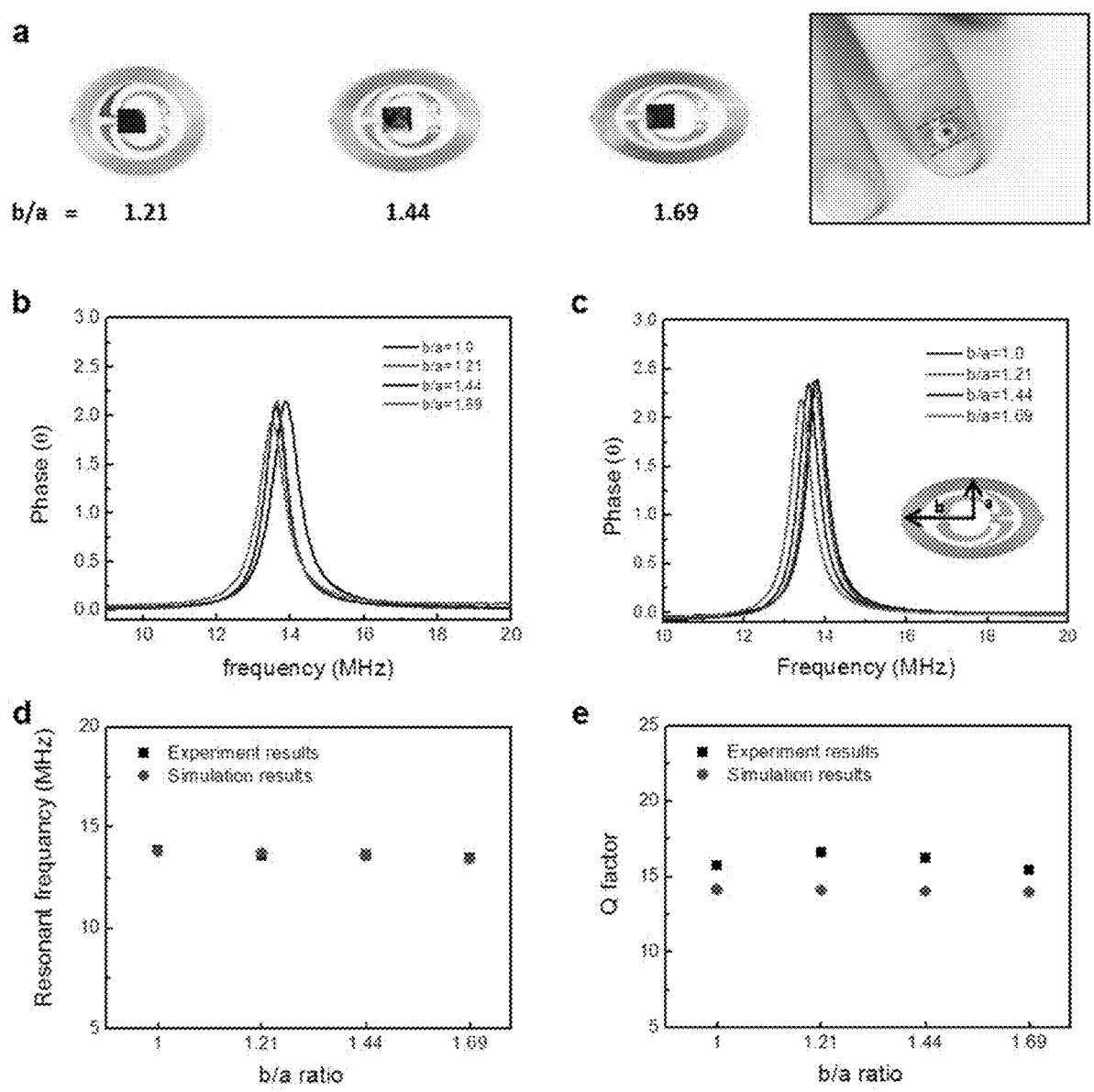

The nature of fingernail growth affords increased mounting times for mm-NFC devices that adopt elliptical shapes with major axes oriented parallel to the base of the nail. FIG. 4 shows the results for mm-NFC devices with such shapes and with areas similar to those of circular designs ($\pi R^2$), for several different aspect ratios b/a=1.21, 1.44, and 1.69, with the major axes a and b shown in FIG. 4c. The resonance frequency and the amplitude of the phase decrease only slightly as the aspect ratio b/a increases as shown in FIG. 4b, c. As a result, the resonance frequencies and the Q factors remain essentially unchanged, i.e. 14 MHz and 15, respectively, for this range of aspect ratios (FIG. 4d, e).

Figure 5:
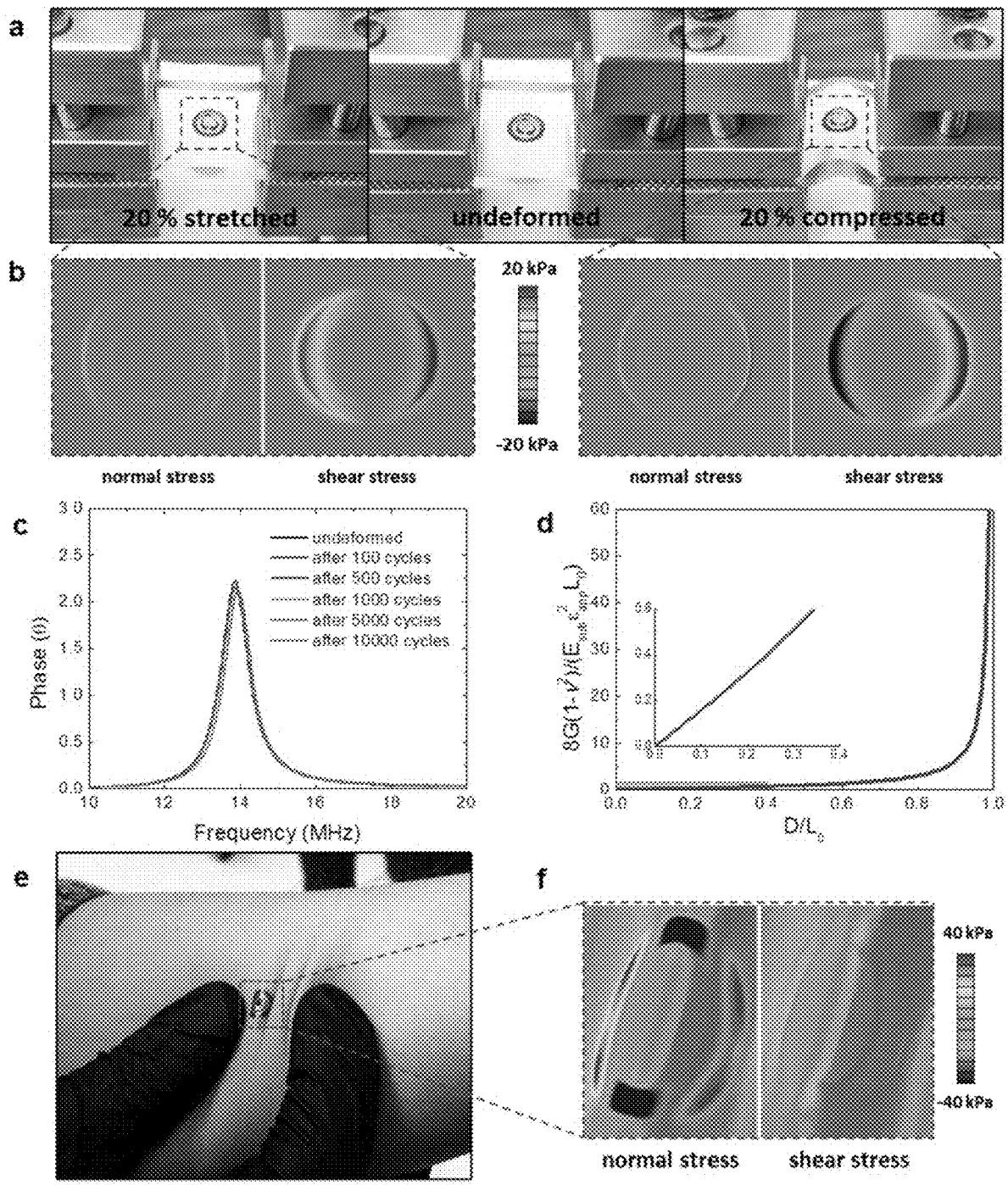
FIG. 5. Experimental and simulation results of the mechanical responses of flexible mm-NFC devices to applied strain. (a) Pictures of a representative device mounted onto a soft silicon substrate that is undeformed (center), stretched (left) and compressed (right) by application of force using a mechanical stage. (b) The bottom frames show corresponding FEA results of applied stresses. (c) Phase responses measured after different numbers of cycles of uniaxial stretching (to 20%)/compressing (to 20%). (d) Plot of the energy release rate with the diameter of mm-NFC device. (e) Picture of a device mounted on the skin during a pinching mode deformation. (f) Simulated stress distributions near the device.

Flexible mm-NFC devices also offer advantages for mounting on the skin. Here, the small sizes minimize sensory perception and reduce energy release rates for delamination. FIG. 5a shows images of a device with 7.04 mm outer diameter printed onto a low modulus substrate (PDMS, 20 mm length in stretching direction, 25 mm width, 3 mm thick, 0.145 MPa modulus) in various deformed states, including tests that involve stretching to 20% and compressing to 20%, repeatedly. Even after 10,000 cycles, the device shows no form of degradation in properties (FIG. 5c). FIG. 5b presents the stress distributions at the interface between the substrate and mm-NFC device obtained from finite element analysis (ABAQUS Analysis User's Manual 2010, V6.10). For both stretching and compressing, the normal stress is negligibly small as compared to the shear stress at the interface; the latter is smaller than the threshold (20 kPa)[14] for somatosensory perception of forces by normal skin under 20% stretching. For compressing by 20%, which is larger than that expected in most practical applications, the shear stress exceeds the threshold 20 kPa over a small region (~4 mm$^2$) of the interface. The energy release rate[15] for an infinitesimal crack at the edge is $$G = \frac{E_{sub}\varepsilon_{app}^2}{8(1-v_{sub}^2)} L_0 \tan\frac{\pi D}{2L_0},$$

where D is the diameter of the mm-NFC device, $L_0$ is the length of substrate in the stretching direction, $\varepsilon_{app}$ is the average strain in the substrate, and $E_{sub}$ and $v_{sub}$ are the Young's modulus and Poisson's ratio of the substrate, respectively. As shown in FIG. 5d, the energy release rate clearly decreases with the coil diameter D, and becomes linear with respect to D for small mm-NFC devices, i.e.

$$G = \frac{\pi D E_{sub}\varepsilon_{app}^2}{16(1-v_{sub}^2)}.$$

This scaling affords advantages in the reduced possibility for delamination of mm-NFC devices from the skin. FIG. 5e, f show the picture of a device mounted on the skin during a pinching mode deformation and the stress distributions at the interface from finite element analysis, respectively. The device is fully bonded with the skin even when the skin is subjected to severe wrinkle. Minimizing the size maximizes the robustness of the device/skin bonding interface for any given adhesive strategy and device construction.

Figure 6:
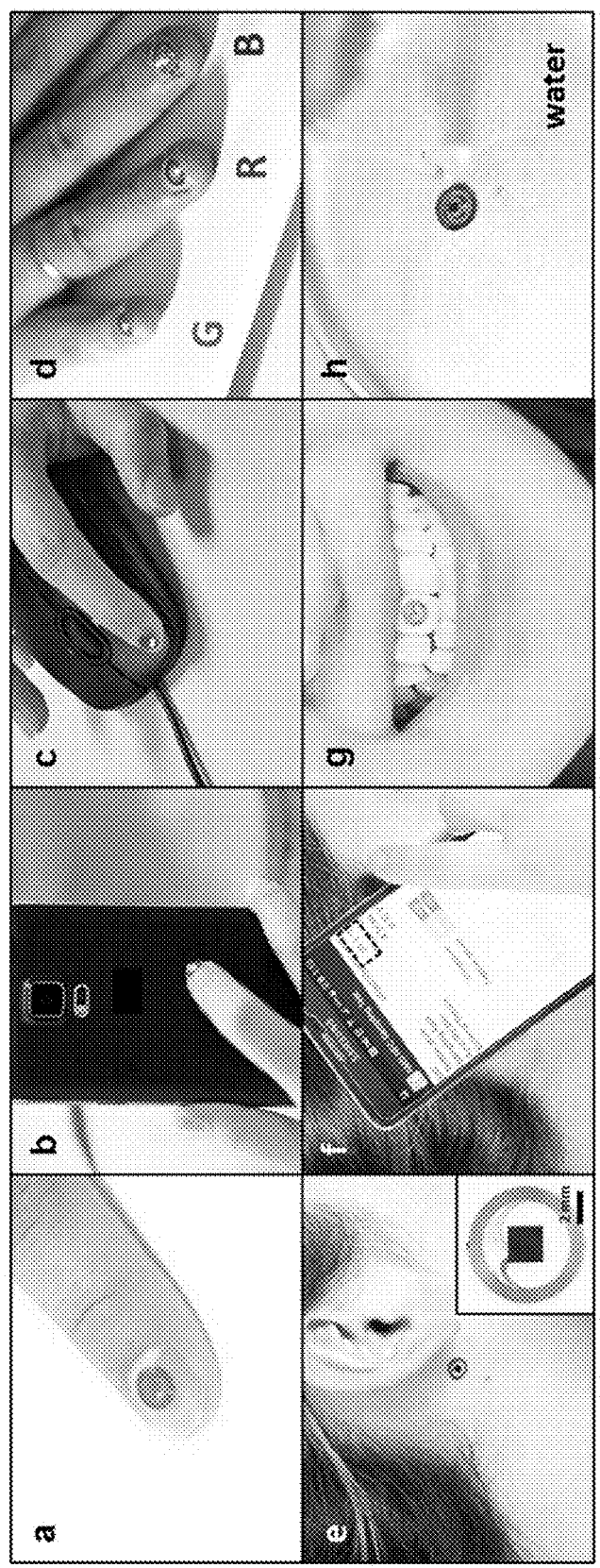
FIG. 6. Pictures of various points of integration of mm-NFC devices on the body, each suggestive of a different application possibility. (a) Picture of a device on the fingernail. Pictures of applications to unlock a (b) smartphone and (c) computer (using a mouse). (d) Picture of a set of devices with integrated LEDs mounted on the fingernails. (e, f) Pictures of a device mounted on the skin behind the ear, with integrated temperature sensing capabilities. (inset) Picture of a device that enables temperature sensing. Pictures of devices (g) on a tooth and (h) submerged in water.

FIG. 6 presents images of devices mounted on various locations of the body, each suggestive of a possible application. FIG. 6a shows an mm-NFC device on the fingernail, such that, for example, natural motions associated with handling the phone could unlock its operation, as shown in FIG. 6b. This type of authentication could be useful in many contexts (FIG. 6c). Multiple devices with different purposes can easily be accommodated in one convenient area (FIG. 6d). Certain NFC die (SL13A, AMS AG) offer integrated capabilities in temperature sensing and other functionality. The inset of FIG. 6e shows an mm-NFC device for temperature sensing. In this case, a skin-integrated configuration could be useful (FIG. 6e, f). The devices can also function properly on teeth and under water (FIG. 6g, h), thereby supporting modes for chemical sensing in biofluids.

Conclusion

The materials, device designs and integration strategies presented here provide a framework for mm-scale, flexible, body-worn NFC systems, with potential applications in password authentication, electronic transactions and biometric sensing. The ultraminiaturized geometries and mechanically flexible designs, in particular, afford advantages in mechanical strength, placement versatility, and minimized interfacial stresses. Combined theoretical and experimental considerations in materials, electromagnetic characteristics and mechanical properties are essential to proper design. These concepts can apply to many other types of wireless communication systems including various bio-sensors and electronic implants.

Experimental Section

Fabrication of the Coils:

A Cu foil (18 μm thick, Oak Mitsui Micro-thin series) served as the material for the first coil layer. A layer of polyimide (2.4 μm thick, PI2545, HD Microsystems) spin-cast at 2000 rpm for 30 s, baked on a hot plated at 150° C. for 5 min, and in a vacuum oven at 250° C. for 70 min formed an insulating coating. Laminating this PI-coated Cu foil onto a glass slide coated with polydimethylsiloxane (PDMS, Sylgard 184), with the PI side down, allowed patterning of the Cu into a coil geometry by photolithography (AZ 4620 photo-resist, spin-casting at 3000 rpm for 30 s, baking at 110° C. for 3 mins, UV irradiance for 300 mJ/cm$^2$, development for ~40 s with developer AZ 400K/deionized water solution of 1:2 volume ratio) and wet etching (CE-100 copper etchant, Transense, etching for ~10 mins with frequent rinsing by water). A coating of PI spin-cast at 1000 rpm for 30 s covered the first coil layer. Photolithography (AZ 4620) and oxygen plasma etching created via holes through the PI. Oxide remover (Flux, Worthington) eliminated the native copper oxide at the base of via holes. Electron beam evaporation formed a conducting layer (500 nm thick) for electroplating. Next, electroplating (11 wt % cupric sulfate pentahydrate in water, current of 13 mA/cm$^2$ for 55 mins, distance between positive electrode and negative electrode of 1.7 cm) generated a second coil in a 20 μm thick layer of Cu, also patterned by photolithography (AZ 4620) and wet etching (copper etchant). Spin casting formed another 2.4 μm thick layer of PI over the entire coil structure. Electron beam evaporation of a 50 nm thick layer of SiO$_2$ created a hard mask in a geometry defined by photolithography (AZ 4620) and RIE etching (50 mTorr, 40 sccm CF$_4$, 100 W for 10 min). Oxygen plasma removed the exposed PI, leaving PI only in the regions of the coil, for an open architecture design that improves the mechanical deformability.

NFC Die:

The NTAG216 (NXP Semiconductor, ISO/IEC 14443, input capacitance of 50 pF) chip served as the electronics for the smallest device. The M24LR04E (ST Microelectronics, ISO/IEC 15693, input capacitance of 27.5 pF) chip was used for the energy harvesting device. The SL13A (AMS AG, ISO/IEC 15693, input capacitance of 25 pF) chip enabled the temperature sensing device. All chips were thinned (<100 μm thick) and used as bare die without packages.

Transfer and Chips Assembly:

A cellulose-based water-soluble tape (Grainger) allowed retrieval of the fabricated coils from the substrate and integration onto an adhesive substrate. Removal of the water-soluble tape by dissolution in water completed the transfer. Thinned NFC die and LEDs attached to the coil by a modified flip-chip bonding method with an Indium/Ag based solder paste (Ind. 290, Indium Corporation; ~165° C. for 2 min in a reflow oven). A droplet of silicone elastomer (Q1-4010, Dow corning) encapsulated the chips.

Figure 9:
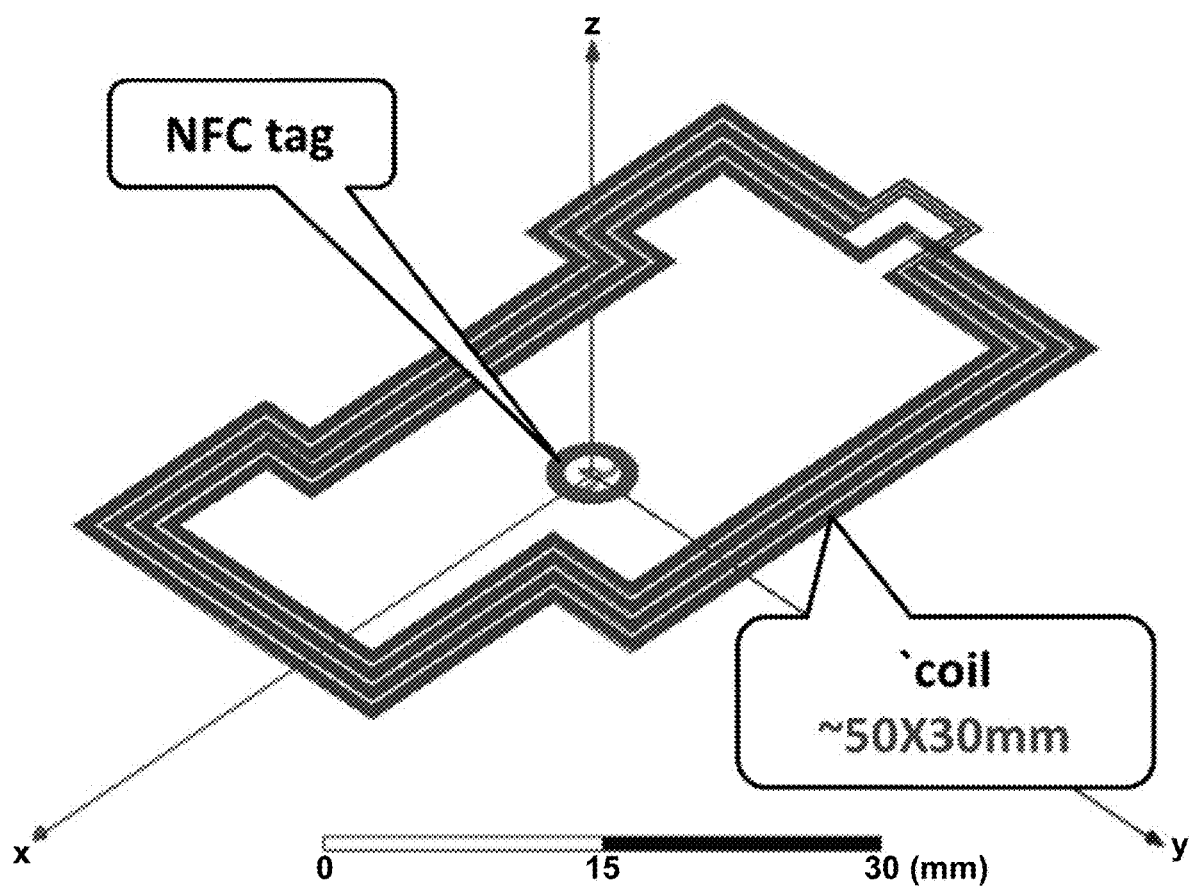
FIG. 9. The illustration of the primary coil and the mm-NFC device for measurement. The mm-NFC device is located at the center of the primary coil at the vertical distance of ~2 mm.

Electromagnetic Characterization:

Electromagnetic characterization used an impedance analyzer (4291A RF impedance/material analyzer, Hewlett Packard) with a commercial primary coil (Samsung Galaxy Note II; resonant frequency ~47.5 MHz) over a frequency range of 5 to 20 MHz. The Min-phase method defined the resonance frequencies of the NFC devices. Measurements involved placement of the device at the center of the primary coil at a vertical distance of ~2 mm, as shown FIG. 9.

REFERENCES

[1] H. P, H. J, 2015; G. B. Raupp, Ecs Transactions 2011, 37, 229.
[2] J. Kim, A. Banks, H. Y. Cheng, Z. Q. Xie, S. Xu, K. I. Jang, J. W. Lee, Z. J. Liu, P. Gutruf, X. Huang, P. H. Wei, F. Liu, K. Li, M. Dalal, R. Ghaffari, X. Feng, Y. G. Huang, S. Gupta, U. Paik, J. A. Rogers, Small 2015, 11, 906.
[3] J. Sidén, V. Skerved, J. Gao, S. Forsström, H.-E. Nilsson, T. Kanter, M. Gulliksson, "Home care with nfc sensors and a smart phone", presented at *Proceedings of the 4th International Symposium on Applied Sciences in Biomedical and Communication Technologies*, 2011.
[4] D. H. Kim, N. S. Lu, R. Ma, Y. S. Kim, R. H. Kim, S. D. Wang, J. Wu, S. M. Won, H. Tao, A. Islam, K. J. Yu, T. I. Kim, R. Chowdhury, M. Ying, L. Z. Xu, M. Li, H. J. Chung, H. Keum, M. McCormick, P. Liu, Y. W. Zhang, F. G. Omenetto, Y. G. Huang, T. Coleman, J. A. Rogers, Science 2011, 333, 838.
[5] S. Xu, Y. H. Zhang, L. Jia, K. E. Mathewson, K. I. Jang, J. Kim, H. R. Fu, X. Huang, P. Chava, R. H. Wang, S. Bhole, L. Z. Wang, Y. J. Na, Y. Guan, M. Flavin, Z. S. Han, Y. G. Huang, J. A. Rogers, Science 2014, 344, 70; J. R. Windmiller, A. J. Bandodkar, G. Valdes-Ramirez, S. Parkhomovsky, A. G. Martinez, J. Wang, Chem Commun 2012, 48, 6794.
[6] K. I. Jang, H. U. Chung, S. Xu, C. H. Lee, H. Luan, J. Jeong, H. Cheng, G. T. Kim, S. Y. Han, J. W. Lee, J. Kim, M. Cho, F. Miao, Y. Yang, H. N. Jung, M. Flavin, H. Liu, G. W. Kong, K. J. Yu, S. I. Rhee, J. Chung, B. Kim, J. W. Kwak, M. H. Yun, J. Y. Kim, Y. M. Song, U. Paik, Y. Zhang, Y. Huang, J. A. Rogers, Nat Commun 2015, 6, 6566; J. W. Jeong, W. H. Yeo, A. Akhtar, J. J. S. Norton, Y. J. Kwack, S. Li, S. Y. Jung, Y. W. Su, W. Lee, J. Xia, H. Y. Cheng, Y. G. Huang, W. S. Choi, T. Bretl, J. A. Rogers, Adv Mater 2013, 25, 6839.
[7] M. Q. Saeed, C. D. Walter, 2012 International Conference for Internet Technology and Secured Transactions 2012, 730.
[8] M. Fisher, Google Patents, 2013.
[9] D. P. Rose, M. Ratterman, D. K. Griffin, L. Hou, N. Kelley-Loughnane, R. R. Naik, J. A. Hagen, I. Papautsky, J. Heikenfeld, 2014; E. Freudenthal, D. Herrera, F. Kautz, C. Natividad, A. Ogrey, J. Sipla, A. Sosa, C. Betancourt, L. Estevez, 2007.
[10] A. nidaršič, B. Werber, 2014; D. Things, Vol. 2014, 2014.
[11] W. B. Bean, Arch Intern Med 1980, 140, 73.
[12] S. Murdan, Int J Cosmetic Sci 2011, 33, 509.
[13] T. J. Harpster, B. Stark, K. Najafi, Sensor Actuat a-Phys 2002, 95, 100; X. Huang, Y. H. Liu, H. Y. Cheng, W. J. Shin, J. A. Fan, Z. J. Liu, C. J. Lu, G. W. Kong, K. Chen, D. Patnaik, S. H. Lee, S. Hage-Ali, Y. G. Huang, J. A. Rogers, Adv Funct Mater 2014, 24, 3846.
[14] S. D. Wang, M. Li, J. Wu, D. H. Kim, N. S. Lu, Y. W. Su, Z. Kang, Y. G. Huang, J. A. Rogers, J Appl Mech-T Asme 2012, 79.
[15] N. S. Lu, J. I. Yoon, Z. G. Suo, Int J Mater Res 2007, 98, 717.

Example 2—Fingernail Mounted NFC Device for Password Authentication

The invention provides, for example, a fingernail mounted near field communication (NFC) device providing a unique solution for password authentication in the electronic hardware industry. The materials, design, and circuit integration enable the art of biocompatible NFC technology. The built-in NFC technology serves as a digital replacement for passwords, pin numbers, security questions, distinct biometrics, and/or text/email verification dealings. The fingernail-mounted device of this embodiment is able to wirelessly communicate with point of access readers that use NFC antennas. The point of access readers include but are not limited to smartphones, laptops, keyboards, computer mice, remote controls, safes, and/or locks. Instead of recalling passwords, fingerprint touch pads, or safe combinations, authorized fingernail-mounted device users are granted instant access to their electronics and/or safe belongings without producing security passcodes.

In some embodiments, for example, the invention has a devoted chip that stores an encrypted identification number that is unique to each individual device. In addition, the chip has action-specific security codes that change after each point of authorization. The encrypted identification numbers grant access to authorized users. For instance, the authorized user goes straight to his or her home screen once the reader detects the invented hardware. If the encrypted identification numbers do not appropriately match, the foreign user is denied access.

For privacy, individual users are not at risk of exposing their personal information, passwords, pins, biometrics, and/or access restrictions to by-standers. Customers do not have to waste time typing passwords or pins to gain access to their personal electronics. Fingernail mounted devices are waterproof and remainoperational for several days or months. The invention is able to work in conjunction with mobile phone or computer applications developed specifically for authentication purposes. If removed from the nail or tissue, the invented device is permanently disabled and all private information is destroyed.

Figure 10:
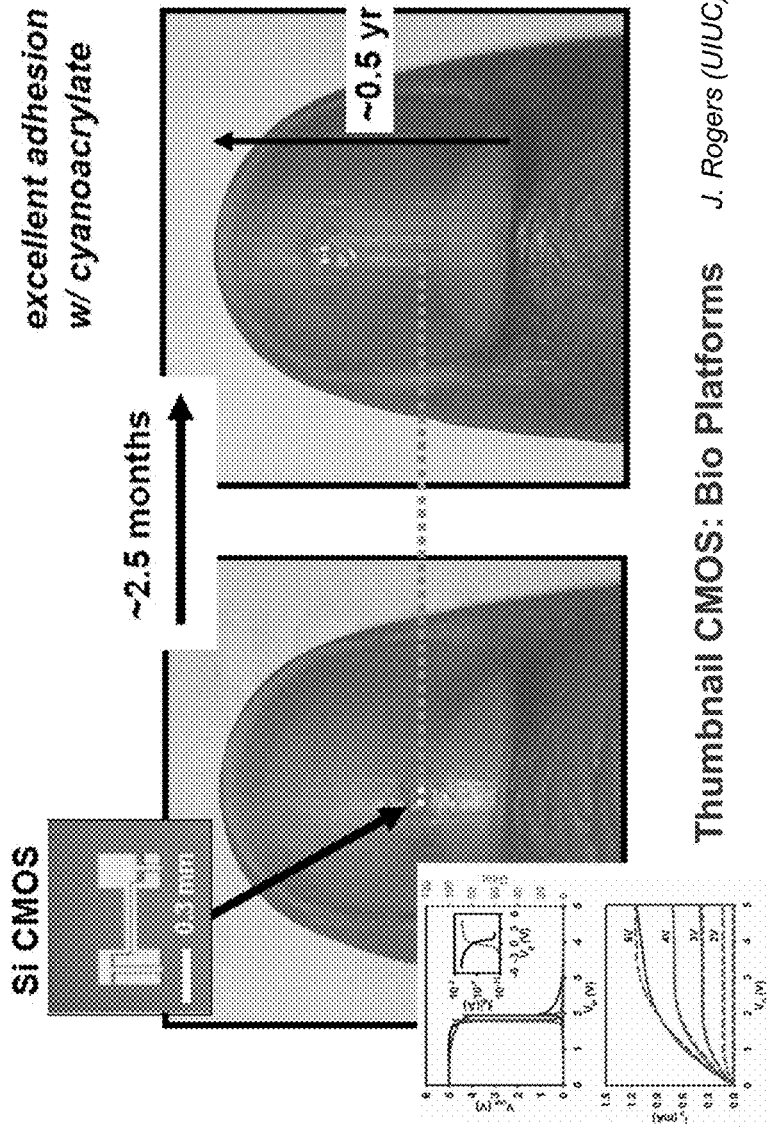
FIG. 10 provides images and experimental results characterizing a fingernail mounted silicon CMOS device. Bonding to the surface of fingernail is provided by cyanoacrylate providing excellent adhesion. The plots provided demonstrate good electronic performance achieved for a timeframe of about 2.5 months.

FIG. 10 provides images and experimental results characterizing a fingernail mounted silicon CMOS device. Bonding to the surface of fingernail is provided by cyanoacrylate providing excellent adhesion. The plots provided demonstrate good electronic performance achieved for a timeframe of about 2.5 months.

FIG. 11 provides images of fingernail authentication device designs. The panel to the left shows a fingernail mounted system comprising NFC coils and NFC chip components provided in a miniaturized format. The panel to the right shows a fingernail mounted system further comprising an energy harvesting LED indicator also provided in a miniaturized format.

Figure 12:
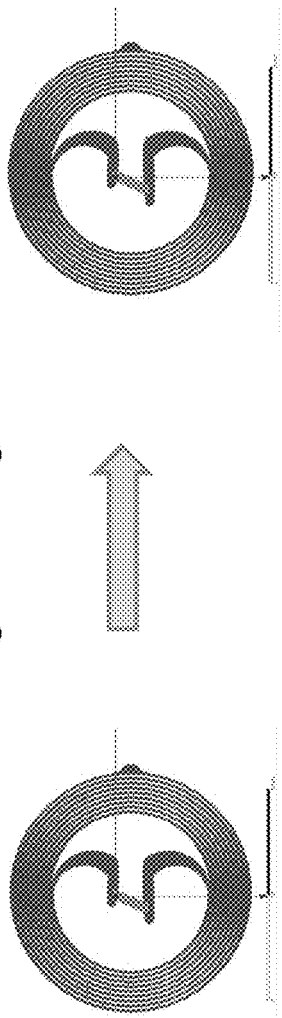
FIG. 12 provides a summary of design information characterizing the calculated Q factor for NFC fingernail mounted systems. As shown in this figure the Q factor is dependent on a number of variables including the thickness and diameter of the NFC coils. High Q factor is beneficial for communication with a mobile electronic device, such as a cell phone.

FIG. 12 provides a summary of design information characterizing the calculated Q factor for NFC fingernail mounted systems. As shown in this figure the Q factor is dependent on a number of variables including the thickness and diameter of the NFC coils. High Q factor is beneficial for communication with a mobile electronic device, such as a cell phone.

Figure 13:
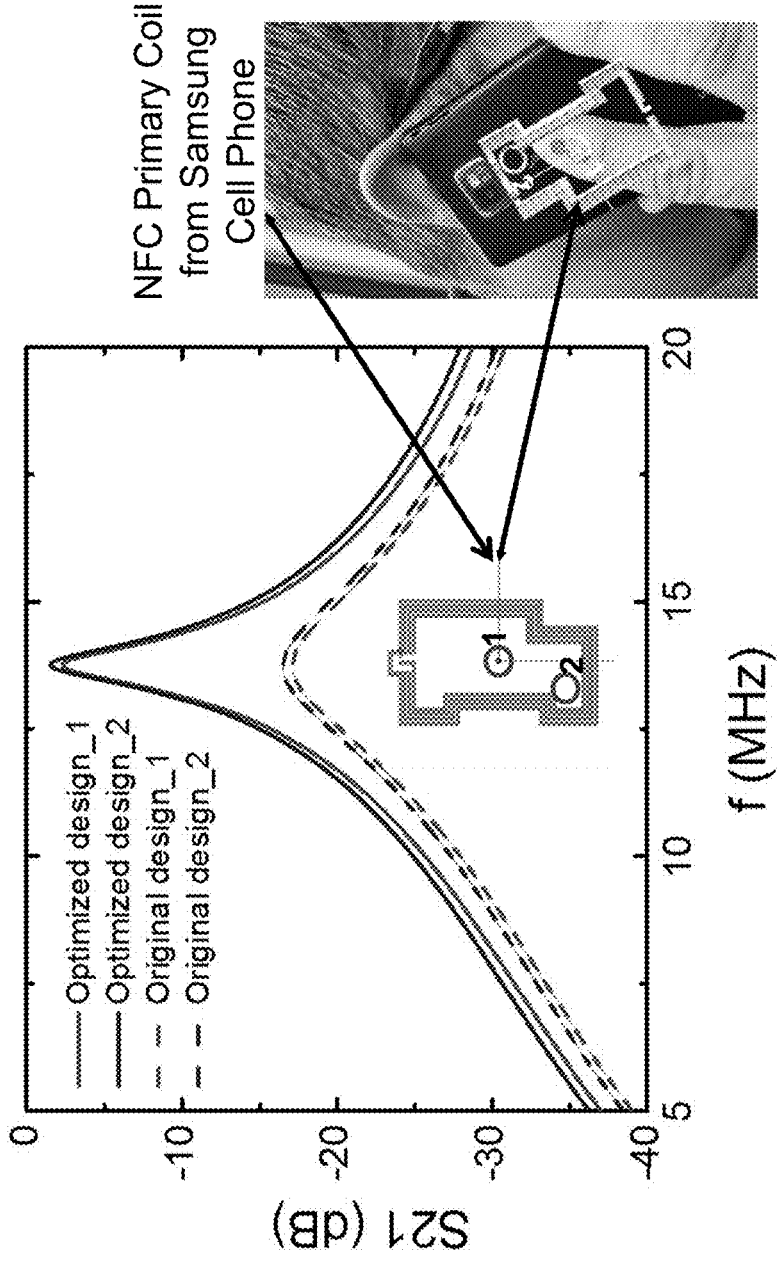
FIG. 13 provides a plot of S21 (dB0) as a function of frequency for a series of NFC fingernail mounted system designs. The S21 represents the power transferred between the primary NFC coil from a Samsung cell phone and the secondary NFC coil from the fingernail mounted NFC system. The distance between the primary and secondary coils is set at 5 mm.

FIG. 13 provides a plot of S21 (dB0) as a function of frequency for a series of NFC fingernail mounted system designs. The S21 represents the power transferred between the primary NFC coil from a Samsung cell phone and the secondary NFC coil from the fingernail mounted NFC system. The distance between the primary and secondary coils is set at 5 mm.

Figure 14:
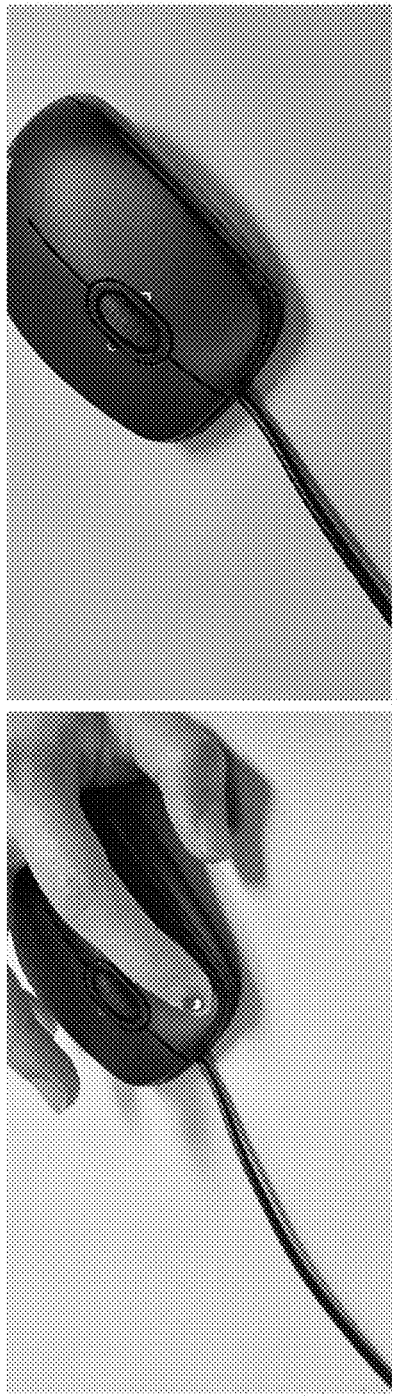
FIG. 14 shows a fingernail mounted NFC system for use in conjunction with a mouse for authentication of a user to a computer.

FIG. 14 shows a fingernail mounted NFC system for use in conjunction with a mouse for authentication of a user to a computer.

Figure 15:
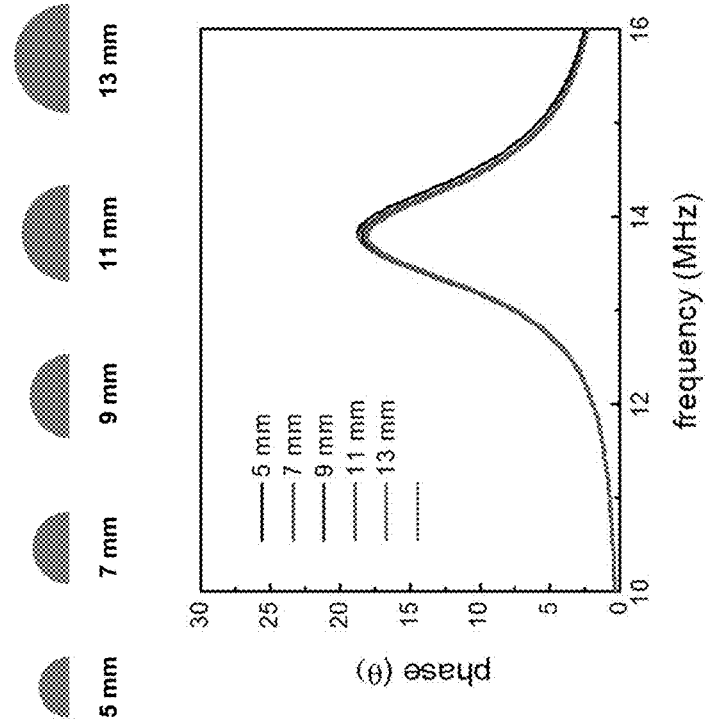
FIG. 15 provides a summary of electromagnetic properties as a function of the radius of curvature. These results demonstrate that the fingernail mounted NFC systems operate at similar ranges regardless of fingernail curvature.

FIG. 15 provides a summary of electromagnetic properties as a function of the radius of curvature. These results demonstrate that the fingernail mounted NFC systems operate at similar ranges regardless of fingernail curvature.

Figure 16:
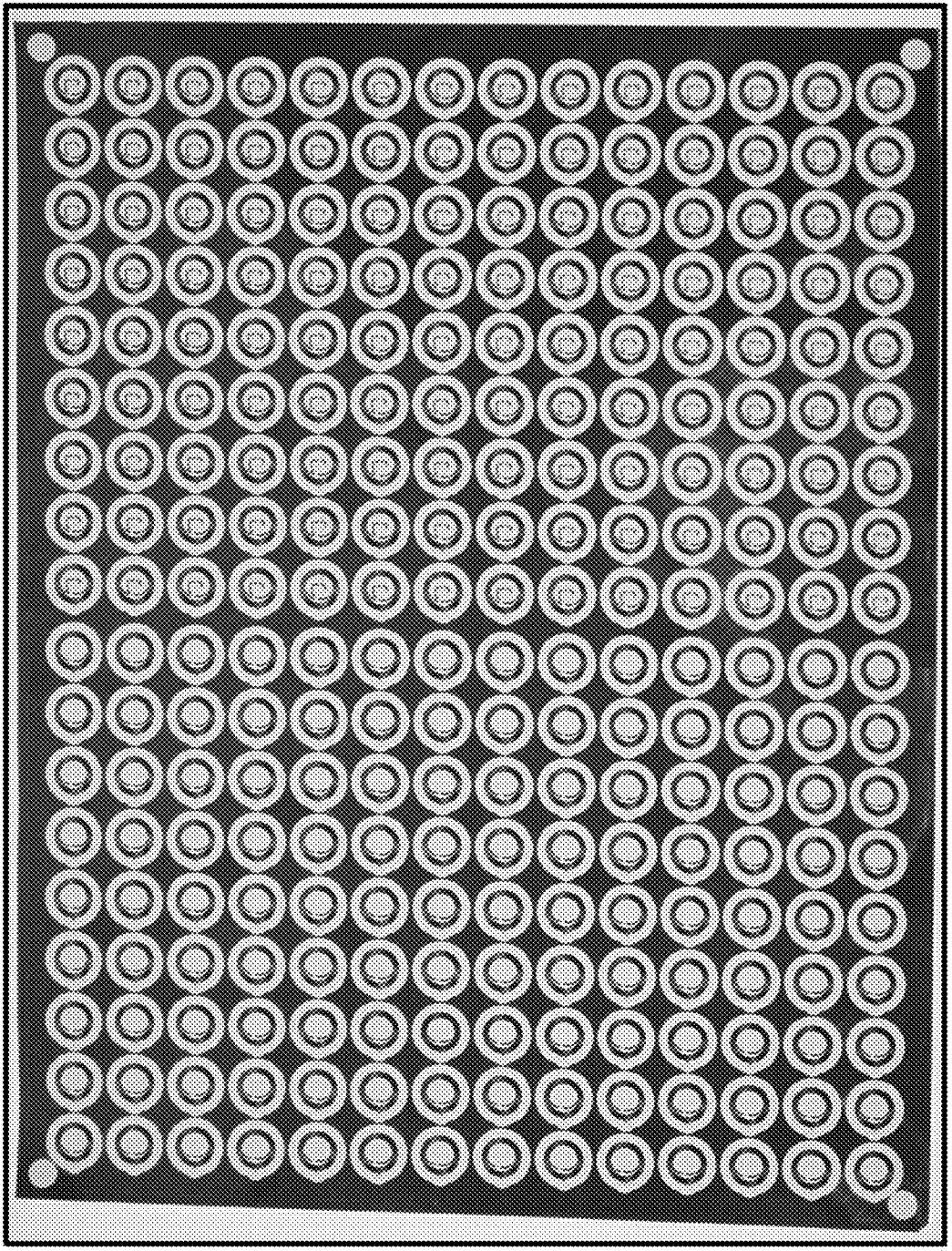
FIG. 16 provides an image of a 6" by 9" test panel comprising 252 NFC systems of the invention for tissue mounting applications.

FIG. 16 provides an image of a 6" by 9" test panel comprising 252 NFC systems of the invention for tissue mounting applications.

Beneficial aspects of the present fingernail mounted systems of the invention include:
- Ultrathin, flexible, open architecture (one-size-fits-all construction)
- Designs for stable operation under sharp bending
- Strategies for robust interface adhesion
- Designs to prevent removal and re-use
- Materials for operation under extreme conditions
- Configurations for flexibility in mounting locations
- Layouts for options in graphics overlays
- Coils for operation of multiple devices Example 3—Fingernail Mounted NFC Device for Electronic Payments The invention provides, for example, fingernail mounted near field communication (NFC) devices providing a unique platform for mobile payment and digital wallet service providers. The materials, design, and circuit integration enable the art of biocompatible NFC technology. In some embodiments, the built-in NFC technology serves as a digital replacement for the magnetic strip found on the back of all debit, credit, and prepaid gift cards. The fingernail-mounted device is able to wirelessly communicate with point of sale readers that use NFC antennas. Instead of exchanging cash, debit or credit cards, users have the ability to make secure in-store purchases with a single touch or point. Additional payment schemes using the fingernail-mounted device include device and pin, a combination of the devices, or a combination of the device and a second method for authorization.

In an embodiment, for example, the invention has a devoted chip that stores encrypted payment information that is unique to each individual device. In addition, the chip has transaction-specific security codes that change after each transaction. The encrypted payment information and varying security codes are used to process each transaction at time of purchase. In some embodiments, the payment information is never shared with merchants or stored on a server. In some embodiments, all financial information is stored locally on the consumers' personal mobile devices and/or computers.

In some embodiments, for privacy, the invented hardware does not save any kind of transaction information. Individual consumers are not at risk of exposing their name, card number, or security code to retailers or by-standers. Customers do not have to carry their phones, credit cards, and/or cash in order to make electronic payments. In some embodiments, devices are waterproof and remain operational for several days or months. The systems of this aspect of the invention are able to work in conjunction with mobile phone applications developed specifically for payment transactions. In some embodiments, if removed from the nail or tissue, the invented device is permanently disabled and all payment information is destroyed.

Example 4—Fingernail Mounted NFC for Personal Identification/Authorization

The invention provides, for example, fingernail mounted near field communication (NFC) devices providing a unique solution for personal identification in the alcohol distribution, restaurant, bar, education, and/or health-care industries. The materials, design, and circuit integration enable the art of biocompatible NFC technology. In some embodiments, for example, the built-in NFC technology serves as a digital replacement for drivers' licenses and school identification cards. The fingernail-mounted devices of this aspect, for example, are able to wirelessly communicate with point of access readers that use NFC antennas. Instead of carrying personal identification cards, fingernail-mounted devices are able to serve as proof of an individual's identification and/or store pertinent private information.

In an embodiment, for example, the invention has a devoted chip that stores an encrypted identification number that is unique to each individual device. In addition, the chip has action-specific security codes that change after each point of entry. The encrypted identification numbers can serve as a valid form of identification. For instance, "John Smith" (Adult Male Age: 45) uses his fingernail-mounted device as proof that is he over the age of 21 to purchase alcohol.

In some embodiments, for privacy, individual users are not at risk of exposing their name, age, and/or address. In some embodiments, the devices are waterproof and remain operational for several days or months. The systems of this aspect of the invention are able to work in conjunction with mobile phone applications developed specifically for authentication purposes. In some embodiments, if removed from the nail or tissue, the invented device is permanently disabled and all private information is destroyed.

Example 5—Fingernail Mounted NFC for Key Access/Authentication

The invention provides, for example, fingernail mounted near field communication (NFC) devices providing a unique solution for key access to places of residence, offices, hotels, and/or safe industries. The materials, design, and circuit integration enable the art of biocompatible NFC technology. In some embodiments, for example, the built-in NFC technology serves as a digital replacement for all physical keys. The fingernail-mounted devices of this aspect, for example, are able to wirelessly communicate with point of access readers that use NFC antennas. The point of access readers include but are not limited to door handles, windows, counter-tops, lockers, safes, and/or automobiles. Instead of carrying around keys, key cards, and/or wallets, authorized fingernail mounted device users are granted access to specific areas, buildings, rooms, and/or automobiles.

In an embodiment, for example, the invention has a devoted chip that stores an encrypted identification number that is unique to each individual device. In addition, the chip has action-specific security codes that change after each point of entry. Based off volunteered personal information, the encrypted identification numbers have access to designated areas. For instance, the invented device is able to unlock hotel room doors.

In some embodiments, for privacy, individual users are not at risk of exposing their name, room number, and/or access restrictions to third-party retailers or by-standers. Customers are not required to carry their cell phones, keys, and/or identification cards to gain access authorization. In some embodiments, the devices are waterproof and remain operational for several days or months. The systems of this aspect of the invention are able to work in conjunction with mobile phone applications developed specifically for authentication purposes. In some embodiments, if removed from the nail or tissue, the invented device is permanently disabled and all private information is destroyed.

Example 6—Finger and Toenail Mounted NFC Device for Hospital Monitoring/Tracking The invention provides, for example, tissue mounted near field communication (NFC) devices providing a unique service platform for monitoring and tracking hospital patients. The materials, design, and circuit integration enable the art of biocompatible NFC technology. In some embodiments, the built-in NFC technology serves as a digital replacement for the hospital identification wristbands and bio-sensing electrodes using copper wire leads. The fingernail-mounted devices of this aspect are able to wirelessly communicate with point of access readers that use NFC antennas. The point of access readers include but are not limited to smartphones, door handles, windows, and/or counter-tops. The invented device gives health-care professionals a way to electronically track and monitor admitted hospital patients. The fingernail-mounted or tissue-mounted devices optionally provide additional bio-sensing modalities that measure temperature, pH levels, glucose, pulse-oximetry, heart rate, respiratory rate, blood pressure, ECG (electrocardiography), EOG (electrooxulography), EEG (electroencephalography), EMG (electromyography), PPG (photoplethysmogram), peripheral capillary oxygen saturation (SpO2), bilirubin level and/or bili light intensity and dose.

In some embodiments, for privacy, the invention has a devoted chip that stores an encrypted identification number that is unique to each individual device. In addition, the chip has action-specific security codes that change constantly. The encrypted device number helps keep patient health-care information private. Clinicians, hospital management, and insurance providers are the only users with access to the information. In case of emergency, hospital personnel can quickly locate missing patients and/or observe patient vital signs.

Individual users are no longer at risk of exposing their name and/or health-care information to by-standers. In some embodiments, the devices are waterproof and remain operational for several days or months. The systems of this aspect of the invention are able to work in conjunction with mobile phone applications developed specifically for authentication purposes. In some embodiments, if removed from the nail or tissue, the invented device is permanently disabled and all private information is destroyed.

Example 7—Finger and Toenail Mounted NFC Device for Safe Handling of Hazardous Equipment The invention provides, for example, tissue mounted near field communication (NFC) devices providing a unique solution for gun safety and safe handling of potentially hazardous machinery where safety is required. The present invention's materials, design, and circuit integration enable the art of biocompatible NFC technology. In an embodiment, the built-in NFC technology serves as an additional layer of safety and security in operating potentially life-threatening equipment. Life threatening equipment includes but is not limited to guns, saws, and/or cutting machinery. The fingernail-mounted devices of this aspect are able to wirelessly communicate with readers that use NFC antennas. The body designed, wearable NFC technology reduces the misuse of hazardous equipment through the use of radio frequency identification systems. Gun triggers are only able to discharge with the detection of an authorized fingernail-mounted device. The invented devices of certain embodiments can activate kill switches in industrial or trade cutting machinery when the user gets too close to a sharp object.

In an embodiment, the invention has a devoted chip that stores encrypted identification information that is unique to each individual device. In addition, the chip has action-specific security codes that change after time of authorization. The encrypted identification information and varying security codes are used to grant or deny operational access to hazardous equipment.

The systems of this aspect of the invention are able to work in conjunction with mobile applications developed specifically for smart guns and/or hazardous machinery. In some embodiments, the devices are waterproof and remain operational for several days or months. In some embodiments, if removed from the nail or tissue, the invented device is permanently disabled.

Example 8—Finger and Toenail Mounted NFC Device for Medication Bottle Compliance and Safety The invention provides, for example, tissue mounted near field communication (NFC) devices providing a unique solution for medication bottles and access to medication where compliance and/or safety is required. The presented invention's materials, design, and circuit integration enable the art of biocompatible NFC technology. In an embodiment, the built-in NFC technology serves as an additional layer of security and/or compliance monitor for medication bottles. The fingernail-mounted devices of this aspect are able to wirelessly communicate with readers that use NFC antennas. The body designed, wearable NFC technology is able to keep track of the amount of times a certain drug bottle is opened and prevents unauthorized individuals access to the medication through the use of radio frequency identification systems. Pill containers are only able to open with the detection of an authorized fingernail-mounted device.

In an embodiment, the invention has a devoted chip that stores encrypted identification information that is unique to each individual device. In addition, the chip has action-specific security codes that change after time of authorization. The encrypted identification information and varying security codes are used to grant or deny access to prescribed medication.

The systems of this aspect of the invention are able to work in conjunction with mobile applications. In some embodiments, the devices are waterproof and remain operational for several days or months. In some embodiments, if removed from the nail or tissue, the invented device is permanently disabled.

Example 9—Fingernail Mounted NFC Device for Hospital Hand Washing

The invention provides, for example, tissue mounted near field communication (NFC) devices, as a unique solution for hospital personnel in monitoring whether or not health-care professionals wash their hands before engaging with patients. The present invention's materials, design, and circuit integration enable the art of biocompatible NFC technology. In an embodiment, the built-in NFC technology serves as an additional health monitor and safety precaution. The fingernail-mounted devices of this aspect are able to wirelessly communicate with readers that use NFC antennas. The body designed, wearable NFC technology reduces the risk of health-care associated infections through the use of radio frequency identification systems. The invented device activates in close proximity to a reader installed at a sink, hand sanitizer station, and/or room access point. The reader records information from the activated device such as who washed their hands, at what time, for how long, and at what temperature. The point of access reader records who was present in specific locations. Data sets from both readers are correlated and used to determine failure to adhere to hand washing protocols and contaminated areas. The invented device holds the employee accountable and ensures a more sanitary environment.

In an embodiment, the invention has a devoted chip that stores encrypted information that is unique to each individual device. In addition, the chip has action-specific security codes that change after time of authorization. The encrypted information and varying security codes are used to accurately identify individuals. In some embodiments, the devices are waterproof and remain operational for several days or months. In some embodiments, if removed from the nail or tissue, the invented device is permanently disabled.

Example 10—Fingernail Mounted NFC Device for Gaming, Music-Sharing, Social and Digital Media Platforms The invention provides, for example, fingernail mounted near field communication (NFC) devices providing a unique platform for gaming, music-sharing, social and digital media service providers. The materials, design, and circuit integration enable the art of biocompatible NFC technology. The fingernail-mounted devices of this aspect are able to wirelessly communicate with smartphones that have NFC capability. Instead of exchanging phone numbers, email addresses, and/or home addresses, users have the ability to privately share digital content and/or personal information.

In some embodiments, the invention has a devoted chip that stores encrypted personal identification numbers that are unique to each individual device. The encrypted information is a way to privately disclose digital content and information. In some embodiments, personal information is never shared with merchants or stored on a server without user consent. In some embodiments, all digital information is stored and shared locally on the consumers' personal mobile devices, computers, web pages, and/or gaming systems.

In some embodiments, for privacy, individual consumers are not at risk of exposing personal information or digital content with unauthorized parties. Customers do not have to carry their phones and/or business cards to disclose private information. In some embodiments, devices are waterproof and remain operational for several days or months. The systems of this aspect of the invention are able to work in conjunction with mobile phone applications developed specifically for media sharing purposes. In some embodiments, if removed from the nail, the invented device is permanently disabled and all digital content is destroyed.

Example 11—Actuating Tissue Mounted Devices

The invention provides, for example, fingernail-mounted near field communication (NFC) devices providing a unique platform for consumer, defense, and or intelligence agencies. The materials, design, and circuit integration enable the art of biocompatible NFC technology. The fingernail-mounted devices of this aspect are able to wirelessly communicate with smartphones and other devices that have NFC capability. Users have the ability to trigger a response that permanently disables device functionality and erases all digital content in the event of termination of use and or unauthorized possession.

Example 12—Tissue Mounted Devices

The systems and methods of the invention are highly versatile and support a broad range of applications. This example illustrates a range of different device embodiments supporting many different applications. The following description provides examples showing the broad capabilities of the present systems. The common components of the exemplified systems include a substrate that has an antenna and inorganic and/or organic electronic components within the system's dimensions, most of which include but are not limited to a RFID IC that can take on various ISO and non ISO compliant forms. The components are configured to be used in either an active or passive state depending on the application. The devices exemplified have dimensions and geometries allowing for electromagnetic and mechanical form factors which optimally match the desired application.

Example 13—Tissue Mounted Devices

The systems and methods of the invention are highly versatile and support a broad range of applications. This example illustrates a range of different device embodiments supporting many different applications. The following description provides examples showing the broad capabilities of the present systems. The common components of the exemplified systems include a substrate that has an antenna and inorganic and/or organic electronic components within the system's dimensions, most of which include but are not limited to a RFID IC that can take on various ISO and non ISO compliant forms. The components are configured to be used in either an active or passive state depending on the application. The devices exemplified have dimensions and geometries allowing for electromagnetic and mechanical form factors which optimally match the desired application.

Figure 17:
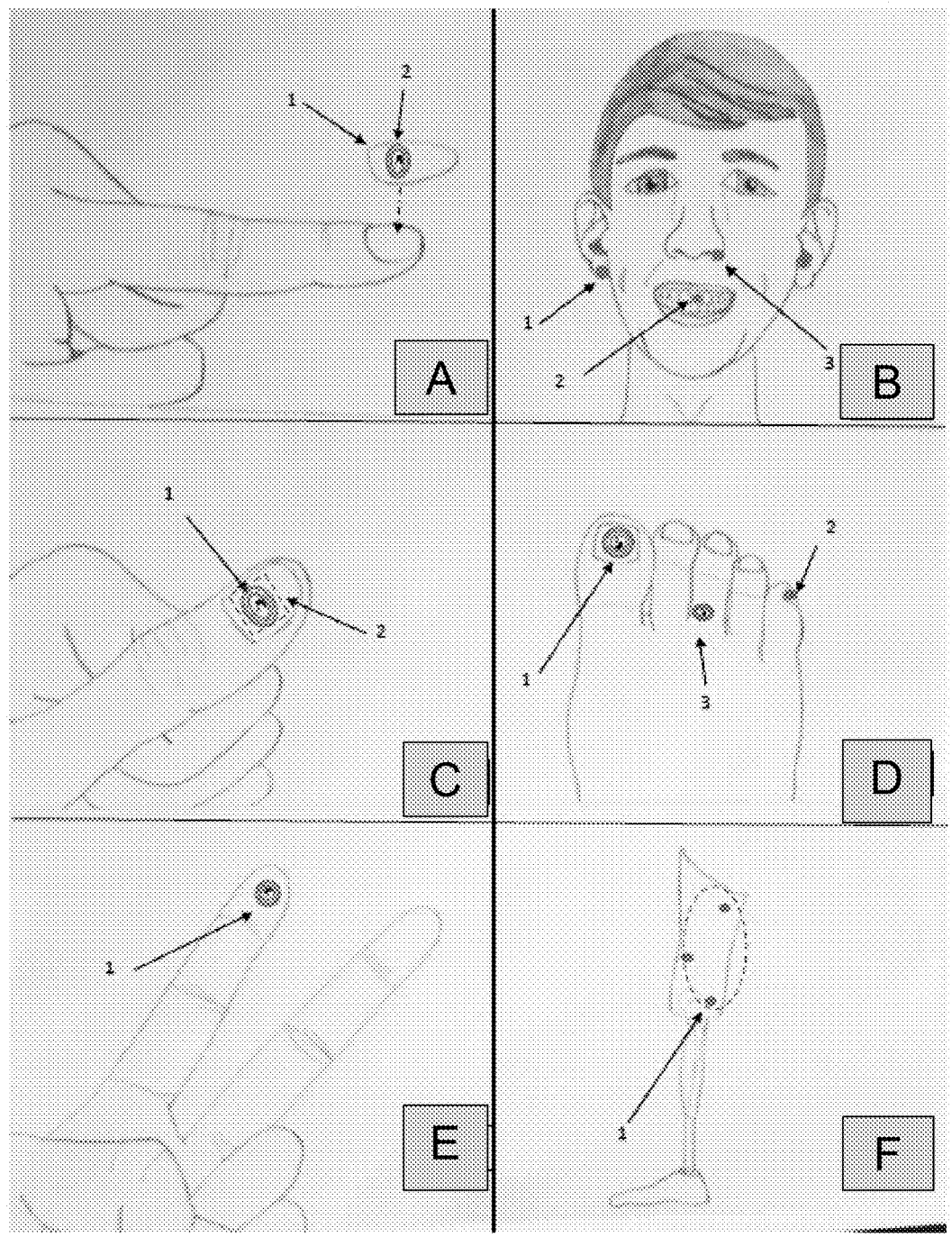
FIG. 17, A-F provides schematic diagrams of various tissue mounted systems of the invention.

FIG. 17 provides schematic diagrams of various tissue mounted systems of the invention.

FIG. 17A illustrates a finger of a person on which a fingernail (faux or other) 1 having a tissue mounted system 2 of the invention attached is being placed on the fingernail of a person by means of an adhesive.

FIG. 17B illustrates the head of a person with several different tissue mounted systems attached in different locations using different methods. One or all of the locations shown, and other locations not shown, may be used, but preferred embodiments on the head are illustrated here. Element 1 shows a tissue mounted system attached to the ear which contains memory and/or electronic sensors. Element 2 shows a tissue mounted system attached to the tooth using an appropriate adhesive safe for this attachment, the device contains memory and/or electronic sensors. Element 3 shows a tissue mounted system containing electronics and/or sensors located on or in close proximity of the nose.

FIG. 17C illustrates a finger of a human with a tissue mounted system comprising a memory and/or electronic components/sensors mounted using an adhesive directly to the nail plate. The device 1 is sometimes covered with an additional cover material 2, such as an encapsulation or cover layer.

FIG. 17D shows a person's foot. Located on the foot are three different tissue mounted systems. Elements 1,2 are located directly on the nail plate using appropriate adhesive and comprise memory and/or electronics/sensors. Element 3 shows a tissue mounted system with memory and/or electronics/sensors located on the toe mounted directly to the skin with an appropriate adhesive.

FIG. 17E illustrates the inside portion of a person's hand with a tissue mounted system 1 mounted on the finger over the fingerprint using appropriate adhesives. The devices comprise memory and/or electronics/sensors.

FIG. 17F illustrates a prosthetic socket with a dashed line showing a semitransparent view to expose the tissue mounted system 1 mounted on the human limb. The tissue mounted systems 1 contain memory and/or electronics/sensors.

Figure 18:
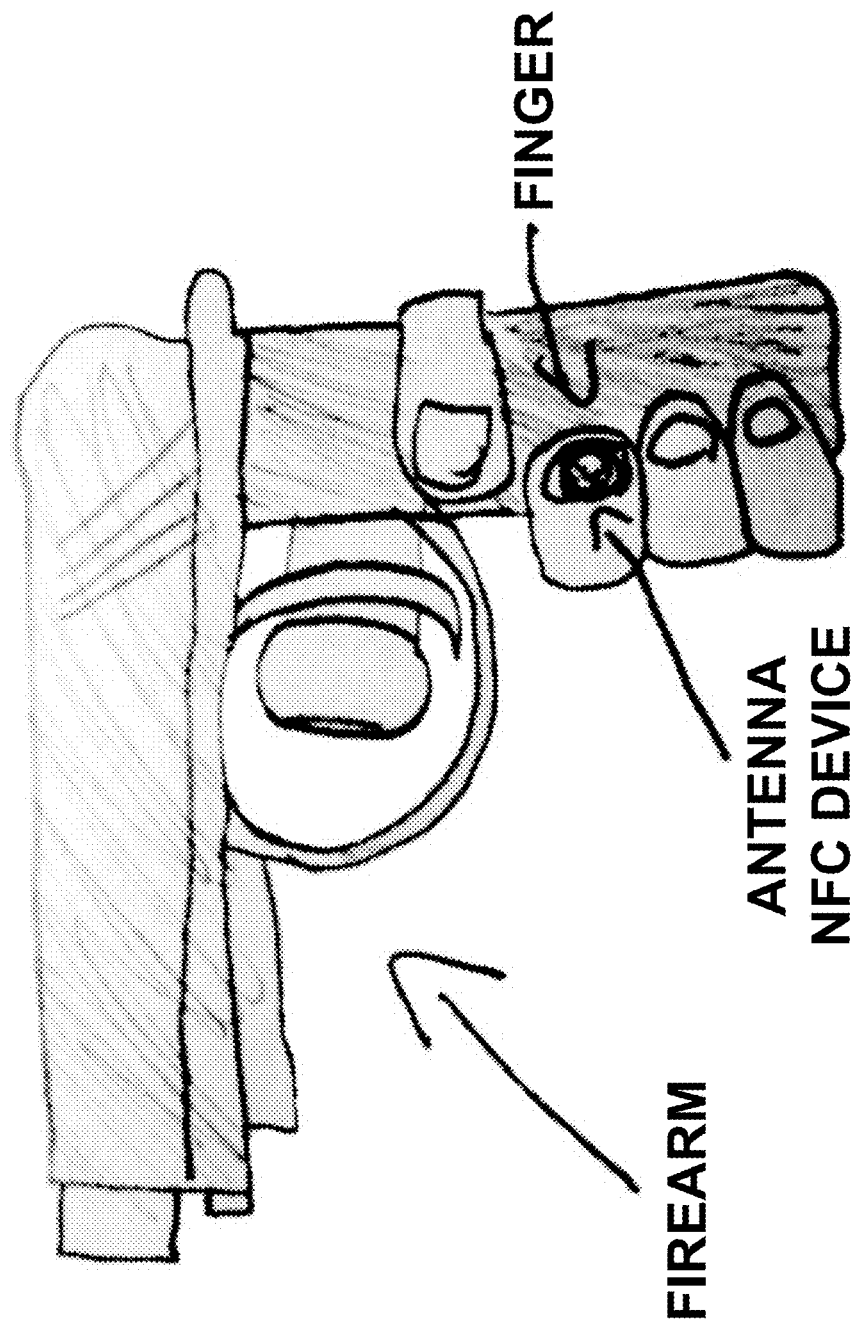
FIG. 18 provides a schematic illustration of a tissue mounted NFC device mounted on the fingernail for authentication in connection with use of a firearm.
Figure 19:
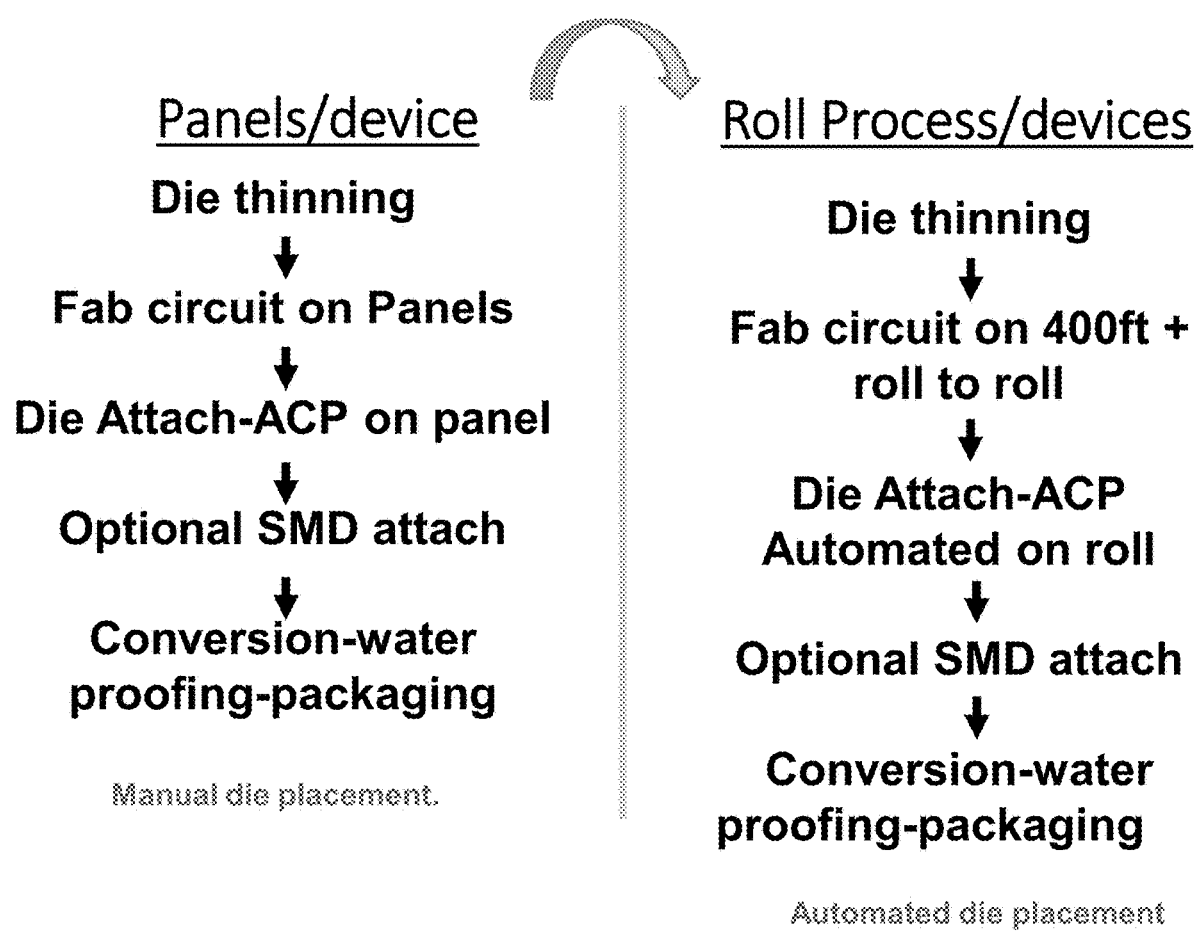
FIG. 19 provides a process flow diagram illustrating a method for making devices of the invention.
Figure 20:
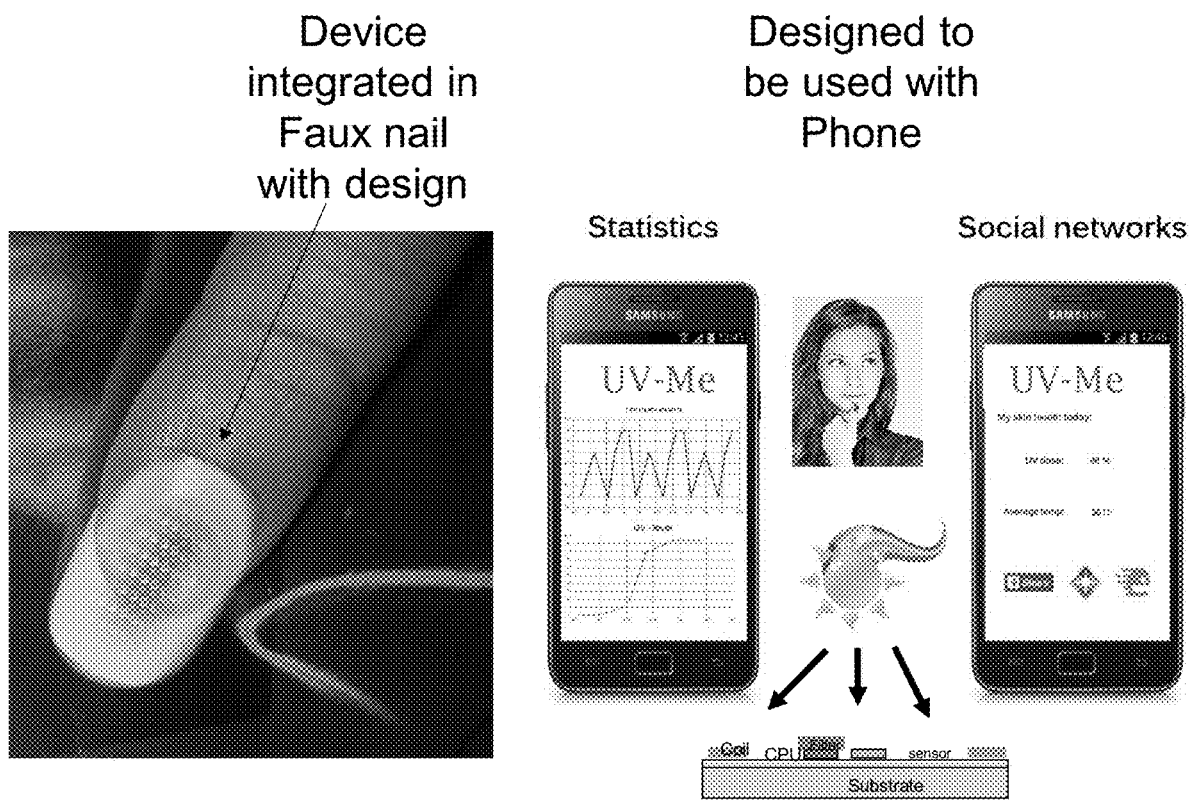
FIG. 20 provides an illustration of the interface of a device of the present invention with a mobile device, such as a mobile phone.
Figure 22:
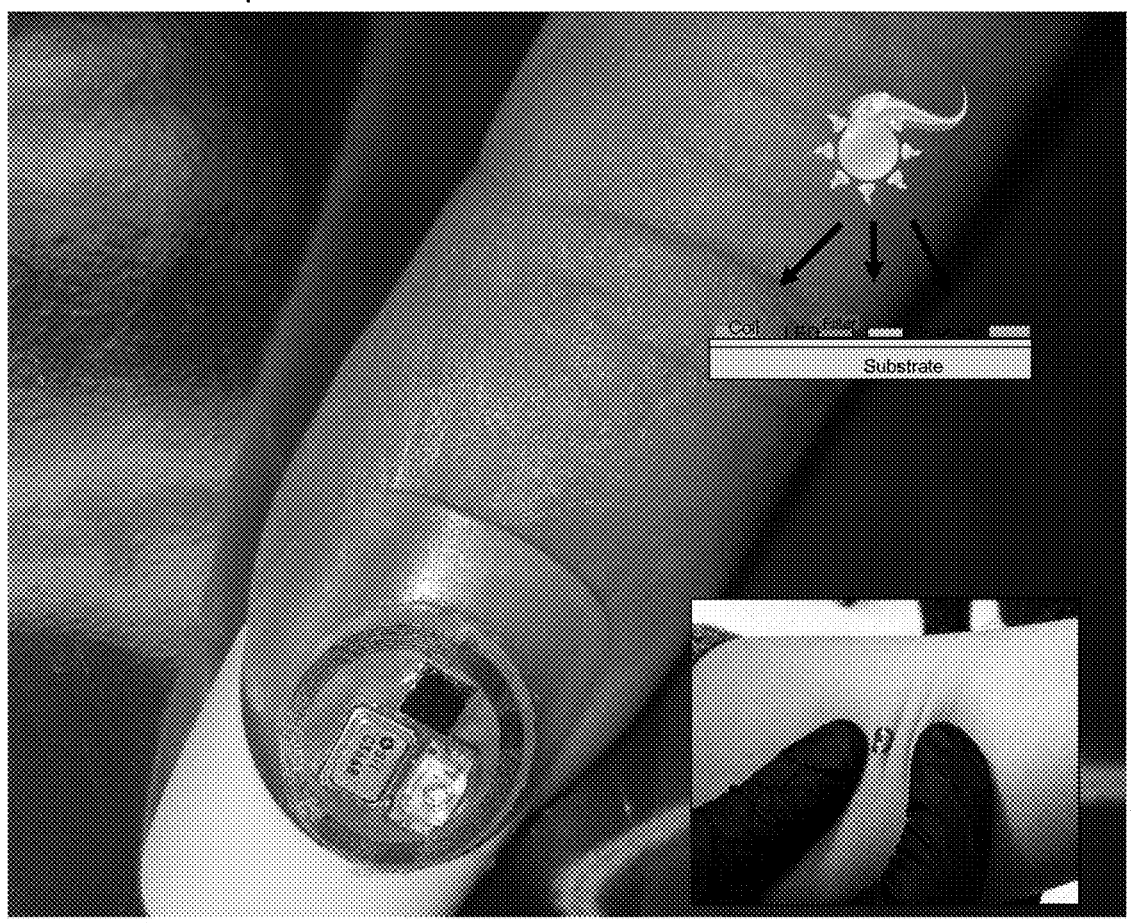
FIG. 22 provides photographs and a device schematic (inset) of ultraminiaturized, UV sensors of the invention.
Figure 23:
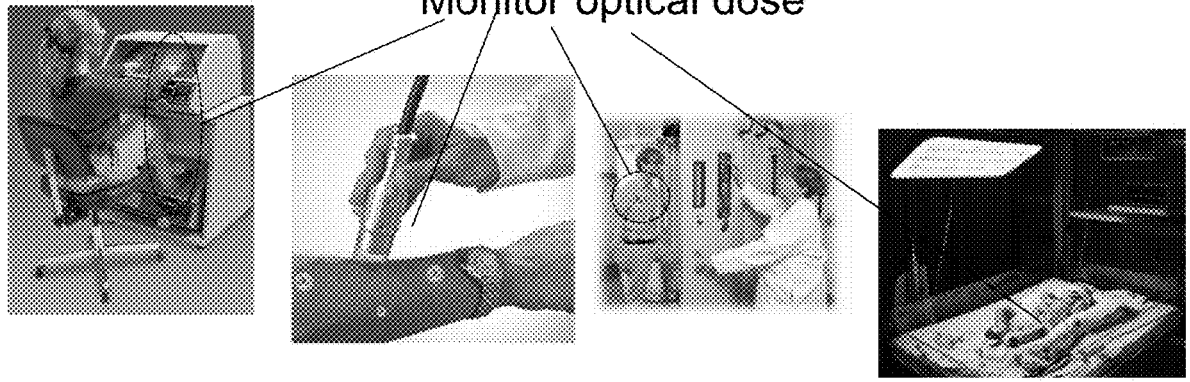
FIG. 23 provides a schematic illustration of example applications of devices of the invention for skin or nail mounted sensors of exposure in UV phototherapy.
Figure 25:
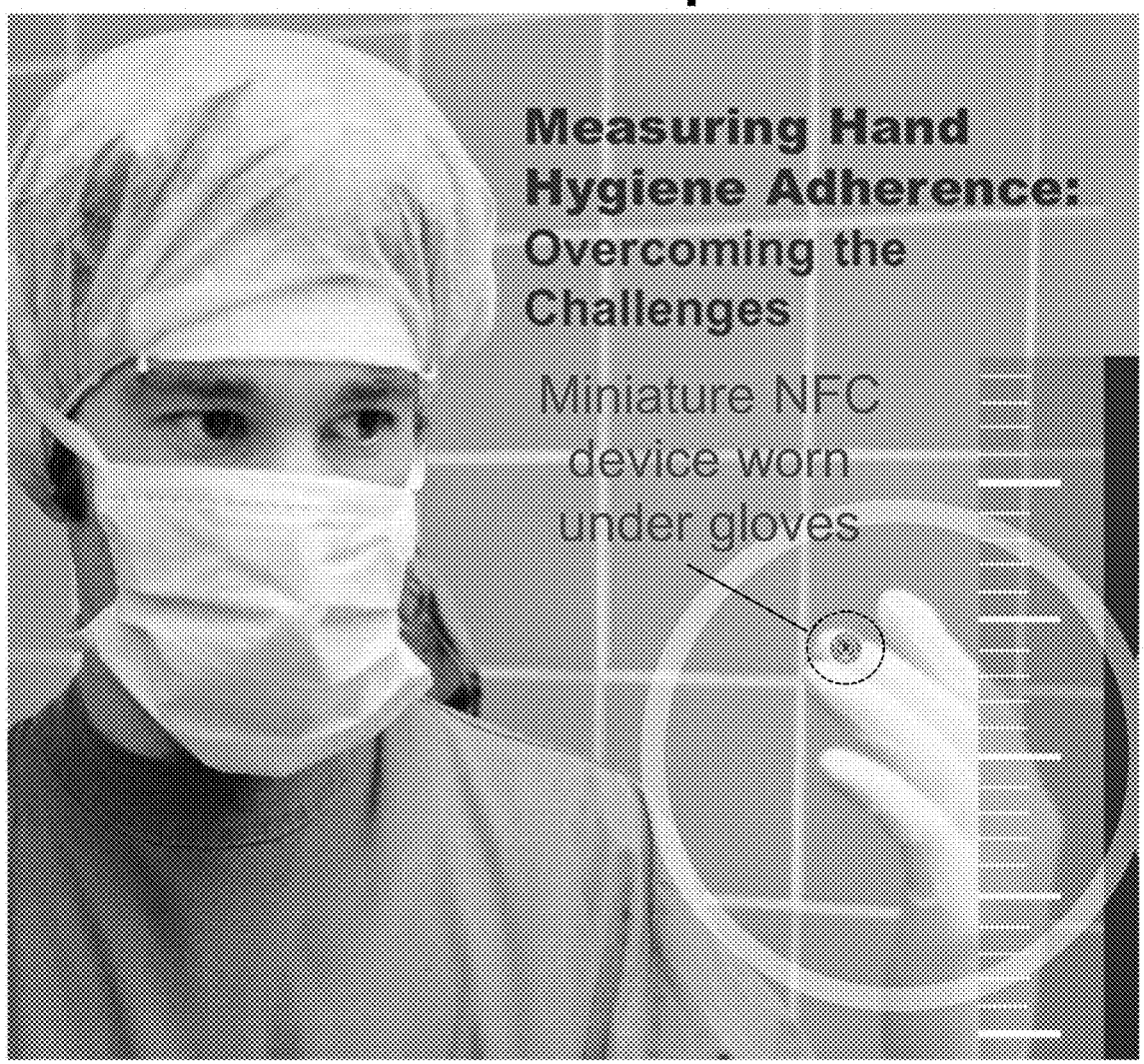
FIG. 25 provides a schematic illustration of example applications of devices of the invention for infectious disease compliance.
Figure 27:
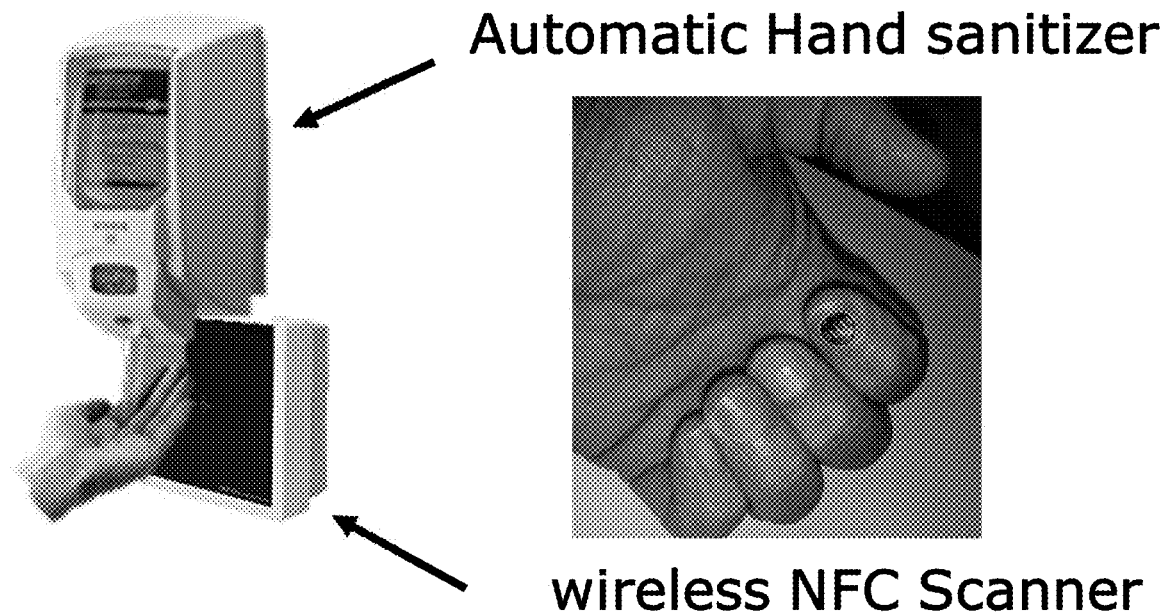
FIG. 27 provides a schematic illustration of example applications of devices of the invention for infectious disease compliance.
Figure 28:
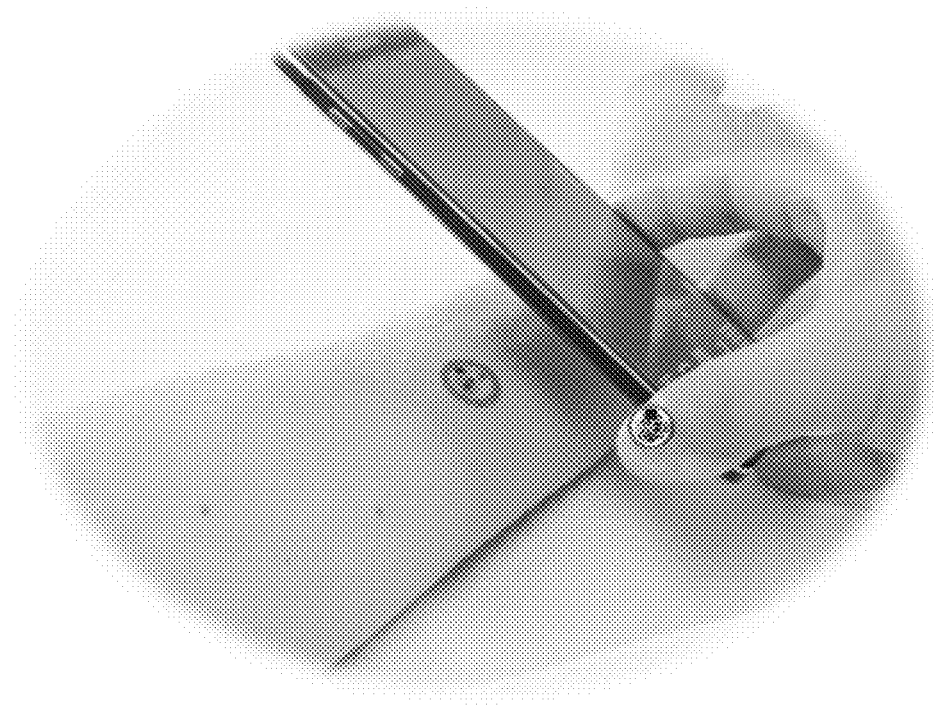
FIG. 28 provides a schematic illustration of example applications of devices of the invention for pulse oximetry and colorimeter.
Figure 31:
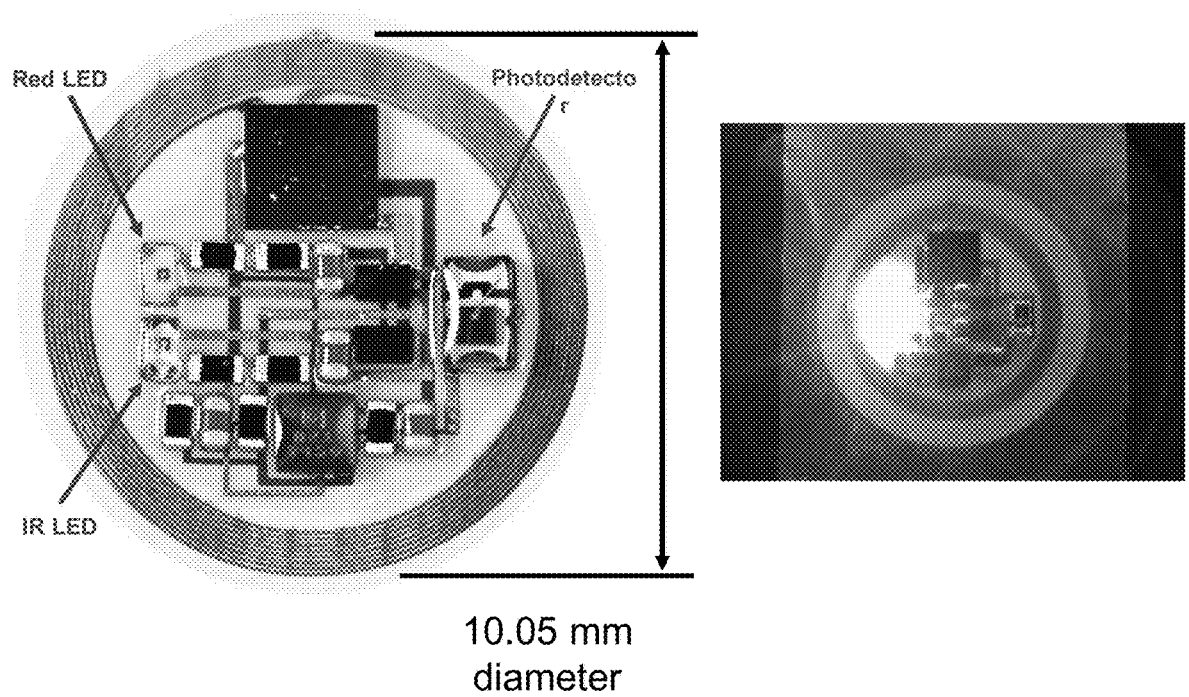
FIG. 31 provides a schematic illustration a device of the invention for fingernail oximetry.
Figure 32:
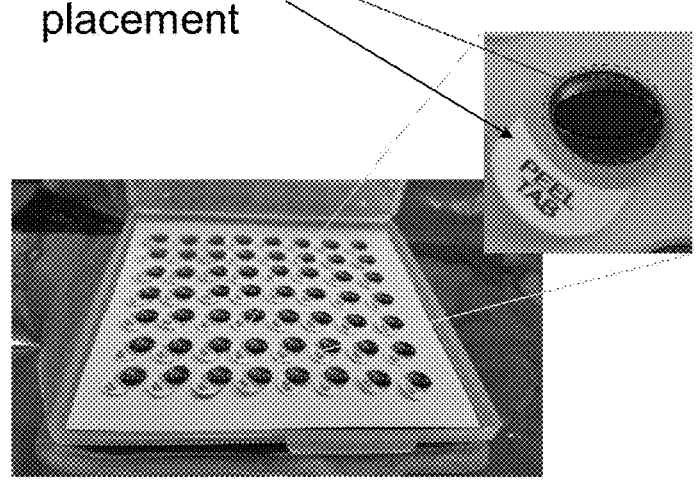
FIG. 32 provides a schematic illustration a device of the invention employing deployment via a pull tab configuration.
Figure 33:
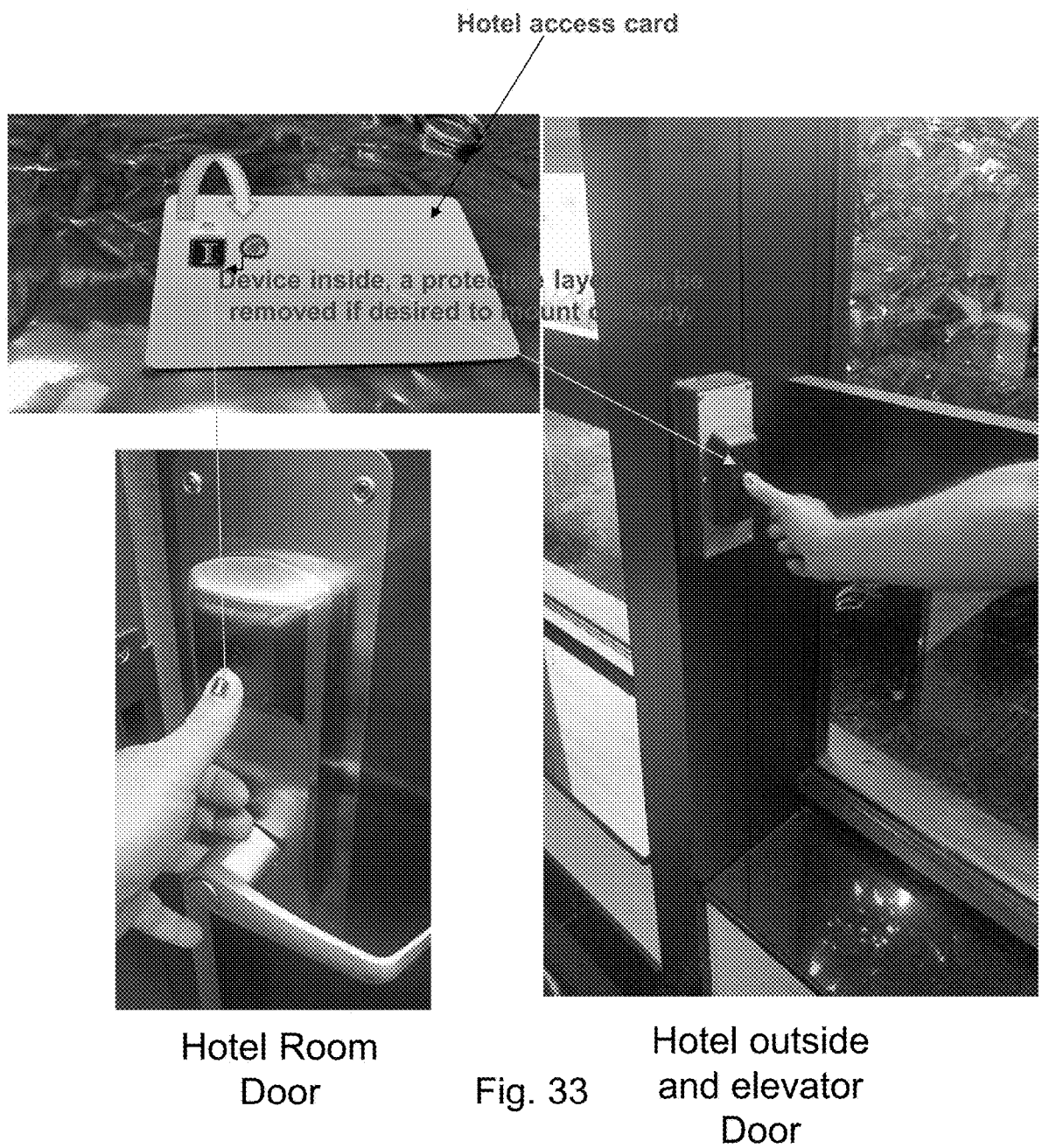
FIG. 33 provides a schematic illustration of example applications of devices of the invention for authentication.
Figure 34:
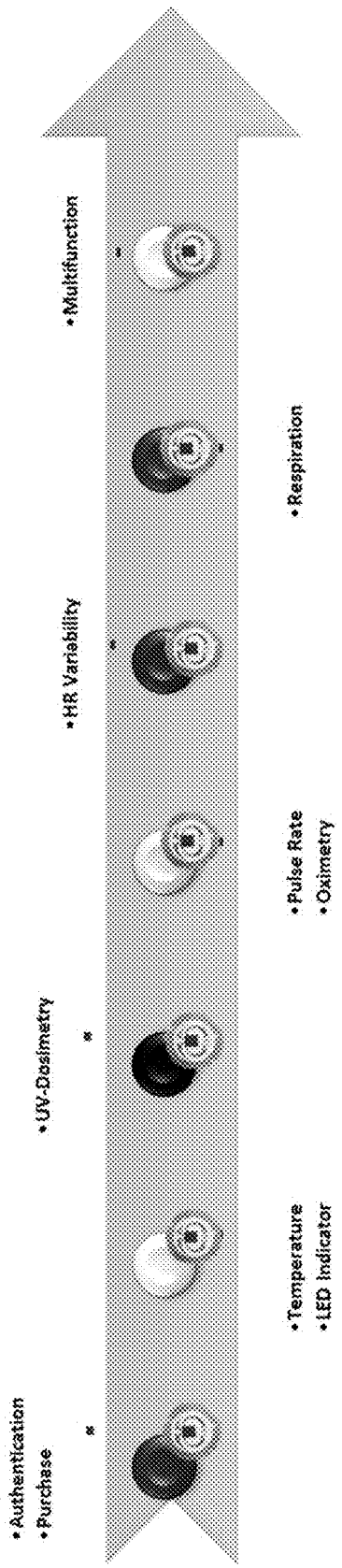
FIG. 34 provides a schematic illustration of example applications of devices of the invention

FIG. 18 provides a schematic illustration of a tissue mounted NFC device mounted on the fingernail for authentication in connection with use of a firearm.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, and method steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individually or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

Many of the molecules disclosed herein contain one or more ionizable groups [groups from which a proton can be removed (e.g., —COOH) or added (e.g., amines) or which can be quaternized (e.g., amines)]. All possible ionic forms of such molecules and salts thereof are intended to be included individually in the disclosure herein. With regard to salts of the compounds herein, one of ordinary skill in the art can select from among a wide variety of available counterions those that are appropriate for preparation of salts of this invention for a given application. In specific applications, the selection of a given anion or cation for preparation of a salt may result in increased or decreased solubility of that salt.

Every formulation or combination of components described or exemplified herein can be used to practice the invention, unless otherwise stated.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A tissue mounted electronic system, the system comprising:
    a substrate having an inner surface and an outer surface; and
    an electronic device comprising one or more inorganic components, organic components or a combination of inorganic and organic components supported by said outer surface of said substrate; wherein said electronic device has a thickness less than or equal to 5 millimeters and has lateral dimensions small enough to provide long-term conformal integration with a tissue without substantial delamination;
    wherein the electronic device comprises one or more near-field communication coils; and
    wherein the one or more near-field communication coils are coated in an electrically insulating coating;
    wherein the electrically insulating coating encapsulates the one or more near-field communication coils such that a gap is formed between the coating of adjacent turns of the one or more coils.

2. The system of claim 1, wherein the electrically insulating coating is a polyimide coating.

3. The system of claim 1, wherein the one or more near-field communication coils are disposed coincident with or proximate to the neutral mechanical surface of the device.

4. The system of claim 1, comprising a first near-field communication coil and a second near-field communication coil, wherein the first and second near-field communication coils are separated by the electrically insulating layer.

5. The system of claim 4 wherein the first near-field communication coil is stacked on top of the second near-field communication coil.

6. The system of claim 1, wherein said inner surface of said substrate conforms to a curvature of a surface of the tissue.

7. The system of claim 1, wherein said substrate is characterized by an average thickness greater than 5 microns.

8. The system of claim 1, wherein said substrate is characterized by a maximum thickness of 50 microns.

9. The system of claim 1, wherein the electronic device is a flexible electronic device or a stretchable electronic device.

10. The system of claim 1, wherein said one or more coils have a geometry selected from the group consisting of an annulus or an elliptical annulus.

11. The system of claim 1, wherein said inner surface of the substrate is bonded to said tissue surface via an adhesive comprising an acrylic, silicone or a combination of these.

12. The system of claim 1, wherein said inorganic or organic components are selected from semiconductor components, metallic conductor components and combinations of inorganic semiconductor components, organic semiconductor components and metallic conductor components.

13. The system of claim 1, wherein each of said inorganic or organic components is independently positioned within 10 millimeters of an edge of the perimeter of said substrate.

14. The system of claim 1, wherein said tissue mounted electronic system has a lateral area footprint less than or equal to 500 mm$^2$.

15. The system of claim 1, wherein said tissue mounted electronic system has a lateral area footprint selected from the range of 1 mm$^2$ to 500 mm$^2$.

16. The system of claim 1, wherein said tissue mounted electronic system has an average thickness selected from the range of 5 microns to 5 millimeters.

17. The system of claim 1, wherein said tissue mounted electronic system has an overall maximum thickness less than 0.1 mm and at least one region having a thickness selected from the range of 0.05 mm to 0.09 mm.

18. The system of claim 1, wherein the system has a multilayer geometry comprising a plurality of functional layers, supporting layers, encapsulating layers, planarizing layers or any combination of these.

19. The system of claim 1, wherein said substrate is a flexible substrate or a stretchable substrate.

* * * * *